US012630642B2

(12) United States Patent
Zhou et al.

(10) Patent No.: US 12,630,642 B2
(45) Date of Patent: May 19, 2026

(54) ANTIGEN BINDING PROTEINS THAT BIND BCMA

(71) Applicant: Sorrento Therapeutics, Inc., San Diego, CA (US)

(72) Inventors: Heyue Zhou, San Diego, CA (US); Xia Cao, San Diego, CA (US)

(73) Assignee: Vivasor, Inc., San Diego, CA (US)

( * ) Notice: Subject to any disclaimer, the term of this patent is extended or adjusted under 35 U.S.C. 154(b) by 1088 days.

(21) Appl. No.: 17/412,089

(22) Filed: Aug. 25, 2021

(65) Prior Publication Data

US 2021/0388097 A1      Dec. 16, 2021

Related U.S. Application Data

(63) Continuation of application No. PCT/US2020/019763, filed on Feb. 25, 2020.

(60) Provisional application No. 62/811,431, filed on Feb. 27, 2019, provisional application No. 62/810,771, filed on Feb. 26, 2019.

(51) Int. Cl.
*C07K 16/28*          (2006.01)

(52) U.S. Cl.
CPC ...... *C07K 16/2878* (2013.01); *C07K 2317/21* (2013.01); *C07K 2317/33* (2013.01); *C07K 2317/55* (2013.01); *C07K 2317/622* (2013.01); *C07K 2317/76* (2013.01); *C07K 2317/92* (2013.01)

(58) Field of Classification Search
CPC ...................... C07K 2317/76; A61K 2039/505
See application file for complete search history.

(56) References Cited

U.S. PATENT DOCUMENTS

| | | |
|---|---|---|
| 2005/0031614 A1 | 2/2005 | Roskos et al. |
| 2007/0044171 A1 | 2/2007 | Kovalic et al. |
| 2014/0134189 A1 | 5/2014 | MacDonald et al. |
| 2016/0244528 A1 | 8/2016 | Gray et al. |
| 2017/0051068 A1 | 2/2017 | Pillarisetti et al. |
| 2020/0224160 A1* | 7/2020 | Ding ..................... C12N 15/111 |

FOREIGN PATENT DOCUMENTS

| | | |
|---|---|---|
| JP | 2018525005 A | 9/2018 |
| JP | 2016500256 B | 11/2018 |
| JP | 2018516068 B | 7/2021 |
| WO | 1999010494 A2 | 3/1999 |
| WO | 2000063252 A1 | 10/2000 |
| WO | 2009026303 A1 | 2/2009 |
| WO | 2014089335 A2 | 6/2014 |
| WO | 2016166629 A1 | 10/2016 |
| WO | 2017031104 A1 | 2/2017 |
| WO | 2017143069 A1 | 8/2017 |
| WO | 2019025983 A1 | 2/2019 |
| WO | 2021046445 A1 | 3/2021 |

OTHER PUBLICATIONS

Ahmad et. al. Clin Dev Immunol. 1-15. (2012) (Year: 2012).*
Vormittag et. al. Current Opinion in Biotechnology. 53:164-181. (2018) (Year: 2018).*
Cho et al., "Targeting B Cell Maturation Antigen (BCMA) in Multiple Myeloma: Potential Uses of BCMA-Based immunotherapy," Front. Immunol., Aug. 2018, vol. 9, Article 1821, pp. 1-15.
International Search Report corresponding to International Patent Application No. PCT/US2020/019763, mailed Jul. 23, 2020, 15 pages.
Shah et al., "B-cell maturation antigen (BCMA) in multiple myeloma: rationale for targeting and current therapeutic approaches," Leukemia (2020) 34: 985-1005.
Uniprot Accession No. A4PBK6_9METZ, Six-C from Sycon calcaravis, May 15, 2007 [online].[Retrieved on Jun. 6, 2020]. Retrieved from the internet: URL: https://www.uniprot.org/uniprot/A4PBK6, Entire document.
EPO Extended European Search Report corresponding to European Patent Application No. 20763127.6, mailed Nov. 28, 2022, 11 pages.
Kinneer Krista et al: "Preclinical assessment of an antibody-PED conjugate that targets BCMA on multiple myeloma and myeloma progenitor cells", Leukemia, Nature Publishing Group UK, London, vol. 33, No. 3, Oct. 12, 2018 (Oct. 12, 2018), pp. 766-771.
Frenzel et al., "Phage display-derived human antibodies in clinical development and therapy," mAbs, 2016 8(7): 1177-1194.

* cited by examiner

*Primary Examiner* — Meera Natarajan
*Assistant Examiner* — Francesca Edgingtongiordano
(74) *Attorney, Agent, or Firm* — McNeill PLLC

(57)          ABSTRACT

The present disclosure provides BCMA binding proteins, particularly anti-BCMA antibodies, or antigen-binding portions thereof, that specifically bind BCMA and uses thereof. In one embodiment, the anti-BCMA antibody comprises an antigen binding portion that binds a human BCMA epitope and blocks binding (e.g, inhibits binding) of human APRIL and/or human BAFF to the human BCMA epitope. Various aspects of the anti-BCMA antibodies relate to antibody fragments, single-chain antibodies, pharmaceutical compositions, nucleic acids, recombinant expression vectors, host cells, and methods for preparing and using such anti-BCMA antibodies. Methods for using the anti-BCMA antibodies include in vitro and in vivo methods for binding BCMA, detecting BCMA and treating diseases associated with BCMA over-expression.

18 Claims, 17 Drawing Sheets

Specification includes a Sequence Listing.

DS: disulfide bridge
*: beginning and end of EYFDSLLH
segment

SEQUENCE LISTING

```
<160> NUMBER OF SEQ ID NOS: 92

<210> SEQ ID NO 1
<211> LENGTH: 50
<212> TYPE: PRT
<213> ORGANISM: Homo sapiens
<220> FEATURE:
<221> NAME/KEY: misc_feature
<223> OTHER INFORMATION: Wild type Human BCMA protein (5-54)

<400> SEQUENCE: 1

Ala Gly Gln Cys Ser Gln Asn Glu Tyr Phe Asp Ser Leu Leu His Ala
1               5                   10                  15

Cys Ile Pro Cys Gln Leu Arg Cys Ser Ser Asn Thr Pro Pro Leu Thr
            20                  25                  30

Cys Gln Arg Tyr Cys Asn Ala Ser Val Thr Asn Ser Val Lys Gly Thr
        35                  40                  45

Asn Ala
    50

<210> SEQ ID NO 2
<211> LENGTH: 54
<212> TYPE: PRT
<213> ORGANISM: Homo sapiens
<220> FEATURE:
<221> NAME/KEY: misc_feature
<223> OTHER INFORMATION: Wild type Human BCMA protein (1-54)

<400> SEQUENCE: 2

Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
            20                  25                  30

Pro Pro Leu Thr Cys Gln Arg Tyr Cys Asn Ala Ser Val Thr Asn Ser
        35                  40                  45

Val Lys Gly Thr Asn Ala
    50

<210> SEQ ID NO 3
<211> LENGTH: 54
<212> TYPE: PRT
<213> ORGANISM: Homo sapiens
<220> FEATURE:
<221> NAME/KEY: misc_feature
<223> OTHER INFORMATION: Mutant-1 human BCMA protein
```

<400> SEQUENCE: 3

```
Met Leu Gln Met Ala Gly Gln Cys Ser Gln Asn Glu Tyr Phe Asp Ser
1               5                   10                  15

Gly Gly His Ala Cys Ile Pro Cys Gln Leu Arg Cys Ser Ser Asn Thr
            20                  25                  30

Pro Pro Leu Thr Cys Gln Arg Tyr Cys Asn Ala Ser Val Thr Asn Ser
        35                  40                  45

Val Lys Gly Thr Asn Ala
    50
```

<210> SEQ ID NO 4
<211> LENGTH: 53
<212> TYPE: PRT
<213> ORGANISM: Homo sapiens
<220> FEATURE:
<221> NAME/KEY: misc_feature
<223> OTHER INFORMATION: Mutant-2 human BCMA protein

<400> SEQUENCE: 4

```
Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Pro
            20                  25                  30

Pro Gly Thr Cys Gln Arg Tyr Cys Asn Ala Ser Val Thr Asn Ser Val
        35                  40                  45

Lys Gly Thr Asn Ala
    50
```

<210> SEQ ID NO 5
<211> LENGTH: 295
<212> TYPE: PRT
<213> ORGANISM: Artificial Sequence
<220> FEATURE:
<223> OTHER INFORMATION: Synthetic: Wild type human BCMA protein-mouse
    Fc

<400> SEQUENCE: 5

```
Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
            20                  25                  30

Pro Pro Leu Thr Cys Gln Arg Tyr Cys Asn Ala Ser Val Thr Asn Ser
        35                  40                  45

Val Lys Gly Thr Asn Ala Gly Leu Gly Gly Leu Val Asp Tyr Lys Asp
    50                  55                  60

Asp Asp Asp Lys Thr His Thr Cys Pro Pro Cys Lys Cys Pro Ala Pro
65                  70                  75                  80

Asn Leu Leu Gly Gly Pro Ser Val Phe Ile Phe Pro Pro Lys Ile Lys
                85                  90                  95

Asp Val Leu Met Ile Ser Leu Ser Pro Ile Val Thr Cys Val Val Val
                100                 105                 110

Asp Val Ser Glu Asp Asp Pro Asp Val Gln Ile Ser Trp Phe Val Asn
            115                 120                 125

Asn Val Glu Val His Thr Ala Gln Thr Gln Thr His Arg Glu Asp Tyr
        130                 135                 140

Asn Ser Thr Leu Arg Val Val Ser Ala Leu Pro Ile Gln His Gln Asp
145                 150                 155                 160
```

-continued

```
Trp Met Ser Gly Lys Glu Phe Lys Cys Lys Val Asn Asn Lys Asp Leu
              165                 170                 175

Pro Ala Pro Ile Glu Arg Thr Ile Ser Lys Pro Lys Gly Ser Val Arg
              180                 185                 190

Ala Pro Gln Val Tyr Val Leu Pro Pro Glu Glu Glu Met Thr Lys
              195                 200                 205

Lys Gln Val Thr Leu Thr Cys Met Val Thr Asp Phe Met Pro Glu Asp
              210                 215                 220

Ile Tyr Val Glu Trp Thr Asn Asn Gly Lys Thr Glu Leu Asn Tyr Lys
225                 230                 235                 240

Asn Thr Glu Pro Val Leu Asp Ser Asp Gly Ser Tyr Phe Met Tyr Ser
              245                 250                 255

Lys Leu Arg Val Glu Lys Lys Asn Trp Val Glu Arg Asn Ser Tyr Ser
              260                 265                 270

Cys Ser Val Val His Glu Gly Leu His Asn His His Thr Thr Lys Ser
              275                 280                 285

Phe Ser Arg Thr Pro Gly Lys
              290                 295
```

```
<210> SEQ ID NO 6
<211> LENGTH: 295
<212> TYPE: PRT
<213> ORGANISM: Artificial Sequence
<220> FEATURE:
<223> OTHER INFORMATION: Synthetic: Mutant-1 human BCMA protein-mouse Fc

<400> SEQUENCE: 6

Met Leu Gln Met Ala Gly Gln Cys Ser Gln Asn Glu Tyr Phe Asp Ser
1               5                   10                  15

Gly Gly His Ala Cys Ile Pro Cys Gln Leu Arg Cys Ser Ser Asn Thr
              20                  25                  30

Pro Pro Leu Thr Cys Gln Arg Tyr Cys Asn Ala Ser Val Thr Asn Ser
              35                  40                  45

Val Lys Gly Thr Asn Ala Gly Leu Gly Gly Leu Val Asp Tyr Lys Asp
              50                  55                  60

Asp Asp Asp Lys Thr His Thr Cys Pro Pro Cys Lys Cys Pro Ala Pro
65                  70                  75                  80

Asn Leu Leu Gly Gly Pro Ser Val Phe Ile Phe Pro Pro Lys Ile Lys
              85                  90                  95

Asp Val Leu Met Ile Ser Leu Ser Pro Ile Val Thr Cys Val Val Val
              100                 105                 110

Asp Val Ser Glu Asp Asp Pro Asp Val Gln Ile Ser Trp Phe Val Asn
              115                 120                 125

Asn Val Glu Val His Thr Ala Gln Thr Gln Thr His Arg Glu Asp Tyr
              130                 135                 140

Asn Ser Thr Leu Arg Val Val Ser Ala Leu Pro Ile Gln His Gln Asp
145                 150                 155                 160

Trp Met Ser Gly Lys Glu Phe Lys Cys Lys Val Asn Asn Lys Asp Leu
              165                 170                 175

Pro Ala Pro Ile Glu Arg Thr Ile Ser Lys Pro Lys Gly Ser Val Arg
              180                 185                 190

Ala Pro Gln Val Tyr Val Leu Pro Pro Glu Glu Glu Met Thr Lys
              195                 200                 205

Lys Gln Val Thr Leu Thr Cys Met Val Thr Asp Phe Met Pro Glu Asp
              210                 215                 220
```

-continued

```
Ile Tyr Val Glu Trp Thr Asn Asn Gly Lys Thr Glu Leu Asn Tyr Lys
225                 230                 235                 240

Asn Thr Glu Pro Val Leu Asp Ser Asp Gly Ser Tyr Phe Met Tyr Ser
                245                 250                 255

Lys Leu Arg Val Glu Lys Lys Asn Trp Val Glu Arg Asn Ser Tyr Ser
            260                 265                 270

Cys Ser Val Val His Glu Gly Leu His Asn His His Thr Thr Lys Ser
        275                 280                 285

Phe Ser Arg Thr Pro Gly Lys
        290                 295

<210> SEQ ID NO 7
<211> LENGTH: 294
<212> TYPE: PRT
<213> ORGANISM: Artificial Sequence
<220> FEATURE:
<223> OTHER INFORMATION: Synthetic: Mutant-2 human BCMA protein-mouse Fc

<400> SEQUENCE: 7

Met Leu Gln Met Ala Gly Gln Cys Ser Gln Asn Glu Tyr Phe Asp Ser
1                   5                   10                  15

Leu Leu His Ala Cys Ile Pro Cys Gln Leu Arg Cys Ser Ser Asn Pro
                20                  25                  30

Pro Gly Thr Cys Gln Arg Tyr Cys Asn Ala Ser Val Thr Asn Ser Val
            35                  40                  45

Lys Gly Thr Asn Ala Gly Leu Gly Gly Leu Val Asp Tyr Lys Asp Asp
        50                  55                  60

Asp Asp Lys Thr His Thr Cys Pro Pro Cys Lys Cys Pro Ala Pro Asn
65                  70                  75                  80

Leu Leu Gly Gly Pro Ser Val Phe Ile Phe Pro Pro Lys Ile Lys Asp
                85                  90                  95

Val Leu Met Ile Ser Leu Ser Pro Ile Val Thr Cys Val Val Val Asp
                100                 105                 110

Val Ser Glu Asp Asp Pro Asp Val Gln Ile Ser Trp Phe Val Asn Asn
            115                 120                 125

Val Glu Val His Thr Ala Gln Thr Gln Thr His Arg Glu Asp Tyr Asn
        130                 135                 140

Ser Thr Leu Arg Val Val Ser Ala Leu Pro Ile Gln His Gln Asp Trp
145                 150                 155                 160

Met Ser Gly Lys Glu Phe Lys Cys Lys Val Asn Asn Lys Asp Leu Pro
                165                 170                 175

Ala Pro Ile Glu Arg Thr Ile Ser Lys Pro Lys Gly Ser Val Arg Ala
                180                 185                 190

Pro Gln Val Tyr Val Leu Pro Pro Glu Glu Glu Met Thr Lys Lys
            195                 200                 205

Gln Val Thr Leu Thr Cys Met Val Thr Asp Phe Met Pro Glu Asp Ile
        210                 215                 220

Tyr Val Glu Trp Thr Asn Asn Gly Lys Thr Glu Leu Asn Tyr Lys Asn
225                 230                 235                 240

Thr Glu Pro Val Leu Asp Ser Asp Gly Ser Tyr Phe Met Tyr Ser Lys
                245                 250                 255

Leu Arg Val Glu Lys Lys Asn Trp Val Glu Arg Asn Ser Tyr Ser Cys
            260                 265                 270

Ser Val Val His Glu Gly Leu His Asn His His Thr Thr Lys Ser Phe
        275                 280                 285
```

-continued

Ser Arg Thr Pro Gly Lys
    290

<210> SEQ ID NO 8
<211> LENGTH: 118
<212> TYPE: PRT
<213> ORGANISM: Artificial Sequence
<220> FEATURE:
<223> OTHER INFORMATION: Synthetic: BCA7, BCA7-2C5, BCA7-2E1, BCA7-2D11,
      BCA7-2G2, BCA7-2D8, BCA7-2E8

<400> SEQUENCE: 8

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Ser Ser Thr Ala
            20                  25                  30

Trp Met Ser Trp Val Arg Gln Ala Pro Gly Lys Gly Leu Glu Trp Val
            35                  40                  45

Gly Arg Ile Lys Ser Lys Ser Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Phe Leu Gln Met Asn Ser Leu Lys Thr Glu Asp Thr Ala Val Tyr
                85                  90                  95

Tyr Cys Ala Lys Gly Gly Gly Thr Tyr Gly Tyr Trp Gly Gln Gly Thr
                100                 105                 110

Thr Val Thr Val Ser Ser
            115

<210> SEQ ID NO 9
<211> LENGTH: 110
<212> TYPE: PRT
<213> ORGANISM: Artificial Sequence
<220> FEATURE:
<223> OTHER INFORMATION: Synthetic: BCA7

<400> SEQUENCE: 9

Ser Tyr Val Leu Thr Gln Pro Ala Ser Val Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
            35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Ser Tyr Thr Ser Ser
                85                  90                  95

Gly Ser Tyr Val Phe Gly Thr Gly Thr Lys Leu Thr Val Leu
                100                 105                 110

<210> SEQ ID NO 10
<211> LENGTH: 113
<212> TYPE: PRT
<213> ORGANISM: Artificial Sequence
<220> FEATURE:
<223> OTHER INFORMATION: Synthetic: BC4C9

<400> SEQUENCE: 10

-continued

```
Glu Val Gln Leu Val Gln Ser Gly Ala Glu Val Lys Lys Pro Gly Ala
1               5                   10                  15

Ser Val Lys Val Ser Cys Lys Ala Phe Gly Tyr Thr Phe Thr Ser Tyr
            20                  25                  30

Asp Ile Asn Trp Val Arg Gln Ala Thr Gly Gln Gly Leu Glu Trp Met
            35                  40                  45

Gly Trp Met Asn Pro Asn Ser Gly Asn Thr Gly Tyr Ala Gln Lys Phe
        50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Gly Leu Gly Glu Trp Gly Gln Gly Thr Leu Val Thr Val Ser
            100                 105                 110

Ser

<210> SEQ ID NO 11
<211> LENGTH: 111
<212> TYPE: PRT
<213> ORGANISM: Artificial Sequence
<220> FEATURE:
<223> OTHER INFORMATION: Synthetic: BC4C9

<400> SEQUENCE: 11

Gln Ser Val Leu Thr Gln Pro Ala Ser Val Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
            35                  40                  45

Met Ile Tyr Asp Val Ser Lys Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ile Ser Tyr Ser Ser Ser
                85                  90                  95

Ser Thr Phe Tyr Val Phe Gly Thr Gly Thr Lys Val Thr Val Leu
            100                 105                 110

<210> SEQ ID NO 12
<211> LENGTH: 117
<212> TYPE: PRT
<213> ORGANISM: Artificial Sequence
<220> FEATURE:
<223> OTHER INFORMATION: Synthetic: BC5C4

<400> SEQUENCE: 12

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
            35                  40                  45

Ser Gly Ile Ser Trp Asn Ser Gly Ser Ile Gly Tyr Ala Asp Ser Val
        50                  55                  60

Lys Gly Arg Phe Thr Ile Ser Arg Asp Asn Ala Lys Asn Ser Leu Tyr
65                  70                  75                  80
```

```
Leu Gln Met Asn Ser Leu Arg Ala Glu Asp Thr Ala Val Tyr Tyr Cys
                85                  90                  95

Ala Thr Ile Asp Asn Val Ala Phe His Ser Trp Gly Gln Gly Thr Leu
            100                 105                 110

Val Thr Val Ser Ser
        115

<210> SEQ ID NO 13
<211> LENGTH: 111
<212> TYPE: PRT
<213> ORGANISM: Artificial Sequence
<220> FEATURE:
<223> OTHER INFORMATION: Synthetic: BC5C4

<400> SEQUENCE: 13

Gln Ser Val Leu Thr Gln Pro Pro Ser Ala Ser Gly Ser Pro Gly Gln
1               5                   10                  15

Ser Val Thr Ile Ser Cys Thr Gly Thr Ser Ser Asp Ile Gly Gly Tyr
            20                  25                  30

Asn Tyr Val Ser Trp Tyr Gln Gln His Pro Gly Lys Ala Pro Lys Leu
            35                  40                  45

Ile Ile Tyr Glu Val Ser Asn Arg Pro Ser Gly Val Ser Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Asp Asn
                85                  90                  95

Gly Ala Leu Val Val Phe Gly Gly Gly Thr Lys Leu Thr Val Leu
            100                 105                 110

<210> SEQ ID NO 14
<211> LENGTH: 120
<212> TYPE: PRT
<213> ORGANISM: Artificial Sequence
<220> FEATURE:
<223> OTHER INFORMATION: Synthetic: BC6G8

<400> SEQUENCE: 14

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Val Gly Trp His Trp Ile Arg Gln Ser Pro Ser Arg Gly Leu Glu
        35                  40                  45

Trp Leu Gly Arg Thr Tyr Tyr Arg Ser Asn Phe Ala Thr Asp Tyr Ala
    50                  55                  60

Ala Ser Val Arg Gly Arg Met Thr Ile Asn Ala Asp Thr Ser Thr Asn
65                  70                  75                  80

Gln Ile Ser Leu His Leu Asn Ser Leu Thr Pro Glu Asp Thr Ala Val
                85                  90                  95

Tyr Tyr Cys Thr Arg Asp Trp Tyr Gly Val Tyr Asp Phe Trp Gly Gln
            100                 105                 110

Gly Thr Leu Val Thr Val Ser Ser
        115                 120

<210> SEQ ID NO 15
<211> LENGTH: 109
<212> TYPE: PRT
<213> ORGANISM: Artificial Sequence
```

```
<220> FEATURE:
<223> OTHER INFORMATION: Synthetic: BC6G8

<400> SEQUENCE: 15

Ser Tyr Glu Leu Met Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Leu Val Val Phe Gly Gly Gly Thr Lys Leu Thr Val Leu
            100                 105

<210> SEQ ID NO 16
<211> LENGTH: 110
<212> TYPE: PRT
<213> ORGANISM: Artificial Sequence
<220> FEATURE:
<223> OTHER INFORMATION: Synthetic: BCA7-2C5

<400> SEQUENCE: 16

Gln Ser Ala Leu Thr Gln Pro Ala Ser Val Ser Gly Ser Pro Gly Gln
1               5                   10                  15

Ser Val Thr Ile Ser Cys Thr Gly Thr Ser Ser Ala His Gly Gly His
            20                  25                  30

Tyr Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Ser Tyr Thr Ser Ser
                85                  90                  95

Gly Ser Tyr Val Phe Gly Thr Gly Thr Lys Leu Thr Val Leu
            100                 105                 110

<210> SEQ ID NO 17
<211> LENGTH: 110
<212> TYPE: PRT
<213> ORGANISM: Artificial Sequence
<220> FEATURE:
<223> OTHER INFORMATION: Synthetic: BCA7-2E1

<400> SEQUENCE: 17

Gln Ser Ala Leu Thr Gln Pro Ala Ser Val Ser Gly Ser Pro Gly Gln
1               5                   10                  15

Ser Val Thr Ile Ser Cys Thr Gly Thr Ser Ser Asp Gly Gly Gly His
            20                  25                  30

Thr Tyr Val Ser Trp Tyr Gln Gln His Pro Gly Lys Ala Pro Lys Leu
        35                  40                  45

Met Ile Tyr Asp Val Ser Asn Arg Pro Ser Trp Val Ser Asn Arg Phe
    50                  55                  60
```

```
Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Ser Tyr Thr Ser Ser
                85                  90                  95

Gly Ser Tyr Val Phe Gly Thr Gly Thr Lys Leu Thr Val Leu
            100                 105                 110

<210> SEQ ID NO 18
<211> LENGTH: 110
<212> TYPE: PRT
<213> ORGANISM: Artificial Sequence
<220> FEATURE:
<223> OTHER INFORMATION: Synthetic: BCA7-2D11

<400> SEQUENCE: 18

Ser Tyr Glu Leu Thr Gln Pro Ala Ser Val Ser Gly Ser Pro Gly Gln
1               5                   10                  15

Ser Val Thr Ile Ser Cys Thr Gly Thr Ser Ser Val Val Gly Gly His
                20                  25                  30

Asp Tyr Val Ser Trp Tyr Gln Gln His Pro Gly Lys Ala Pro Lys Leu
            35                  40                  45

Met Ile Tyr Asp Val Ser Asn Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Ser Tyr Thr Ser Ser
                85                  90                  95

Gly Ser Tyr Val Phe Gly Thr Gly Thr Lys Val Thr Val Leu
            100                 105                 110

<210> SEQ ID NO 19
<211> LENGTH: 110
<212> TYPE: PRT
<213> ORGANISM: Artificial Sequence
<220> FEATURE:
<223> OTHER INFORMATION: Synthetic: BCA7-2G2

<400> SEQUENCE: 19

Gln Ser Val Leu Thr Gln Pro Ala Ser Val Ser Gly Ser Pro Gly Gln
1               5                   10                  15

Ser Val Thr Ile Ser Cys Thr Gly Thr Ser Ser Ser Val Gly Gly Arg
                20                  25                  30

Gln Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Ser Tyr Thr Ser Ser
                85                  90                  95

Gly Ser Tyr Val Phe Gly Thr Gly Thr Lys Leu Thr Val Leu
            100                 105                 110

<210> SEQ ID NO 20
<211> LENGTH: 110
<212> TYPE: PRT
<213> ORGANISM: Artificial Sequence
<220> FEATURE:
<223> OTHER INFORMATION: Synthetic: BCA7-2D8
```

-continued

```
<400> SEQUENCE: 20

Gln Ser Val Leu Thr Gln Pro Ala Ser Val Ser Gly Ser Pro Gly Gln
1               5                   10                  15

Ser Val Thr Ile Ser Cys Thr Gly Thr Ser Ser Ser Ile Gly Asp Ser
            20                  25                  30

Tyr Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Ser Tyr Thr Ser Ser
                85                  90                  95

Gly Ser Tyr Val Phe Gly Thr Gly Thr Thr Leu Thr Val Leu
            100                 105                 110

<210> SEQ ID NO 21
<211> LENGTH: 110
<212> TYPE: PRT
<213> ORGANISM: Artificial Sequence
<220> FEATURE:
<223> OTHER INFORMATION: Synthetic: BCA7-2E8

<400> SEQUENCE: 21

Gln Ser Val Leu Thr Gln Pro Ala Ser Val Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Ser Leu Arg Ser Asn
                85                  90                  95

Gly Asp Tyr Val Phe Gly Thr Gly Thr Thr Leu Thr Val Leu
            100                 105                 110

<210> SEQ ID NO 22
<211> LENGTH: 448
<212> TYPE: PRT
<213> ORGANISM: Artificial Sequence
<220> FEATURE:
<223> OTHER INFORMATION: Synthetic: BCA7-2C5 (IgG1 SPPC)

<400> SEQUENCE: 22

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Ser Ser Thr Ala
            20                  25                  30

Trp Met Ser Trp Val Arg Gln Ala Pro Gly Lys Gly Leu Glu Trp Val
        35                  40                  45

Gly Arg Ile Lys Ser Lys Ser Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80
```

-continued

```
Leu Phe Leu Gln Met Asn Ser Leu Lys Thr Glu Asp Thr Ala Val Tyr
                85                  90                  95

Tyr Cys Ala Lys Gly Gly Gly Thr Tyr Gly Tyr Trp Gly Gln Gly Thr
            100                 105                 110

Thr Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Ser Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
            435                 440                 445
```

<210> SEQ ID NO 23
<211> LENGTH: 216
<212> TYPE: PRT
<213> ORGANISM: Artificial Sequence
<220> FEATURE:
<223> OTHER INFORMATION: Synthetic: BCA7-2C5 (lambda)

<400> SEQUENCE: 23

-continued

```
Gln Ser Val Leu Thr Gln Pro Ala Ser Val Ser Gly Ser Pro Gly Gln
1               5                   10                  15

Ser Val Thr Ile Ser Cys Thr Gly Thr Ser Ser Ala His Gly Gly His
            20                  25                  30

Tyr Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Ser Tyr Thr Ser Ser
                85                  90                  95

Gly Ser Tyr Val Phe Gly Thr Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 24
<211> LENGTH: 121
<212> TYPE: PRT
<213> ORGANISM: Artificial Sequence
<220> FEATURE:
<223> OTHER INFORMATION: Synthetic: J6M0 GSK anti-BCMA Ab

<400> SEQUENCE: 24

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Tyr
            20                  25                  30

Trp Met His Trp Val Arg Gln Ala Pro Gly Gln Gly Leu Glu Trp Met
        35                  40                  45

Gly Ala Thr Tyr Arg Gly His Ser Asp Thr Tyr Tyr Asn Gln Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ala Ile Tyr Asp Gly Tyr Asp Val Leu Asp Asn Trp Gly
            100                 105                 110

Gln Gly Thr Leu Val Thr Val Ser Ser
        115                 120

<210> SEQ ID NO 25
<211> LENGTH: 107
```

-continued

```
<212> TYPE: PRT
<213> ORGANISM: Artificial Sequence
<220> FEATURE:
<223> OTHER INFORMATION: Synthetic: J6M0 GSK anti-BCMA Ab

<400> SEQUENCE: 25

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
                20                  25                  30

Leu Asn Trp Tyr Gln Gln Lys Pro Gly Lys Ala Pro Lys Leu Leu Ile
            35                  40                  45

Tyr Tyr Thr Ser Asn Leu His Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Arg Lys Leu Pro Trp
                85                  90                  95

Thr Phe Gly Gln Gly Thr Lys Leu Glu Ile Lys
            100                 105

<210> SEQ ID NO 26
<211> LENGTH: 117
<212> TYPE: PRT
<213> ORGANISM: Artificial Sequence
<220> FEATURE:
<223> OTHER INFORMATION: Synthetic: C11D5 BB anti-BCMA Ab

<400> SEQUENCE: 26

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
                20                  25                  30

Ser Ile Asn Trp Val Lys Arg Ala Pro Gly Lys Gly Leu Lys Trp Met
            35                  40                  45

Gly Trp Ile Asn Thr Glu Thr Arg Glu Pro Ala Tyr Ala Tyr Asp Phe
        50                  55                  60

Arg Gly Arg Phe Ala Phe Ser Leu Glu Thr Ser Ala Ser Thr Ala Tyr
65                  70                  75                  80

Leu Gln Ile Asn Asn Leu Lys Tyr Glu Asp Thr Ala Thr Tyr Phe Cys
                85                  90                  95

Ala Leu Asp Tyr Ser Tyr Ala Met Asp Tyr Trp Gly Gln Gly Thr Thr
            100                 105                 110

Leu Thr Val Ser Ser
        115

<210> SEQ ID NO 27
<211> LENGTH: 111
<212> TYPE: PRT
<213> ORGANISM: Artificial Sequence
<220> FEATURE:
<223> OTHER INFORMATION: Synthetic: C11D5 BB anti-BCMA Ab

<400> SEQUENCE: 27

Asp Ile Val Leu Thr Gln Ser Pro Ala Ser Leu Ala Met Ser Leu Gly
1               5                   10                  15

Lys Arg Ala Thr Ile Ser Cys Arg Ala Ser Glu Ser Val Ser Val Ile
                20                  25                  30

Gly Ala His Leu Ile His Trp Tyr Gln Gln Lys Pro Gly Gln Pro Pro
```

```
                35                  40                  45

Lys Leu Leu Ile Tyr Leu Ala Ser Asn Leu Glu Thr Gly Val Pro Ala
     50                  55                  60

Arg Phe Ser Gly Ser Gly Ser Gly Thr Asp Phe Thr Leu Thr Ile Asp
65                  70                  75                  80

Pro Val Glu Glu Asp Asp Val Ala Ile Tyr Ser Cys Leu Gln Ser Arg
                85                  90                  95

Ile Phe Pro Arg Thr Phe Gly Gly Gly Thr Lys Leu Glu Ile Lys
            100                 105                 110

<210> SEQ ID NO 28
<211> LENGTH: 8
<212> TYPE: PRT
<213> ORGANISM: Artificial Sequence
<220> FEATURE:
<223> OTHER INFORMATION: Synthetic: peptide

<400> SEQUENCE: 28

Glu Tyr Phe Asp Ser Leu Leu His
1               5

<210> SEQ ID NO 29
<211> LENGTH: 5
<212> TYPE: PRT
<213> ORGANISM: Artificial Sequence
<220> FEATURE:
<223> OTHER INFORMATION: Synthetic: BCA7 (VH  CDR1)

<400> SEQUENCE: 29

Thr Ala Trp Met Ser
1               5

<210> SEQ ID NO 30
<211> LENGTH: 19
<212> TYPE: PRT
<213> ORGANISM: Artificial Sequence
<220> FEATURE:
<223> OTHER INFORMATION: Synthetic: BCA7 (VH  CDR2)

<400> SEQUENCE: 30

Arg Ile Lys Ser Lys Ser Asp Gly Gly Thr Thr Asp Tyr Ala Ala Pro
1               5                   10                  15

Val Lys Gly

<210> SEQ ID NO 31
<211> LENGTH: 7
<212> TYPE: PRT
<213> ORGANISM: Artificial Sequence
<220> FEATURE:
<223> OTHER INFORMATION: Synthetic: BCA7 (VH  CDR3)

<400> SEQUENCE: 31

Gly Gly Gly Thr Tyr Gly Tyr
1               5

<210> SEQ ID NO 32
<211> LENGTH: 14
<212> TYPE: PRT
<213> ORGANISM: Artificial Sequence
<220> FEATURE:
<223> OTHER INFORMATION: Synthetic: BCA7 (VL  CDR1)

<400> SEQUENCE: 32

Thr Gly Thr Ser Ser Asp Val Gly Gly Tyr Asn Tyr Val Ser
```

```
1               5                10

<210> SEQ ID NO 33
<211> LENGTH: 7
<212> TYPE: PRT
<213> ORGANISM: Artificial Sequence
<220> FEATURE:
<223> OTHER INFORMATION: Synthetic: BCA7 (VL  CDR2)

<400> SEQUENCE: 33

Asp Val Ser Asn Arg Pro Ser
1               5

<210> SEQ ID NO 34
<211> LENGTH: 10
<212> TYPE: PRT
<213> ORGANISM: Artificial Sequence
<220> FEATURE:
<223> OTHER INFORMATION: Synthetic: BCA7 (VL  CDR3)

<400> SEQUENCE: 34

Gly Ser Tyr Thr Ser Ser Gly Ser Tyr Val
1               5                10

<210> SEQ ID NO 35
<211> LENGTH: 5
<212> TYPE: PRT
<213> ORGANISM: Artificial Sequence
<220> FEATURE:
<223> OTHER INFORMATION: Synthetic: BC4C9 (VH  CDR1)

<400> SEQUENCE: 35

Ser Tyr Asp Ile Asn
1               5

<210> SEQ ID NO 36
<211> LENGTH: 17
<212> TYPE: PRT
<213> ORGANISM: Artificial Sequence
<220> FEATURE:
<223> OTHER INFORMATION: Synthetic: BC4C9 (VH  CDR2)

<400> SEQUENCE: 36

Trp Met Asn Pro Asn Ser Gly Asn Thr Gly Tyr Ala Gln Lys Phe Gln
1               5                10               15

Gly

<210> SEQ ID NO 37
<211> LENGTH: 4
<212> TYPE: PRT
<213> ORGANISM: Artificial Sequence
<220> FEATURE:
<223> OTHER INFORMATION: Synthetic: BC4C9 (VH  CDR3)

<400> SEQUENCE: 37

Gly Leu Gly Glu
1

<210> SEQ ID NO 38
<211> LENGTH: 14
<212> TYPE: PRT
<213> ORGANISM: Artificial Sequence
<220> FEATURE:
<223> OTHER INFORMATION: Synthetic: BC4C9 (VL  CDR1)

<400> SEQUENCE: 38
```

-continued

```
Thr Gly Thr Ser Ser Asp Val Gly Gly Tyr Asn Tyr Val Ser
1               5                   10

<210> SEQ ID NO 39
<211> LENGTH: 7
<212> TYPE: PRT
<213> ORGANISM: Artificial Sequence
<220> FEATURE:
<223> OTHER INFORMATION: Synthetic: BC4C9 (VL  CDR2)

<400> SEQUENCE: 39

Asp Val Ser Lys Arg Pro Ser
1               5

<210> SEQ ID NO 40
<211> LENGTH: 11
<212> TYPE: PRT
<213> ORGANISM: Artificial Sequence
<220> FEATURE:
<223> OTHER INFORMATION: Synthetic: BC4C9 (VL  CDR3)

<400> SEQUENCE: 40

Ile Ser Tyr Ser Ser Ser Ser Thr Phe Tyr Val
1               5                   10

<210> SEQ ID NO 41
<211> LENGTH: 5
<212> TYPE: PRT
<213> ORGANISM: Artificial Sequence
<220> FEATURE:
<223> OTHER INFORMATION: Synthetic: BC5C4 (VH  CDR1)

<400> SEQUENCE: 41

Asp Tyr Ala Met His
1               5

<210> SEQ ID NO 42
<211> LENGTH: 17
<212> TYPE: PRT
<213> ORGANISM: Artificial Sequence
<220> FEATURE:
<223> OTHER INFORMATION: Synthetic: BC5C4 (VH  CDR2)

<400> SEQUENCE: 42

Gly Ile Ser Trp Asn Ser Gly Ser Ile Gly Tyr Ala Asp Ser Val Lys
1               5                   10                  15

Gly

<210> SEQ ID NO 43
<211> LENGTH: 8
<212> TYPE: PRT
<213> ORGANISM: Artificial Sequence
<220> FEATURE:
<223> OTHER INFORMATION: Synthetic: BC5C4 (VH  CDR3)

<400> SEQUENCE: 43

Ile Asp Asn Val Ala Phe His Ser
1               5

<210> SEQ ID NO 44
<211> LENGTH: 14
<212> TYPE: PRT
<213> ORGANISM: Artificial Sequence
<220> FEATURE:
<223> OTHER INFORMATION: Synthetic: BC5C4 (VL  CDR1)

<400> SEQUENCE: 44
```

-continued

Thr Gly Thr Ser Ser Asp Ile Gly Gly Tyr Asn Tyr Val Ser
1               5               10

<210> SEQ ID NO 45
<211> LENGTH: 7
<212> TYPE: PRT
<213> ORGANISM: Artificial Sequence
<220> FEATURE:
<223> OTHER INFORMATION: Synthetic: BC5C4 (VL  CDR2)

<400> SEQUENCE: 45

Glu Val Ser Asn Arg Pro Ser
1               5

<210> SEQ ID NO 46
<211> LENGTH: 7
<212> TYPE: PRT
<213> ORGANISM: Artificial Sequence
<220> FEATURE:
<223> OTHER INFORMATION: Synthetic: BC5C4 (VL  CDR3)

<400> SEQUENCE: 46

Glu Val Ser Asn Arg Pro Ser
1               5

<210> SEQ ID NO 47
<211> LENGTH: 7
<212> TYPE: PRT
<213> ORGANISM: Artificial Sequence
<220> FEATURE:
<223> OTHER INFORMATION: Synthetic: BC6G8 (VH  CDR1)

<400> SEQUENCE: 47

Ser Asn Ser Val Gly Trp His
1               5

<210> SEQ ID NO 48
<211> LENGTH: 18
<212> TYPE: PRT
<213> ORGANISM: Artificial Sequence
<220> FEATURE:
<223> OTHER INFORMATION: Synthetic: BC6G8 (VH  CDR2)

<400> SEQUENCE: 48

Arg Thr Tyr Tyr Arg Ser Asn Phe Ala Thr Asp Tyr Ala Ala Ser Val
1               5               10              15

Arg Gly

<210> SEQ ID NO 49
<211> LENGTH: 8
<212> TYPE: PRT
<213> ORGANISM: Artificial Sequence
<220> FEATURE:
<223> OTHER INFORMATION: Synthetic: BC6G8 (VH  CDR3)

<400> SEQUENCE: 49

Asp Trp Tyr Gly Val Tyr Asp Phe
1               5

<210> SEQ ID NO 50
<211> LENGTH: 11
<212> TYPE: PRT
<213> ORGANISM: Artificial Sequence
<220> FEATURE:
<223> OTHER INFORMATION: Synthetic: BC6G8 (VL  CDR1)

<400> SEQUENCE: 50

Gly Gly Asn Asn Ile Gly Ser Lys Ser Val His
1               5                   10

<210> SEQ ID NO 51
<211> LENGTH: 7
<212> TYPE: PRT
<213> ORGANISM: Artificial Sequence
<220> FEATURE:
<223> OTHER INFORMATION: Synthetic: BC6G8 (VL  CDR2)

<400> SEQUENCE: 51

Tyr Asp Ser Asp Arg Pro Ser
1               5

<210> SEQ ID NO 52
<211> LENGTH: 12
<212> TYPE: PRT
<213> ORGANISM: Artificial Sequence
<220> FEATURE:
<223> OTHER INFORMATION: Synthetic: BC6G8 (VL  CDR3)

<400> SEQUENCE: 52

Gln Val Trp Asp Ser Ser Ser Asp His Leu Val Val
1               5                   10

<210> SEQ ID NO 53
<211> LENGTH: 5
<212> TYPE: PRT
<213> ORGANISM: Artificial Sequence
<220> FEATURE:
<223> OTHER INFORMATION: Synthetic: BCA7-2C5 (VH  CDR1)

<400> SEQUENCE: 53

Thr Ala Trp Met Ser
1               5

<210> SEQ ID NO 54
<211> LENGTH: 19
<212> TYPE: PRT
<213> ORGANISM: Artificial Sequence
<220> FEATURE:
<223> OTHER INFORMATION: Synthetic: BCA7-2C5 (VH  CDR2)

<400> SEQUENCE: 54

Arg Ile Lys Ser Lys Ser Asp Gly Gly Thr Thr Asp Tyr Ala Ala Pro
1               5                   10                  15

Val Lys Gly

<210> SEQ ID NO 55
<211> LENGTH: 7
<212> TYPE: PRT
<213> ORGANISM: Artificial Sequence
<220> FEATURE:
<223> OTHER INFORMATION: Synthetic: BCA7-2C5 (VH  CDR3)

<400> SEQUENCE: 55

Gly Gly Gly Thr Tyr Gly Tyr
1               5

<210> SEQ ID NO 56
<211> LENGTH: 14
<212> TYPE: PRT
<213> ORGANISM: Artificial Sequence
<220> FEATURE:
<223> OTHER INFORMATION: Synthetic: BCA7-2C5 (VL  CDR1)

<400> SEQUENCE: 56

Thr Gly Thr Ser Ser Ala His Gly Gly His Tyr Tyr Val Ser
1               5                   10

<210> SEQ ID NO 57
<211> LENGTH: 7
<212> TYPE: PRT
<213> ORGANISM: Artificial Sequence
<220> FEATURE:
<223> OTHER INFORMATION: Synthetic: BCA7-2C5 (VL  CDR2)

<400> SEQUENCE: 57

Asp Val Ser Asn Arg Pro Ser
1               5

<210> SEQ ID NO 58
<211> LENGTH: 10
<212> TYPE: PRT
<213> ORGANISM: Artificial Sequence
<220> FEATURE:
<223> OTHER INFORMATION: Synthetic: BCA7-2C5 (VL  CDR3)

<400> SEQUENCE: 58

Gly Ser Tyr Thr Ser Ser Gly Ser Tyr Val
1               5                   10

<210> SEQ ID NO 59
<211> LENGTH: 5
<212> TYPE: PRT
<213> ORGANISM: Artificial Sequence
<220> FEATURE:
<223> OTHER INFORMATION: Synthetic: BCA7-2E1 (VH  CDR1)

<400> SEQUENCE: 59

Thr Ala Trp Met Ser
1               5

<210> SEQ ID NO 60
<211> LENGTH: 19
<212> TYPE: PRT
<213> ORGANISM: Artificial Sequence
<220> FEATURE:
<223> OTHER INFORMATION: Synthetic: BCA7-2E1 (VH  CDR2)

<400> SEQUENCE: 60

Arg Ile Lys Ser Lys Ser Asp Gly Gly Thr Thr Asp Tyr Ala Ala Pro
1               5                   10                  15

Val Lys Gly

<210> SEQ ID NO 61
<211> LENGTH: 7
<212> TYPE: PRT
<213> ORGANISM: Artificial Sequence
<220> FEATURE:
<223> OTHER INFORMATION: Synthetic: BCA7-2E1 (VH  CDR3)

<400> SEQUENCE: 61

Gly Gly Gly Thr Tyr Gly Tyr
1               5

<210> SEQ ID NO 62
<211> LENGTH: 14
<212> TYPE: PRT
<213> ORGANISM: Artificial Sequence
<220> FEATURE:

<223> OTHER INFORMATION: Synthetic: BCA7-2E1 (VL  CDR1)

<400> SEQUENCE: 62

Thr Gly Thr Ser Ser Asp Gly Gly Gly His Thr Tyr Val Ser
1               5                   10

<210> SEQ ID NO 63
<211> LENGTH: 7
<212> TYPE: PRT
<213> ORGANISM: Artificial Sequence
<220> FEATURE:
<223> OTHER INFORMATION: Synthetic: BCA7-2E1 (VL  CDR2)

<400> SEQUENCE: 63

Asp Val Ser Asn Arg Pro Ser
1               5

<210> SEQ ID NO 64
<211> LENGTH: 10
<212> TYPE: PRT
<213> ORGANISM: Artificial Sequence
<220> FEATURE:
<223> OTHER INFORMATION: Synthetic: BCA7-2E1 (VL  CDR3)

<400> SEQUENCE: 64

Gly Ser Tyr Thr Ser Ser Gly Ser Tyr Val
1               5                   10

<210> SEQ ID NO 65
<211> LENGTH: 5
<212> TYPE: PRT
<213> ORGANISM: Artificial Sequence
<220> FEATURE:
<223> OTHER INFORMATION: Synthetic: BCA7-2D11 (VH  CDR1)

<400> SEQUENCE: 65

Thr Ala Trp Met Ser
1               5

<210> SEQ ID NO 66
<211> LENGTH: 19
<212> TYPE: PRT
<213> ORGANISM: Artificial Sequence
<220> FEATURE:
<223> OTHER INFORMATION: Synthetic: BCA7-2D11 (VH  CDR2)

<400> SEQUENCE: 66

Arg Ile Lys Ser Lys Ser Asp Gly Gly Thr Thr Asp Tyr Ala Ala Pro
1               5                   10                  15

Val Lys Gly

<210> SEQ ID NO 67
<211> LENGTH: 7
<212> TYPE: PRT
<213> ORGANISM: Artificial Sequence
<220> FEATURE:
<223> OTHER INFORMATION: Synthetic: BCA7-2D11 (VH  CDR3)

<400> SEQUENCE: 67

Gly Gly Gly Thr Tyr Gly Tyr
1               5

<210> SEQ ID NO 68
<211> LENGTH: 14
<212> TYPE: PRT
<213> ORGANISM: Artificial Sequence

```
<220> FEATURE:
<223> OTHER INFORMATION: Synthetic: BCA7-2D11 (VL  CDR1)

<400> SEQUENCE: 68

Thr Gly Thr Ser Ser Val Val Gly Gly His Asp Tyr Val Ser
1               5                   10

<210> SEQ ID NO 69
<211> LENGTH: 7
<212> TYPE: PRT
<213> ORGANISM: Artificial Sequence
<220> FEATURE:
<223> OTHER INFORMATION: Synthetic: BCA7-2D11 (VL  CDR2)

<400> SEQUENCE: 69

Asp Val Ser Asn Arg Pro Ser
1               5

<210> SEQ ID NO 70
<211> LENGTH: 10
<212> TYPE: PRT
<213> ORGANISM: Artificial Sequence
<220> FEATURE:
<223> OTHER INFORMATION: Synthetic: BCA7-2D11 (VL  CDR3)

<400> SEQUENCE: 70

Gly Ser Tyr Thr Ser Ser Gly Ser Tyr Val
1               5                   10

<210> SEQ ID NO 71
<211> LENGTH: 5
<212> TYPE: PRT
<213> ORGANISM: Artificial Sequence
<220> FEATURE:
<223> OTHER INFORMATION: Synthetic: BCA7-2G2 (VH  CDR1)

<400> SEQUENCE: 71

Thr Ala Trp Met Ser
1               5

<210> SEQ ID NO 72
<211> LENGTH: 19
<212> TYPE: PRT
<213> ORGANISM: Artificial Sequence
<220> FEATURE:
<223> OTHER INFORMATION: Synthetic: BCA7-2G2 (VH  CDR2)

<400> SEQUENCE: 72

Arg Ile Lys Ser Lys Ser Asp Gly Gly Thr Thr Asp Tyr Ala Ala Pro
1               5                   10                  15

Val Lys Gly

<210> SEQ ID NO 73
<211> LENGTH: 7
<212> TYPE: PRT
<213> ORGANISM: Artificial Sequence
<220> FEATURE:
<223> OTHER INFORMATION: Synthetic: BCA7-2G2 (VH  CDR3)

<400> SEQUENCE: 73

Gly Gly Gly Thr Tyr Gly Tyr
1               5

<210> SEQ ID NO 74
<211> LENGTH: 14
<212> TYPE: PRT
```

-continued

<213> ORGANISM: Artificial Sequence
<220> FEATURE:
<223> OTHER INFORMATION: Synthetic: BCA7-2G2 (VL  CDR1)

<400> SEQUENCE: 74

Thr Gly Thr Ser Ser Ser Val Gly Gly Arg Gln Tyr Val Ser
1               5                   10

<210> SEQ ID NO 75
<211> LENGTH: 7
<212> TYPE: PRT
<213> ORGANISM: Artificial Sequence
<220> FEATURE:
<223> OTHER INFORMATION: Synthetic: BCA7-2G2 (VL  CDR2)

<400> SEQUENCE: 75

Asp Val Ser Asn Arg Pro Ser
1               5

<210> SEQ ID NO 76
<211> LENGTH: 10
<212> TYPE: PRT
<213> ORGANISM: Artificial Sequence
<220> FEATURE:
<223> OTHER INFORMATION: Synthetic: BCA7-2G2 (VL  CDR3)

<400> SEQUENCE: 76

Gly Ser Tyr Thr Ser Ser Gly Ser Tyr Val
1               5                   10

<210> SEQ ID NO 77
<211> LENGTH: 5
<212> TYPE: PRT
<213> ORGANISM: Artificial Sequence
<220> FEATURE:
<223> OTHER INFORMATION: Synthetic: BCA7-2D8 (VH  CDR1)

<400> SEQUENCE: 77

Thr Ala Trp Met Ser
1               5

<210> SEQ ID NO 78
<211> LENGTH: 19
<212> TYPE: PRT
<213> ORGANISM: Artificial Sequence
<220> FEATURE:
<223> OTHER INFORMATION: Synthetic: BCA7-2D8 (VH  CDR2)

<400> SEQUENCE: 78

Arg Ile Lys Ser Lys Ser Asp Gly Gly Thr Thr Asp Tyr Ala Ala Pro
1               5                   10                  15

Val Lys Gly

<210> SEQ ID NO 79
<211> LENGTH: 7
<212> TYPE: PRT
<213> ORGANISM: Artificial Sequence
<220> FEATURE:
<223> OTHER INFORMATION: Synthetic: BCA7-2D8 (VH  CDR3)

<400> SEQUENCE: 79

Gly Gly Gly Thr Tyr Gly Tyr
1               5

<210> SEQ ID NO 80
<211> LENGTH: 14

```
<212> TYPE: PRT
<213> ORGANISM: Artificial Sequence
<220> FEATURE:
<223> OTHER INFORMATION: Synthetic: BCA7-2D8 (VL  CDR1)

<400> SEQUENCE: 80

Thr Gly Thr Ser Ser Ser Ile Gly Asp Ser Tyr Tyr Val Ser
1               5                   10

<210> SEQ ID NO 81
<211> LENGTH: 7
<212> TYPE: PRT
<213> ORGANISM: Artificial Sequence
<220> FEATURE:
<223> OTHER INFORMATION: Synthetic: BCA7-2D8 (VL  CDR2)

<400> SEQUENCE: 81

Asp Val Ser Asn Arg Pro Ser
1               5

<210> SEQ ID NO 82
<211> LENGTH: 10
<212> TYPE: PRT
<213> ORGANISM: Artificial Sequence
<220> FEATURE:
<223> OTHER INFORMATION: Synthetic: BCA7-2D8 (VL  CDR3)

<400> SEQUENCE: 82

Gly Ser Tyr Thr Ser Ser Gly Ser Tyr Val
1               5                   10

<210> SEQ ID NO 83
<211> LENGTH: 5
<212> TYPE: PRT
<213> ORGANISM: Artificial Sequence
<220> FEATURE:
<223> OTHER INFORMATION: Synthetic: BCA7-2E8 (VH  CDR1)

<400> SEQUENCE: 83

Thr Ala Trp Met Ser
1               5

<210> SEQ ID NO 84
<211> LENGTH: 19
<212> TYPE: PRT
<213> ORGANISM: Artificial Sequence
<220> FEATURE:
<223> OTHER INFORMATION: Synthetic: BCA7-2E8 (VH  CDR2)

<400> SEQUENCE: 84

Arg Ile Lys Ser Lys Ser Asp Gly Gly Thr Thr Asp Tyr Ala Ala Pro
1               5                   10                  15

Val Lys Gly

<210> SEQ ID NO 85
<211> LENGTH: 7
<212> TYPE: PRT
<213> ORGANISM: Artificial Sequence
<220> FEATURE:
<223> OTHER INFORMATION: Synthetic: BCA7-2E8 (VH  CDR3)

<400> SEQUENCE: 85

Gly Gly Gly Thr Tyr Gly Tyr
1               5

<210> SEQ ID NO 86
```

```
<211> LENGTH: 14
<212> TYPE: PRT
<213> ORGANISM: Artificial Sequence
<220> FEATURE:
<223> OTHER INFORMATION: Synthetic: BCA7-2E8 (VL  CDR1)

<400> SEQUENCE: 86

Thr Gly Thr Ser Ser Asp Val Gly Gly Tyr Asn Tyr Val Ser
1               5                   10

<210> SEQ ID NO 87
<211> LENGTH: 7
<212> TYPE: PRT
<213> ORGANISM: Artificial Sequence
<220> FEATURE:
<223> OTHER INFORMATION: Synthetic: BCA7-2E8 (VL  CDR2)

<400> SEQUENCE: 87

Asp Val Ser Asn Arg Pro Ser
1               5

<210> SEQ ID NO 88
<211> LENGTH: 10
<212> TYPE: PRT
<213> ORGANISM: Artificial Sequence
<220> FEATURE:
<223> OTHER INFORMATION: Synthetic: BCA7-2E8 (VL  CDR3)

<400> SEQUENCE: 88

Gly Ser Leu Arg Ser Asn Gly Asp Tyr Val
1               5                   10

<210> SEQ ID NO 89
<211> LENGTH: 14
<212> TYPE: PRT
<213> ORGANISM: Artificial Sequence
<220> FEATURE:
<223> OTHER INFORMATION: Synthetic: BCA7-2C5 (VL lambda  CDR1)

<400> SEQUENCE: 89

Thr Gly Thr Ser Ser Ala His Gly Gly His Tyr Tyr Val Ser
1               5                   10

<210> SEQ ID NO 90
<211> LENGTH: 7
<212> TYPE: PRT
<213> ORGANISM: Artificial Sequence
<220> FEATURE:
<223> OTHER INFORMATION: Synthetic: BCA7-2C5 (VL lambda  CDR2)

<400> SEQUENCE: 90

Asp Val Ser Asn Arg Pro Ser
1               5

<210> SEQ ID NO 91
<211> LENGTH: 10
<212> TYPE: PRT
<213> ORGANISM: Artificial Sequence
<220> FEATURE:
<223> OTHER INFORMATION: Synthetic: BCA7-2C5 (VL lambda  CDR3)

<400> SEQUENCE: 91

Gly Ser Tyr Thr Ser Ser Gly Ser Tyr Val
1               5                   10

<210> SEQ ID NO 92
<211> LENGTH: 184
```

-continued

```
<212> TYPE: PRT
<213> ORGANISM: Homo sapiens
<220> FEATURE:
<221> NAME/KEY: misc_feature
<223> OTHER INFORMATION: Wild type Human BCMA protein

<400> SEQUENCE: 92

Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
            20                  25                  30

Pro Pro Leu Thr Cys Gln Arg Tyr Cys Asn Ala Ser Val Thr Asn Ser
        35                  40                  45

Val Lys Gly Thr Asn Ala Ile Leu Trp Thr Cys Leu Gly Leu Ser Leu
    50                  55                  60

Ile Ile Ser Leu Ala Val Phe Val Leu Met Phe Leu Leu Arg Lys Ile
65                  70                  75                  80

Asn Ser Glu Pro Leu Lys Asp Glu Phe Lys Asn Thr Gly Ser Gly Leu
                85                  90                  95

Leu Gly Met Ala Asn Ile Asp Leu Glu Lys Ser Arg Thr Gly Asp Glu
            100                 105                 110

Ile Ile Leu Pro Arg Gly Leu Glu Tyr Thr Val Glu Glu Cys Thr Cys
        115                 120                 125

Glu Asp Cys Ile Lys Ser Lys Pro Lys Val Asp Ser Asp His Cys Phe
    130                 135                 140

Pro Leu Pro Ala Met Glu Glu Gly Ala Thr Ile Leu Val Thr Thr Lys
145                 150                 155                 160

Thr Asn Asp Tyr Cys Lys Ser Leu Pro Ala Ala Leu Ser Ala Thr Glu
                165                 170                 175

Ile Glu Lys Ser Ile Ser Ala Arg
                180
```

ANTIGEN BINDING PROTEINS THAT BIND BCMA

CROSS-REFERENCE TO RELATED APPLICATIONS

This application is a continuation of International Patent Application No. PCT/US2020/019763, filed Feb. 25, 2020, which claims the benefit of priority under 35 U.S.C. § 119 to U.S. provisional application No. 62/810,771, filed Feb. 26, 2019, and U.S. provisional application No. 62/811,431, filed Feb. 27, 2019. The disclosures of all of the aforementioned applications are incorporated by reference in their entireties.

Throughout this application various publications, patents, and/or patent applications are referenced. The disclosures of the publications, patents and/or patent applications are hereby incorporated by reference in their entireties into this application in order to more fully describe the state of the art to which this disclosure pertains.

SEQUENCE LISTING

The present application is filed with a Sequence Listing in electronic format. The Sequence Listing is provided as a file entitled "2020-02-25_01223-0011-00PCT_ST25_updated" created on Feb. 25, 2020, which is 51,361 bytes in size. The information in the electronic format of the sequence listing is incorporated herein by reference in its entirety.

TECHNICAL FIELD

The present disclosure provides antigen binding proteins that bind specifically to B Cell Maturation Antigen (BCMA) and nucleic acids that encode the antigen binding proteins, vectors comprising the nucleic acids, host cells harboring the vectors, and method of use thereof.

BACKGROUND

B Cell Maturation Antigen (BCMA), also known as TNFRSF17 and CD269 (UniProt Q02223), is a member of the tumor necrosis receptor superfamily. BCMA is a non-glycosylated type III transmembrane protein that is expressed on differentiated plasma cells (Laabi et al., 1992 The EMBO Journal 11(11):3897-3904; Laabi et al., 1994 Nucleic Acids Research 22(7):1147-1154; Madry et al., 1998 International Immunology 10(11):1693-1702) and is a cell surface receptor that is involved in B cell development and survival.

BCMA is a cell surface receptor for two ligands of the TNF superfamily, APRIL (A PRoliferation-Inducing Ligand) and BAFF. APRIL and BAFF are high and low affinity ligands to BCMA, respectively. APRIL is a proliferation-inducing ligand and BAFF is a B lymphocyte stimulator. TACI is a negative regulator that binds APRIL and BAFF. The coordinated binding of APRIL and BAFF to BCMA and/or TACI induces transcription of factor NF-κB and increases expression of pro-survival Bcl-2 family members and down regulates expression of pro-apoptotic factors which promotes survival and inhibits apoptosis. This complex interaction promotes B cell differentiation, proliferation, survival and antibody production (Rickert 2011 Immunology Review 244(1):115-133). BCMA is known to support growth and survival of malignant human B cells, and upregulated expression of BCMA and TACI has been reported in malignant human B cells including multiple myeloma (MM) cells (see review in "BAFF and APRIL: a tutorial on B cell survival" by Mackay et al., 2004 Annual Review Immunology 21:231-264). Additionally, BCMA, APRIL and BAFF signaling have been reported to activate NFκB in B cell neoplasms and multiple myeloma.

Multiple myeloma is a clonal B-cell lymphoma that develops in multiple sites in the bone marrow then spreads through circulation. BCMA is expressed at significantly higher levels in multiple myeloma cells compared to normal tissues, making BCMA a good target antigen for immunotherapy. Thus, BCMA is an attractive antigen for targeting with antibodies. The present disclosure provides BCMA binding proteins, particularly anti-BCMA antibodies or antigen-binding portions thereof, that specifically bind BCMA, and uses thereof.

SUMMARY

The present disclosure provides a fully human anti-BCMA antibody, or an antigen-binding fragment thereof, comprising a heavy chain and a light chain, wherein (a) the heavy chain comprises: a heavy chain complementarity determining region 1 (CDR1) having the amino acid sequence of SEQ ID NO:29, a heavy chain CDR2 having the amino acid sequence of SEQ ID NO:30, a heavy chain CDR3 having the amino acid sequence of SEQ ID NO:31; and the light chain comprises: a light chain CDR1 having the amino acid sequence of SEQ ID NO:32, a light chain CDR2 having the amino acid sequence of SEQ ID NO:33, and a light chain CDR3 having the amino acid sequence of SEQ ID NO:34; wherein (b) the heavy chain comprises: a heavy chain CDR1 having the amino acid sequence of SEQ ID NO:35, a heavy chain CDR2 having the amino acid sequence of SEQ ID NO:36, a heavy chain CDR3 having the amino acid sequence of SEQ ID NO:37; and the light chain comprises: a light chain CDR1 having the amino acid sequence of SEQ ID NO:38, a light chain CDR2 having the amino acid sequence of SEQ ID NO:39, and a light chain CDR3 having the amino acid sequence of SEQ ID NO:40; wherein (c) the heavy chain comprises: a heavy chain CDR1 having the amino acid sequence of SEQ ID NO:41, a heavy chain CDR2 having the amino acid sequence of SEQ ID NO:42, a heavy chain CDR3 having the amino acid sequence of SEQ ID NO:43; and the light chain comprises: a light chain CDR1 having the amino acid sequence of SEQ ID NO:44, a light chain CDR2 having the amino acid sequence of SEQ ID NO:45, and a light chain CDR3 having the amino acid sequence of SEQ ID NO:46; wherein (d) the heavy chain comprises: a heavy chain CDR1 having the amino acid sequence of SEQ ID NO:47, a heavy chain CDR2 having the amino acid sequence of SEQ ID NO:48, a heavy chain CDR3 having the amino acid sequence of SEQ ID NO:49; and the light chain comprises: a light chain CDR1 having the amino acid sequence of SEQ ID NO:50, a light chain CDR2 having the amino acid sequence of SEQ ID NO:51, and a light chain CDR3 having the amino acid sequence of SEQ ID NO:52; wherein (e) the heavy chain comprises: a heavy chain CDR1 having the amino acid sequence of SEQ ID NO:53, a heavy chain CDR2 having the amino acid sequence of SEQ ID NO:54, a heavy chain CDR3 having the amino acid sequence of SEQ ID NO:55; and the light chain comprises: a light chain CDR1 having the amino acid sequence of SEQ ID NO:56, a light chain CDR2 having the amino acid sequence of SEQ ID NO:57, and a light chain CDR3 having the amino acid sequence of SEQ ID NO:58; wherein (f) the heavy chain comprises: a heavy chain CDR1 having the amino acid sequence of SEQ ID NO:59, a heavy chain CDR2 having the amino acid sequence of SEQ ID NO:60, a heavy chain CDR3 having the amino acid sequence of SEQ ID NO:61; and the light chain comprises: a light chain CDR1 having the amino acid sequence of SEQ ID NO:62, a light chain CDR2 having the amino acid sequence of SEQ ID NO:63, and a light chain CDR3 having the amino acid sequence of SEQ ID NO:64; wherein (g) the heavy chain comprises: a heavy chain CDR1 having the amino acid sequence of SEQ ID NO:65, a heavy chain CDR2 having the amino acid sequence of SEQ ID NO:66, a heavy chain CDR3 having the amino acid sequence of SEQ ID NO:67; and the light chain comprises: a light chain CDR1 having the amino acid sequence of SEQ ID NO:68, a light chain CDR2 having the amino acid sequence of SEQ ID NO:69, and a light chain CDR3 having the amino acid sequence of SEQ ID NO:70; wherein (h) the heavy chain comprises: a heavy chain CDR1 having the amino acid sequence of SEQ ID NO:71, a heavy chain CDR2 having the amino acid sequence of SEQ ID NO:72, a heavy chain CDR3 having the amino acid sequence of SEQ ID NO:73; and the light chain comprises: a light chain CDR1 having the amino acid sequence of SEQ ID NO:74, a light chain CDR2 having the amino acid sequence of SEQ ID NO:75, and a light chain CDR3 having the amino acid sequence of SEQ ID NO:76; wherein (i) the heavy chain comprises: a heavy chain CDR1 having the amino acid sequence of SEQ ID NO:77, a heavy chain CDR2 having the amino acid sequence of SEQ ID NO:78, a heavy chain CDR3 having the amino acid sequence of SEQ ID NO:79; and the light chain comprises: a light chain CDR1 having the amino acid sequence of SEQ ID NO:80, a light chain CDR2 having the amino acid sequence of SEQ ID NO:81, and a light chain CDR3 having the amino acid sequence of SEQ ID NO:82; wherein (j) the heavy chain comprises: a heavy chain CDR1 having the amino acid sequence of SEQ ID NO:83, a heavy chain CDR2 having the amino acid sequence of SEQ ID NO:84, a heavy chain CDR3 having the amino acid sequence of SEQ ID NO:85; and the light chain comprises: a light chain CDR1 having the amino acid sequence of SEQ ID NO:86, a light chain CDR2 having the amino acid sequence of SEQ ID NO:87, and a light chain CDR3 having the amino acid sequence of SEQ ID NO:88; or wherein (k) the heavy chain comprises: a heavy chain CDR1 having the amino acid sequence of SEQ ID NO:53, a heavy chain CDR2 having the amino acid sequence of SEQ ID NO:54, a heavy chain CDR3 having the amino acid sequence of SEQ ID NO:55; and the light chain comprises: a lambda light chain CDR1 having the amino acid sequence of SEQ ID NO:89, a lambda light chain CDR2 having the amino acid sequence of SEQ ID NO:90, and a lambda light chain CDR3 having the amino acid sequence of SEQ ID NO:91.

The present disclosure provides a fully human anti-BCMA antibody, or an antigen-binding fragment thereof, comprising a heavy chain and a light chain, the heavy chain comprising a heavy chain variable region having at least 95% sequence identity to the amino acid sequence of SEQ ID NO: 8, 10, 12, 14 or 22; and the light chain comprising a light chain variable region having at least 95% sequence identity to the amino acid sequence of SEQ ID NO: 9, 11, 13, 15, 16, 17, 18, 19, 20, 21 or 23.

The present disclosure provides a fully human anti-BCMA antibody, or the antigen-binding fragment thereof, comprising a heavy chain variable region and a light chain variable region, wherein the heavy chain variable region and the light chain variable region comprise the amino acid sequences of SEQ ID NOS:8 and 9 (e.g., herein called BCA7); SEQ ID NOS:10 and 11 (e.g., herein called BC4C9); SEQ ID NOS:12 and 13 (e.g., herein called CD5C4); SEQ ID NOS:14 and 15 (e.g., herein called BC6G8); SEQ ID NOS:8 and 16 (e.g., herein called BCA7-2C5); SEQ ID NOS:8 and 17 (e.g., herein called BCA7-2E1); SEQ ID NOS:8 and 18 (e.g., herein called BCA7-2D11); SEQ ID NOS:8 and 19 (e.g., herein called BCA7-2G2); SEQ ID NOS:8 and 20 (e.g., herein called BCA7-2D8); SEQ ID NOS:8 and 21 (e.g., herein called BCA7-2E8); or SEQ ID NOS:22 and 23 (e.g., herein called BCA7-2C5 with lambda light chain).

The present disclosure provides a fully human anti-BCMA antibody, or the antigen-binding fragment thereof, wherein the antigen-binding fragment is a Fab fragment comprising a variable domain region from a heavy chain and a variable domain region from a light chain, wherein (a) the variable domain region from the heavy chain comprises: a heavy chain complementarity determining region 1 (CDR1) having the amino acid sequence of SEQ ID NO:29, a heavy chain CDR2 having the amino acid sequence of SEQ ID NO:30, a heavy chain CDR3 having the amino acid sequence of SEQ ID NO:31; and the variable domain region from the light chain comprises: a light chain CDR1 having the amino acid sequence of SEQ ID NO:32, a light chain CDR2 having the amino acid sequence of SEQ ID NO:33, and a light chain CDR3 having the amino acid sequence of SEQ ID NO:34; wherein (b) the variable domain region from the heavy chain comprises: a heavy chain CDR1 having the amino acid sequence of SEQ ID NO:35, a heavy chain CDR2 having the amino acid sequence of SEQ ID NO:36, a heavy chain CDR3 having the amino acid sequence of SEQ ID NO:37; and the variable domain region from the light chain comprises: a light chain CDR1 having the amino acid sequence of SEQ ID NO:38, a light chain CDR2 having the amino acid sequence of SEQ ID NO:39, and a light chain CDR3 having the amino acid sequence of SEQ ID NO:40; wherein (c) the variable domain region from the heavy chain comprises: a heavy chain CDR1 having the amino acid sequence of SEQ ID NO:41, a heavy chain CDR2 having the amino acid sequence of SEQ ID NO:42, a heavy chain CDR3 having the amino acid sequence of SEQ ID NO:43; and the variable domain region from the light chain comprises: a light chain CDR1 having the amino acid sequence of SEQ ID NO:44, a light chain CDR2 having the amino acid sequence of SEQ ID NO:45, and a light chain CDR3 having the amino acid sequence of SEQ ID NO:46; wherein (d) the variable domain region from the heavy chain comprises: a heavy chain CDR1 having the amino acid sequence of SEQ ID NO:47, a heavy chain CDR2 having the amino acid sequence of SEQ ID NO:48, a heavy chain CDR3 having the amino acid sequence of SEQ ID NO:49; and the variable domain region from the light chain comprises: a light chain CDR1 having the amino acid sequence of SEQ ID NO:50, a light chain CDR2 having the amino acid sequence of SEQ ID NO:51, and a light chain CDR3 having the amino acid sequence of SEQ ID NO:52; wherein (e) the variable domain region from the heavy chain comprises: a heavy chain CDR1 having the amino acid sequence of SEQ ID NO:53, a heavy chain CDR2 having the amino acid sequence of SEQ ID NO:54, a heavy chain CDR3 having the amino acid sequence of SEQ ID NO:55; and the variable domain region from the light chain comprises: a light chain CDR1 having the amino acid sequence of SEQ ID NO:56, a light chain CDR2 having the amino acid sequence of SEQ ID NO:57, and a light chain CDR3 having the amino acid sequence of SEQ ID NO:58; wherein (f) the variable domain region from the heavy chain comprises: a heavy chain CDR1 having the amino acid sequence of SEQ ID NO:59, a heavy chain CDR2 having the amino acid sequence of SEQ ID NO:60, a heavy chain CDR3 having the amino acid sequence of SEQ ID NO:61; and the variable domain region from the light chain comprises: a light chain CDR1 having the amino acid sequence of SEQ ID NO:62, a light chain CDR2 having the amino acid sequence of SEQ ID NO:63, and a light chain CDR3 having the amino acid sequence of SEQ ID NO:64; wherein (g) the variable domain region from the heavy chain comprises: a heavy chain CDR1 having the amino acid sequence of SEQ ID NO:65, a heavy chain CDR2 having the amino acid sequence of SEQ ID NO:66, a heavy chain CDR3 having the amino acid sequence of SEQ ID NO:67; and the variable domain region from the light chain comprises: a light chain CDR1 having the amino acid sequence of SEQ ID NO:68, a light chain CDR2 having the amino acid sequence of SEQ ID NO:69, and a light chain CDR3 having the amino acid sequence of SEQ ID NO:70; wherein (h) the variable domain region from the heavy chain comprises: a heavy chain CDR1 having the amino acid sequence of SEQ ID NO:71, a heavy chain CDR2 having the amino acid sequence of SEQ ID NO:72, a heavy chain CDR3 having the amino acid sequence of SEQ ID NO:73; and the variable domain region from the light chain comprises: a light chain CDR1 having the amino acid sequence of SEQ ID NO:74, a light chain CDR2 having the amino acid sequence of SEQ ID NO:75, and a light chain CDR3 having the amino acid sequence of SEQ ID NO:76; wherein (i) the variable domain region from the heavy chain comprises: a heavy chain CDR1 having the amino acid sequence of SEQ ID NO:77, a heavy chain CDR2 having the amino acid sequence of SEQ ID NO:78, a heavy chain CDR3 having the amino acid sequence of SEQ ID NO:79; and the variable domain region from the light chain comprises: a light chain CDR1 having the amino acid sequence of SEQ ID NO:80, a light chain CDR2 having the amino acid sequence of SEQ ID NO:81, and a light chain CDR3 having the amino acid sequence of SEQ ID NO:82; wherein (j) the variable domain region from the heavy chain comprises: a heavy chain CDR1 having the amino acid sequence of SEQ ID NO:83, a heavy chain CDR2 having the amino acid sequence of SEQ ID NO:84, a heavy chain CDR3 having the amino acid sequence of SEQ ID NO:85; and the variable domain region from the light chain comprises: a light chain CDR1 having the amino acid sequence of SEQ ID NO:86, a light chain CDR2 having the amino acid sequence of SEQ ID NO:87, and a light chain CDR3 having the amino acid sequence of SEQ ID NO:88; or wherein (k) the variable domain region from the heavy chain comprises: a heavy chain CDR1 having the amino acid sequence of SEQ ID NO:53, a heavy chain CDR2 having the amino acid sequence of SEQ ID NO:54, a heavy chain CDR3 having the amino acid sequence of SEQ ID NO:55; and the variable domain region from the light chain comprises: a lambda light chain CDR1 having the amino acid sequence of SEQ ID NO:89, a lambda light chain CDR2 having the amino acid sequence of SEQ ID NO:90, and a lambda light chain CDR3 having the amino acid sequence of SEQ ID NO:91.

The present disclosure provides a fully human anti-BCMA antibody, or the antigen-binding fragment thereof, wherein the antigen-binding fragment is a Fab fragment comprising a variable domain region from a heavy chain and a variable domain region from a light chain, wherein the variable domain region from the heavy chain comprises a sequence having at least 95% sequence identity to the amino acid sequence of SEQ ID NO: 8, 10, 12, 14 or 22, and wherein the variable domain region from the light chain comprises a sequence having at least 95% sequence identity to the amino acid sequence of SEQ ID NO: 9, 11, 13, 15, 16, 17, 18, 19, 20, 21 or 23.

The present disclosure provides a fully human anti-BCMA antibody, or the antigen-binding fragment thereof, wherein the antigen-binding fragment is a Fab fragment comprising a variable domain region from a heavy chain and a variable domain region from a light chain, wherein the variable domain region from the heavy chain and the variable domain region from the light chain are SEQ ID NOS:8 and 9 (e.g., herein called BCA7); SEQ ID NOS:10 and 11 (e.g., herein called BC4C9); SEQ ID NOS:12 and 13 (e.g., herein called CD5C4); SEQ ID NOS:14 and 15 (e.g., herein called BC6G8); SEQ ID NOS:8 and 16 (e.g., herein called BCA7-2C5); SEQ ID NOS:8 and 17 (e.g., herein called BCA7-2E1); SEQ ID NOS:8 and 18 (e.g., herein called BCA7-2D11); SEQ ID NOS:8 and 19 (e.g., herein called BCA7-2G2); SEQ ID NOS:8 and 20 (e.g., herein called BCA7-2D8); SEQ ID NOS:8 and 21 (e.g., herein called BCA7-2E8); or SEQ ID NOS:22 and 23 (e.g., herein called BCA7-2C5 with lambda light chain).

The present disclosure provides a fully human anti-BCMA antibody, or the antigen-binding fragment thereof, wherein the antigen-binding fragment is a single chain antibody comprising a variable domain region from a heavy chain and a variable domain region from a light chain joined together with a peptide linker, wherein (a) the variable domain region from the heavy chain comprises: a heavy chain complementarity determining region 1 (CDR1) having the amino acid sequence of SEQ ID NO:29, a heavy chain CDR2 having the amino acid sequence of SEQ ID NO:30, a heavy chain CDR3 having the amino acid sequence of SEQ ID NO:31; and the variable domain region from the light chain comprises: a light chain CDR1 having the amino acid sequence of SEQ ID NO:32, a light chain CDR2 having the amino acid sequence of SEQ ID NO:33, and a light chain CDR3 having the amino acid sequence of SEQ ID NO:34; wherein (b) the variable domain region from the heavy chain comprises: a heavy chain CDR1 having the amino acid sequence of SEQ ID NO:35, a heavy chain CDR2 having the amino acid sequence of SEQ ID NO:36, a heavy chain CDR3 having the amino acid sequence of SEQ ID NO:37; and the variable domain region from the light chain comprises: a light chain CDR1 having the amino acid sequence of SEQ ID NO:38, a light chain CDR2 having the amino acid sequence of SEQ ID NO:39, and a light chain CDR3 having the amino acid sequence of SEQ ID NO:40; wherein (c) the variable domain region from the heavy chain comprises: a heavy chain CDR1 having the amino acid sequence of SEQ ID NO:41, a heavy chain CDR2 having the amino acid sequence of SEQ ID NO:42, a heavy chain CDR3 having the amino acid sequence of SEQ ID NO:43; and the variable domain region from the light chain comprises: a light chain CDR1 having the amino acid sequence of SEQ ID NO:44, a light chain CDR2 having the amino acid sequence of SEQ ID NO:45, and a light chain CDR3 having the amino acid sequence of SEQ ID NO:46; wherein (d) the variable domain region from the heavy chain comprises: a heavy chain CDR1 having the amino acid sequence of SEQ ID NO:47, a heavy chain CDR2 having the amino acid sequence of SEQ ID NO:48, a heavy chain CDR3 having the amino acid sequence of SEQ ID NO:49; and the variable domain region from the light chain comprises: a light chain CDR1 having the amino acid sequence of SEQ ID NO:50, a light chain CDR2 having the amino acid sequence of SEQ ID NO:51, and a light chain CDR3 having the amino acid sequence of SEQ ID NO:52; wherein (e) the variable domain region from the heavy chain comprises: a heavy chain CDR1 having the amino acid sequence of SEQ ID NO:53, a heavy chain CDR2 having the amino acid sequence of SEQ ID NO:54, a heavy chain CDR3 having the amino acid sequence of SEQ ID NO:55; and the variable domain region from the light chain comprises: a light chain CDR1 having the amino acid sequence of SEQ ID NO:56, a light chain CDR2 having the amino acid sequence of SEQ ID NO:57, and a light chain CDR3 having the amino acid sequence of SEQ ID NO:58; wherein (f) the variable domain region from the heavy chain comprises: a heavy chain CDR1 having the amino acid sequence of SEQ ID NO:59, a heavy chain CDR2 having the amino acid sequence of SEQ ID NO:60, a heavy chain CDR3 having the amino acid sequence of SEQ ID NO:61; and the variable domain region from the light chain comprises: a light chain CDR1 having the amino acid sequence of SEQ ID NO:62, a light chain CDR2 having the amino acid sequence of SEQ ID NO:63, and a light chain CDR3 having the amino acid sequence of SEQ ID NO:64; wherein (g) the variable domain region from the heavy chain comprises: a heavy chain CDR1 having the amino acid sequence of SEQ ID NO:65, a heavy chain CDR2 having the amino acid sequence of SEQ ID NO:66, a heavy chain CDR3 having the amino acid sequence of SEQ ID NO:67; and the variable domain region from the light chain comprises: a light chain CDR1 having the amino acid sequence of SEQ ID NO:68, a light chain CDR2 having the amino acid sequence of SEQ ID NO:69, and a light chain CDR3 having the amino acid sequence of SEQ ID NO:70; wherein (h) the variable domain region from the heavy chain comprises: a heavy chain CDR1 having the amino acid sequence of SEQ ID NO:71, a heavy chain CDR2 having the amino acid sequence of SEQ ID NO:72, a heavy chain CDR3 having the amino acid sequence of SEQ ID NO:73; and the variable domain region from the light chain comprises: a light chain CDR1 having the amino acid sequence of SEQ ID NO:74, a light chain CDR2 having the amino acid sequence of SEQ ID NO:75, and a light chain CDR3 having the amino acid sequence of SEQ ID NO:76; wherein (i) the variable domain region from the heavy chain comprises: a heavy chain CDR1 having the amino acid sequence of SEQ ID NO:77, a heavy chain CDR2 having the amino acid sequence of SEQ ID NO:78, a heavy chain CDR3 having the amino acid sequence of SEQ ID NO:79; and the variable domain region from the light chain comprises: a light chain CDR1 having the amino acid sequence of SEQ ID NO:80, a light chain CDR2 having the amino acid sequence of SEQ ID NO:81, and a light chain CDR3 having the amino acid sequence of SEQ ID NO:82; wherein (j) the variable domain region from the heavy chain comprises: a heavy chain CDR1 having the amino acid sequence of SEQ ID NO:83, a heavy chain CDR2 having the amino acid sequence of SEQ ID NO:84, a heavy chain CDR3 having the amino acid sequence of SEQ ID NO:85; and the variable domain region from the light chain comprises: a light chain CDR1 having the amino acid sequence of SEQ ID NO:86, a light chain CDR2 having the amino acid sequence of SEQ ID NO:87, and a light chain CDR3 having the amino acid sequence of SEQ ID NO:88; or wherein (k) the variable domain region from the heavy chain comprises: a heavy chain CDR1 having the amino acid sequence of SEQ ID NO:53, a heavy chain CDR2 having the amino acid sequence of SEQ ID NO:54, a heavy chain CDR3 having the amino acid sequence of SEQ ID NO:55; and the variable domain region from the light chain comprises: a lambda light chain CDR1 having the amino acid sequence of SEQ ID NO:89, a lambda light chain CDR2 having the amino acid sequence of SEQ ID NO:90, and a lambda light chain CDR3 having the amino acid sequence of SEQ ID NO:91.

The present disclosure provides a fully human anti-BCMA antibody, or the antigen-binding fragment thereof, wherein the antigen-binding fragment is a single chain antibody comprising a variable domain region from a heavy chain and a variable domain region from a light chain joined together with a peptide linker, wherein the variable domain region from the heavy chain comprises a sequence having at least 95% sequence identity to the amino acid sequence of SEQ ID NO: 8, 10, 12, 14 or 22, and wherein the variable domain region from the light chain comprises a sequence having at least 95% sequence identity to the amino acid sequence of SEQ ID NO: 9, 11, 13, 15, 16, 17, 18, 19, 20, 21 or 23.

The present disclosure provides a fully human anti-BCMA antibody, or the antigen-binding fragment thereof, wherein the antigen-binding fragment is a single chain antibody comprising a variable domain region from a heavy chain and a variable domain region from a light chain joined together with a peptide linker, wherein the variable domain region from the heavy chain and the variable domain region from the light chain are SEQ ID NOS:8 and 9 (e.g., herein called BCA7); SEQ ID NOS:10 and 11 (e.g., herein called BC4C9); SEQ ID NOS:12 and 13 (e.g., herein called CD5C4); SEQ ID NOS:14 and 15 (e.g., herein called BC6G8); SEQ ID NOS:8 and 16 (e.g., herein called BCA7-2C5); SEQ ID NOS:8 and 17 (e.g., herein called BCA7-2E1); SEQ ID NOS:8 and 18 (e.g., herein called BCA7-2D11); SEQ ID NOS:8 and 19 (e.g., herein called BCA7-2G2); SEQ ID NOS:8 and 20 (e.g., herein called BCA7-2D8); SEQ ID NOS:8 and 21 (e.g., herein called BCA7-2E8); or SEQ ID NOS:22 and 23 (e.g., herein called BCA7-2C5 with lambda light chain).

In one embodiment, any of the fully human anti-BCMA antibodies disclosed herein, or any of the antigen-binding fragments thereof, comprise an IgG1, IgG2, IgG3 or IgG4 antibody.

In one embodiment, any of the fully human anti-BCMA antibodies disclosed herein, or any of the antigen-binding fragments thereof, comprise an IgG1 or IgG4 isotype antibody.

In one embodiment, any of the fully human anti-BCMA antibodies disclosed herein, or any of the antigen-binding fragments thereof, can block binding of human APRIL (A PRoliferation-Inducing Ligand; also known as TNF13 and CD256) protein to human BCMA protein.

In one embodiment, any of the fully human anti-BCMA antibodies disclosed herein, or any of the antigen-binding fragments thereof, bind to human BCMA protein and cross-reacts with BCMA protein from mouse and cynomolgus.

In one embodiment, any of the fully human anti-BCMA antibodies disclosed herein, or any of the antigen-binding fragments thereof, bind to human BCMA protein and do not cross-react with BCMA protein from mouse or cynomolgus.

In one embodiment, any of the fully human anti-BCMA antibodies disclosed herein, or any of the antigen-binding fragments thereof, which bind human BCMA protein with a $K_D$ of $10^{-8}$ M or less.

In one embodiment, any of the fully human anti-BCMA antibodies disclosed herein, or any of the antigen-binding fragments thereof, bind cynomolgus BCMA protein with a $K_D$ of $10^{-7}$ M or less.

In one embodiment, any of the fully human anti-BCMA antibodies disclosed herein, or any of the antigen-binding fragments thereof, bind mouse BCMA protein with a $K_D$ of $10^{-5}$ M or less.

In one embodiment, any of the fully human anti-BCMA antibodies disclosed herein, or any of the antigen-binding fragments thereof, bind to cells expressing BCMA protein including for example bind to human myeloma cells expressing BCMA protein.

The present disclosure provides a pharmaceutical composition, comprising any one of the disclosed the human anti-BCMA antibodies, or any of the antigen-binding fragments thereof, and a pharmaceutically-acceptable excipient.

The present disclosure provides a kit, comprising any one of the disclosed the human anti-BCMA antibodies, or any of the antigen-binding fragments thereof.

The present disclosure provides a first nucleic acid that encodes a first polypeptide comprising an antibody heavy chain variable region having a heavy chain complementarity determining region (CDR) of any one of disclosed the human anti-BCMA antibodies, including (a) a heavy chain CDR1 having the amino acid sequence of SEQ ID NO:29, a heavy chain CDR2 having the amino acid sequence of SEQ ID NO:30, and a heavy chain CDR3 having the amino acid sequence of SEQ ID NO:31; or (b) a heavy chain CDR1 having the amino acid sequence of SEQ ID NO:35, a heavy chain CDR2 having the amino acid sequence of SEQ ID NO:36, and a heavy chain CDR3 having the amino acid sequence of SEQ ID NO:37; or (c) a heavy chain CDR1 having the amino acid sequence of SEQ ID NO:41, a heavy chain CDR2 having the amino acid sequence of SEQ ID NO:42, and a heavy chain CDR3 having the amino acid sequence of SEQ ID NO:43; or (d) a heavy chain CDR1 having the amino acid sequence of SEQ ID NO:47, a heavy chain CDR2 having the amino acid sequence of SEQ ID NO:48, and a heavy chain CDR3 having the amino acid sequence of SEQ ID NO:49; or (e) a heavy chain CDR1 having the amino acid sequence of SEQ ID NO:53, a heavy chain CDR2 having the amino acid sequence of SEQ ID NO:54, and a heavy chain CDR3 having the amino acid sequence of SEQ ID NO:55; or (f) a heavy chain CDR1 having the amino acid sequence of SEQ ID NO:59, a heavy chain CDR2 having the amino acid sequence of SEQ ID NO:60, and a heavy chain CDR3 having the amino acid sequence of SEQ ID NO:61; or (g) a heavy chain CDR1 having the amino acid sequence of SEQ ID NO:65, a heavy chain CDR2 having the amino acid sequence of SEQ ID NO:66, and a heavy chain CDR3 having the amino acid sequence of SEQ ID NO:67; or (h) a heavy chain CDR1 having the amino acid sequence of SEQ ID NO:71, a heavy chain CDR2 having the amino acid sequence of SEQ ID NO:72, and a heavy chain CDR3 having the amino acid sequence of SEQ ID NO:73; or (i) a heavy chain CDR1 having the amino acid sequence of SEQ ID NO:77, a heavy chain CDR2 having the amino acid sequence of SEQ ID NO:78, and a heavy chain CDR3 having the amino acid sequence of SEQ ID NO:79; or (j) a heavy chain CDR1 having the amino acid sequence of SEQ ID NO:83, a heavy chain CDR2 having the amino acid sequence of SEQ ID NO:84, and a heavy chain CDR3 having the amino acid sequence of SEQ ID NO:85.

The present disclosure provides a first vector operably linked to a first nucleic acid which encodes a first polypeptide comprising an antibody heavy chain variable region having the CDRs 1, 2 and 3, of any one of the disclosed the human anti-BCMA antibodies disclosed herein.

The present disclosure provides a first host cell harboring the first vector operably linked to the first nucleic acid which encodes the first polypeptide comprising an antibody heavy chain variable region having the CDRs 1, 2 and 3, of any one of the disclosed the human anti-BCMA antibodies disclosed herein. In one embodiment, the first vector comprises a first expression vector. In one embodiment, the first host cell expresses the first polypeptide comprising the antibody heavy chain variable region having the CDRs 1, 2 and 3, of any one of the disclosed the human anti-BCMA antibodies disclosed herein.

The present disclosure provides a method for preparing a first polypeptide having an antibody heavy chain variable region comprising CDRs 1, 2 and 3, the method comprising: culturing a population (e.g., a plurality) of the first host cells harboring the first expression vector under conditions suitable for expressing the first polypeptide having the antibody heavy chain variable region comprising the CDRs 1, 2 and 3. In one embodiment, the method further comprises: recovering from the population of the first host cell the expressed first polypeptide having an antibody heavy chain variable region comprising the CDRs 1, 2 and 3.

The present disclosure provides a first nucleic acid that encodes a first polypeptide comprising an antibody heavy chain variable region having at least 95% sequence identity to the amino acid sequence of SEQ ID NO: 8, 10, 12, 14 or 22.

The present disclosure provides a first vector operably linked to the first nucleic acid which encodes the first polypeptide comprising the antibody heavy chain variable region having at least 95% sequence identity to the amino acid sequence of SEQ ID NO: 8, 10, 12, 14 or 22.

The present invention provides a first host cell harboring the first vector operably linked to the first nucleic acid which encodes the first polypeptide comprising the antibody heavy chain variable region having at least 95% sequence identity to the amino acid sequence of SEQ ID NO: 8, 10, 12, 14 or 22. In one embodiment, the first vector comprises a first expression vector. In one embodiment, the first host cell expresses the first polypeptide comprising the antibody heavy chain variable region having at least 95% sequence identity to the amino acid sequence of SEQ ID NO: 8, 10, 12, 14 or 22.

The present disclosure provides a method for preparing a first polypeptide having an antibody heavy chain variable region, the method comprising: culturing a population (e.g., a plurality) of the first host cells harboring the first expression vector under conditions suitable for expressing the first polypeptide having the antibody heavy chain variable region having at least 95% sequence identity to the amino acid sequence of SEQ ID NO: 8, 10, 12, 14 or 22. In one embodiment, the method further comprises: recovering from the population of the first host cells the expressed first polypeptide having at least 95% sequence identity to the amino acid sequence of SEQ ID NO: 8, 10, 12, 14 or 22.

The present disclosure provides a second nucleic acid that encodes a polypeptide comprising an antibody light chain variable region having a light chain complementarity determining region (CDR) of any one of disclosed the human anti-BCMA antibodies, including (a) a light chain CDR1 having the amino acid sequence of SEQ ID NO:32, a light chain CDR2 having the amino acid sequence of SEQ ID NO:33, and a light chain CDR3 having the amino acid sequence of SEQ ID NO:34; or (b) a light chain CDR1 having the amino acid sequence of SEQ ID NO:38, a light chain CDR2 having the amino acid sequence of SEQ ID NO:39, and a light chain CDR3 having the amino acid sequence of SEQ ID NO:40; or (c) a light chain CDR1 having the amino acid sequence of SEQ ID NO:44, a light chain CDR2 having the amino acid sequence of SEQ ID NO:45, and a light chain CDR3 having the amino acid sequence of SEQ ID NO:46; or (d) a light chain CDR1 having the amino acid sequence of SEQ ID NO:50, a light chain CDR2 having the amino acid sequence of SEQ ID NO:51, and a light chain CDR3 having the amino acid sequence of SEQ ID NO:52; or (e) a light chain CDR1 having the amino acid sequence of SEQ ID NO:56, a light chain CDR2 having the amino acid sequence of SEQ ID NO:57, and a light chain CDR3 having the amino acid sequence of SEQ ID NO:58; or (f) a light chain CDR1 having the amino acid sequence of SEQ ID NO:62, a light chain CDR2 having the amino acid sequence of SEQ ID NO:63, and a light chain CDR3 having the amino acid sequence of SEQ ID NO:64; or (g) a light chain CDR1 having the amino acid sequence of SEQ ID NO:68, a light chain CDR2 having the amino acid sequence of SEQ ID NO:69, and a light chain CDR3 having the amino acid sequence of SEQ ID NO:70; or (h) a light chain CDR1 having the amino acid sequence of SEQ ID NO:74, a light chain CDR2 having the amino acid sequence of SEQ ID NO:75, and a light chain CDR3 having the amino acid sequence of SEQ ID NO:76; or (i) a light chain CDR1 having the amino acid sequence of SEQ ID NO:80, a light chain CDR2 having the amino acid sequence of SEQ ID NO:81, and a light chain CDR3 having the amino acid sequence of SEQ ID NO:82; or (j) a light chain CDR1 having the amino acid sequence of SEQ ID NO:86, a light chain CDR2 having the amino acid sequence of SEQ ID NO:87, and a light chain CDR3 having the amino acid sequence of SEQ ID NO:88; or (k) a lambda light chain CDR1 having the amino acid sequence of SEQ ID NO:89, a lambda light chain CDR2 having the amino acid sequence of SEQ ID NO:90, and a lambda light chain CDR3 having the amino acid sequence of SEQ ID NO:91.

The present disclosure provides a second vector operably linked to a second nucleic acid which encodes a second polypeptide comprising an antibody light chain variable region having the CDRs 1, 2 and 3, of any one of the disclosed the human anti-BCMA antibodies disclosed herein.

The present disclosure provides a second host cell harboring the second vector operably linked to the second nucleic acid which encodes the second polypeptide comprising an antibody light chain variable region having the CDRs 1, 2 and 3, of any one of the disclosed the human anti-BCMA antibodies disclosed herein. In one embodiment, the second vector comprises a second expression vector. In one embodiment, the second host cell expresses the second polypeptide comprising the antibody light chain variable region having the CDRs 1, 2 and 3, of any one of the disclosed the human anti-BCMA antibodies disclosed herein.

The present disclosure provides a method for preparing a second polypeptide having an antibody light chain variable region comprising CDRs 1, 2 and 3, the method comprising: culturing a population (e.g., a plurality) of the second host cells harboring the second expression vector under conditions suitable for expressing the second polypeptide having the antibody light chain variable region comprising the CDRs 1, 2 and 3. In one embodiment, the method further comprises: recovering from the population of the second host cell the expressed second polypeptide having an antibody light chain variable region comprising the CDRs 1, 2 and 3.

The present disclosure provides a second nucleic acid that encodes a second polypeptide comprising an antibody light chain variable region having at least 95% sequence identity to the amino acid sequence of SEQ ID NO: 9, 11, 13, 15, 16, 17, 18, 19, 20, 21 or 23.

The present disclosure provides a second vector operably linked to the second nucleic acid which encodes the second polypeptide comprising the antibody light chain variable region having at least 95% sequence identity to the amino acid sequence of SEQ ID NO: 9, 11, 13, 15, 16, 17, 18, 19, 20, 21 or 23.

The present invention provides a second host cell harboring the second vector operably linked to the second nucleic acid which encodes the second polypeptide comprising the antibody light chain variable region having at least 95% sequence identity to the amino acid sequence of SEQ ID NO: 9, 11, 13, 15, 16, 17, 18, 19, 20, 21 or 23. In one embodiment, the second vector comprises a second expression vector. In one embodiment, the second host cell expresses the second polypeptide comprising the antibody light chain variable region having at least 95% sequence identity to the amino acid sequence of SEQ ID NO: 9, 11, 13, 15, 16, 17, 18, 19, 20, 21 or 23.

The present disclosure provides a method for preparing a second polypeptide having an antibody light chain variable region, the method comprising: culturing a population (e.g., a plurality) of the second host cells harboring the second expression vector under conditions suitable for expressing the second polypeptide having the antibody light chain variable region having at least 95% sequence identity to the amino acid sequence of SEQ ID NO: 9, 11, 13, 15, 16, 17, 18, 19, 20, 21 or 23. In one embodiment, the method further comprises: recovering from the population of the second host cells the expressed second polypeptide having at least 95% sequence identity to the amino acid sequence of SEQ ID NO: 8, 10, 12, 14 or 22.

The present disclosure provides a first nucleic acid that encodes a first polypeptide comprising an antibody heavy chain variable region having heavy chain complementarity determining regions (HC-CDRs 1, 2 and 3) of any one of disclosed the human anti-BCMA antibodies, and a second nucleic acid that encodes a second polypeptide comprising an antibody light chain variable region having light chain complementarity determining regions (LC-CDRs 1, 2 and 3) of any one of disclosed the human anti-BCMA antibodies, wherein (a) the heavy chain CDR 1, 2 and 3 regions comprise the amino acid sequences of SEQ ID NOS:29, 30 and 31, respectively, and the light chain CDR 1, 2 and 3 regions comprise the amino acid sequences of SEQ ID NOS:32, 33 and 34, respectively; or (b) the heavy chain CDR 1, 2 and 3 regions comprise the amino acid sequences of SEQ ID NOS:35, 36 and 37, respectively, and the light chain CDR 1, 2 and 3 regions comprise the amino acid sequences of SEQ ID NOS:38, 39 and 40, respectively; or (c) the heavy chain CDR 1, 2 and 3 regions comprise the amino acid sequences of SEQ ID NOS:41, 42 and 43, respectively, and the light chain CDR 1, 2 and 3 regions comprise the amino acid sequences of SEQ ID NOS:44, 45 and 46, respectively; or (d) the heavy chain CDR 1, 2 and 3 regions comprise the amino acid sequences of SEQ ID NOS:47, 48 and 49, respectively, and the light chain CDR 1, 2 and 3 regions comprise the amino acid sequences of SEQ ID NOS:50, 51 and 52, respectively; or (e) the heavy chain CDR 1, 2 and 3 regions comprise the amino acid sequences of SEQ ID NOS:53, 54 and 55, respectively, and the light chain CDR 1, 2 and 3 regions comprise the amino acid sequences of SEQ ID NOS:56, 57 and 58, respectively; or (f)

the heavy chain CDR 1, 2 and 3 regions comprise the amino acid sequences of SEQ ID NOS:59, 60 and 61, respectively, and the light chain CDR 1, 2 and 3 regions comprise the amino acid sequences of SEQ ID NOS:62, 63 and 64, respectively; or (g) the heavy chain CDR 1, 2 and 3 regions comprise the amino acid sequences of SEQ ID NOS:65, 66 and 67, respectively, and the light chain CDR 1, 2 and 3 regions comprise the amino acid sequences of SEQ ID NOS:68, 69 and 70, respectively; or (h) the heavy chain CDR 1, 2 and 3 regions comprise the amino acid sequences of SEQ ID NOS:71, 72 and 73, respectively, and the light chain CDR 1, 2 and 3 regions comprise the amino acid sequences of SEQ ID NOS:74, 75 and 76, respectively; or (i) the heavy chain CDR 1, 2 and 3 regions comprise the amino acid sequences of SEQ ID NOS:77, 78 and 79, respectively, and the light chain CDR 1, 2 and 3 regions comprise the amino acid sequences of SEQ ID NOS:80, 81 and 82, respectively; or (j) the heavy chain CDR 1, 2 and 3 regions comprise the amino acid sequences of SEQ ID NOS:83, 84 and 85, respectively, and the light chain CDR 1, 2 and 3 regions comprise the amino acid sequences of SEQ ID NOS:86, 87 and 88, respectively; or (k) the heavy chain CDR 1, 2 and 3 regions comprise the amino acid sequences of SEQ ID NOS:53, 54 and 55, respectively, and the light chain CDR 1, 2 and 3 regions comprise the amino acid sequences of SEQ ID NOS:89, 90 and 91, respectively.

The present disclosure provides a vector operably linked to the first nucleic acid that encodes the first polypeptide comprising an antibody heavy chain variable region having heavy chain complementarity determining regions (HC-CDRs 1, 2 and 3) of any one of disclosed the human anti-BCMA antibodies, and the vector is operably linked to the second nucleic acid that encodes the second polypeptide comprising the antibody light chain variable region having light chain complementarity determining regions (LC-CDRs 1, 2 and 3) of any one of disclosed the human anti-BCMA antibodies.

The present disclosure provides a host cell harboring the vector which is operably linked to the first nucleic acid that encodes the first polypeptide comprising the heavy chain complementarity determining regions (HC-CDRs 1, 2 and 3) of any one of disclosed the human anti-BCMA antibodies and the second nucleic acid that encodes the second polypeptide comprising the light chain complementarity determining regions (LC-CDRs 1, 2 and 3) of any one of disclosed the human anti-BCMA antibodies. In one embodiment, the vector comprises an expression vector. In one embodiment, the host cell expresses the first polypeptide comprising the heavy chain complementarity determining regions (HC-CDRs 1, 2 and 3) of any one of disclosed the human anti-BCMA antibodies and the second polypeptide comprising the light chain complementarity determining regions (LC-CDRs 1, 2 and 3) of any one of disclosed the human anti-BCMA antibodies.

The present disclosure provides a method for preparing the first and second polypeptides, the method comprising: culturing a population (e.g., a plurality) of the host cell harboring the expression vector under conditions suitable for expressing the first polypeptide comprising the heavy chain complementarity determining regions (HC-CDRs 1, 2 and 3) of any one of disclosed the human anti-BCMA antibodies and the second polypeptide comprising the light chain complementarity determining regions (LC-CDRs 1, 2 and 3) of any one of disclosed the human anti-BCMA antibodies. In one embodiment, the method further comprises: recovering from the population of the host cells the expressed first and second polypeptides.

The present disclosure provides a first nucleic acid that encodes a first polypeptide comprising an antibody heavy chain variable region having at least 95% sequence identity to the amino acid sequence of SEQ ID NO: 8, 10, 12, 14 or 22, and a second nucleic acid that encodes a second polypeptide comprising an antibody light chain variable region having at least 95% sequence identity to the amino acid sequence of SEQ ID NO: 9, 11, 13, 15, 16, 17, 18, 19, 20, 21 or 23.

The present disclosure provides a vector operably linked to the first nucleic acid that encodes a first polypeptide comprising an antibody heavy chain variable region having at least 95% sequence identity to the amino acid sequence of SEQ ID NO: 8, 10, 12, 14 or 22, and the vector is operably linked to the second nucleic acid which encodes the second polypeptide comprising the antibody light chain variable region having at least 95% sequence identity to the amino acid sequence of SEQ ID NO: 9, 11, 13, 15, 16, 17, 18, 19, 20, 21 or 23.

The present invention provides a host cell harboring the vector operably linked to the first nucleic acid that encodes a first polypeptide comprising an antibody heavy chain variable region having at least 95% sequence identity to the amino acid sequence of SEQ ID NO: 8, 10, 12, 14 or 22, and the vector is operably linked to the second nucleic acid which encodes the second polypeptide comprising the antibody light chain variable region having at least 95% sequence identity to the amino acid sequence of SEQ ID NO: 9, 11, 13, 15, 16, 17, 18, 19, 20, 21 or 23. In one embodiment, the vector comprises an expression vector. In one embodiment, the host cell expresses the first polypeptide comprising an antibody heavy chain variable region having at least 95% sequence identity to the amino acid sequence of SEQ ID NO: 8, 10, 12, 14 or 22, and the host cell expresses the second polypeptide comprising the antibody light chain variable region having at least 95% sequence identity to the amino acid sequence of SEQ ID NO: 9, 11, 13, 15, 16, 17, 18, 19, 20, 21 or 23.

The present disclosure provides a method for preparing a first polypeptide having an antibody heavy chain variable region and a second polypeptide having an antibody light chain variable region, the method comprising: culturing a population (e.g., a plurality) of the host cells harboring the expression vector under conditions suitable for expressing the first polypeptide comprising an antibody heavy chain variable region having at least 95% sequence identity to the amino acid sequence of SEQ ID NO: 8, 10, 12, 14 or 22, and for expressing the second polypeptide having the antibody light chain variable region having at least 95% sequence identity to the amino acid sequence of SEQ ID NO: 9, 11, 13, 15, 16, 17, 18, 19, 20, 21 or 23. In one embodiment, the method further comprises: recovering from the population of the host cells the expressed first polypeptide comprising an antibody heavy chain variable region having at least 95% sequence identity to the amino acid sequence of SEQ ID NO: 8, 10, 12, 14 or 22, and the expressed second polypeptide having at least 95% sequence identity to the amino acid sequence of SEQ ID NO: 8, 10, 12, 14 or 22.

The present disclosure provides a first nucleic acid that encodes a first polypeptide comprising an antibody heavy chain variable region having heavy chain complementarity determining regions (HC-CDRs 1, 2 and 3) of any one of disclosed the human anti-BCMA antibodies, and a second nucleic acid that encodes a second polypeptide comprising an antibody light chain variable region having light chain complementarity determining regions (LC-CDRs 1, 2 and 3) of any one of disclosed the human anti-BCMA antibodies, wherein (a) the heavy chain CDR 1, 2 and 3 regions comprise the amino acid sequences of SEQ ID NOS:29, 30 and 31, respectively, and the light chain CDR 1, 2 and 3 regions comprise the amino acid sequences of SEQ ID NOS:32, 33 and 34, respectively; or (b) the heavy chain CDR 1, 2 and 3 regions comprise the amino acid sequences of SEQ ID NOS:35, 36 and 37, respectively, and the light chain CDR 1, 2 and 3 regions comprise the amino acid sequences of SEQ ID NOS:38, 39 and 40, respectively; or (c) the heavy chain CDR 1, 2 and 3 regions comprise the amino acid sequences of SEQ ID NOS:41, 42 and 43, respectively, and the light chain CDR 1, 2 and 3 regions comprise the amino acid sequences of SEQ ID NOS:44, 45 and 46, respectively; or (d) the heavy chain CDR 1, 2 and 3 regions comprise the amino acid sequences of SEQ ID NOS:47, 48 and 49, respectively, and the light chain CDR 1, 2 and 3 regions comprise the amino acid sequences of SEQ ID NOS:50, 51 and 52, respectively; or (e) the heavy chain CDR 1, 2 and 3 regions comprise the amino acid sequences of SEQ ID NOS:53, 54 and 55, respectively, and the light chain CDR 1, 2 and 3 regions comprise the amino acid sequences of SEQ ID NOS:56, 57 and 58, respectively; or (f) the heavy chain CDR 1, 2 and 3 regions comprise the amino acid sequences of SEQ ID NOS:59, 60 and 61, respectively, and the light chain CDR 1, 2 and 3 regions comprise the amino acid sequences of SEQ ID NOS:62, 63 and 64, respectively; or (g) the heavy chain CDR 1, 2 and 3 regions comprise the amino acid sequences of SEQ ID NOS:65, 66 and 67, respectively, and the light chain CDR 1, 2 and 3 regions comprise the amino acid sequences of SEQ ID NOS:68, 69 and 70, respectively; or (h) the heavy chain CDR 1, 2 and 3 regions comprise the amino acid sequences of SEQ ID NOS:71, 72 and 73, respectively, and the light chain CDR 1, 2 and 3 regions comprise the amino acid sequences of SEQ ID NOS:74, 75 and 76, respectively; or (i) the heavy chain CDR 1, 2 and 3 regions comprise the amino acid sequences of SEQ ID NOS:77, 78 and 79, respectively, and the light chain CDR 1, 2 and 3 regions comprise the amino acid sequences of SEQ ID NOS:80, 81 and 82, respectively; or (j) the heavy chain CDR 1, 2 and 3 regions comprise the amino acid sequences of SEQ ID NOS:83, 84 and 85, respectively, and the light chain CDR 1, 2 and 3 regions comprise the amino acid sequences of SEQ ID NOS:86, 87 and 88, respectively; or (k) the heavy chain CDR 1, 2 and 3 regions comprise the amino acid sequences of SEQ ID NOS:53, 54 and 55, respectively, and the light chain CDR 1, 2 and 3 regions comprise the amino acid sequences of SEQ ID NOS:89, 90 and 91, respectively.

The present disclosure provides a first vector operably linked to the first nucleic acid that encodes the first polypeptide comprising an antibody heavy chain variable region having heavy chain complementarity determining regions (HC-CDRs 1, 2 and 3) of any one of disclosed the human anti-BCMA antibodies, and a second vector operably linked to the second nucleic acid that encodes the second polypeptide comprising the antibody light chain variable region having light chain complementarity determining regions (LC-CDRs 1, 2 and 3) of any one of disclosed the human anti-BCMA antibodies.

The present disclosure provides a host cell harboring the first vector which is operably linked to the first nucleic acid that encodes the first polypeptide comprising the heavy chain complementarity determining regions (HC-CDRs 1, 2 and 3) of any one of disclosed the human anti-BCMA antibodies, and the host cell harbors the second vector which is operably linked to the second nucleic acid that encodes the second polypeptide comprising the light chain complementarity determining regions (LC-CDRs 1, 2 and 3) of any one of disclosed the human anti-BCMA antibodies. In one embodiment, the first and second vectors are first and second expression vectors, respectively. In one embodiment, the host cell expresses the first polypeptide comprising the heavy chain complementarity determining regions (HC-CDRs 1, 2 and 3) of any one of disclosed the human anti-BCMA antibodies and the host cell expresses the second polypeptide comprising the light chain complementarity determining regions (LC-CDRs 1, 2 and 3) of any one of disclosed the human anti-BCMA antibodies.

The present disclosure provides a method for preparing the first and second polypeptides, the method comprising: culturing a population (e.g., a plurality) of the host cell harboring the first and second expression vectors under conditions suitable for expressing the first polypeptide comprising the heavy chain complementarity determining regions (HC-CDRs 1, 2 and 3) of any one of disclosed the human anti-BCMA antibodies and the second polypeptide comprising the light chain complementarity determining regions (LC-CDRs 1, 2 and 3) of any one of disclosed the human anti-BCMA antibodies. In one embodiment, the method further comprises: recovering from the population of the host cells the expressed first and second polypeptides.

The present disclosure provides a first nucleic acid that encodes a first polypeptide comprising an antibody heavy chain variable region having at least 95% sequence identity to the amino acid sequence of SEQ ID NO: 8, 10, 12, 14 or 22, and a second nucleic acid that encodes a second polypeptide comprising an antibody light chain variable region having at least 95% sequence identity to the amino acid sequence of SEQ ID NO: 9, 11, 13, 15, 16, 17, 18, 19, 20, 21 or 23.

The present disclosure provides a first vector operably linked to the first nucleic acid that encodes a first polypeptide comprising an antibody heavy chain variable region having at least 95% sequence identity to the amino acid sequence of SEQ ID NO: 8, 10, 12, 14 or 22, and a second vector is operably linked to the second nucleic acid which encodes the second polypeptide comprising the antibody light chain variable region having at least 95% sequence identity to the amino acid sequence of SEQ ID NO: 9, 11, 13, 15, 16, 17, 18, 19, 20, 21 or 23.

The present invention provides a host cell harboring the first vector operably linked to the first nucleic acid that encodes a first polypeptide comprising an antibody heavy chain variable region having at least 95% sequence identity to the amino acid sequence of SEQ ID NO: 8, 10, 12, 14 or 22, and the host cell harbors the second vector which is operably linked to the second nucleic acid which encodes the second polypeptide comprising the antibody light chain variable region having at least 95% sequence identity to the amino acid sequence of SEQ ID NO: 9, 11, 13, 15, 16, 17, 18, 19, 20, 21 or 23. In one embodiment, the first and second vectors comprise a first and second expression vector, respectively. In one embodiment, the host cell expresses the first polypeptide comprising an antibody heavy chain variable region having at least 95% sequence identity to the amino acid sequence of SEQ ID NO: 8, 10, 12, 14 or 22, and the host cell expresses the second polypeptide comprising the antibody light chain variable region having at least 95% sequence identity to the amino acid sequence of SEQ ID NO: 9, 11, 13, 15, 16, 17, 18, 19, 20, 21 or 23.

The present disclosure provides a method for preparing a first polypeptide having an antibody heavy chain variable region and a second polypeptide having an antibody light chain variable region, the method comprising: culturing a population (e.g., a plurality) of the host cells harboring the first and second expression vectors under conditions suitable for expressing the first polypeptide comprising an antibody heavy chain variable region having at least 95% sequence identity to the amino acid sequence of SEQ ID NO: 8, 10, 12, 14 or 22, and for expressing the second polypeptide having the antibody light chain variable region having at least 95% sequence identity to the amino acid sequence of SEQ ID NO: 9, 11, 13, 15, 16, 17, 18, 19, 20, 21 or 23. In one embodiment, the method further comprises: recovering from the population of the host cells the expressed first polypeptide comprising an antibody heavy chain variable region having at least 95% sequence identity to the amino acid sequence of SEQ ID NO: 8, 10, 12, 14 or 22, and the expressed second polypeptide having at least 95% sequence identity to the amino acid sequence of SEQ ID NO: 8, 10, 12, 14 or 22.

The present disclosure provides a nucleic acid that encodes a polypeptide (e.g., a single chain antibody including an scFv) comprising an antibody heavy chain variable region having heavy chain complementarity determining regions (HC-CDRs 1, 2 and 3) of any one of disclosed the human anti-BCMA antibodies, and an antibody light chain variable region having light chain complementarity determining regions (LC-CDRs 1, 2 and 3) of any one of disclosed the human anti-BCMA antibodies, wherein (a) the heavy chain CDR 1, 2 and 3 regions comprise the amino acid sequences of SEQ ID NOS:29, 30 and 31, respectively, and the light chain CDR 1, 2 and 3 regions comprise the amino acid sequences of SEQ ID NOS:32, 33 and 34, respectively; or (b) the heavy chain CDR 1, 2 and 3 regions comprise the amino acid sequences of SEQ ID NOS:35, 36 and 37, respectively, and the light chain CDR 1, 2 and 3 regions comprise the amino acid sequences of SEQ ID NOS:38, 39 and 40, respectively; or (c) the heavy chain CDR 1, 2 and 3 regions comprise the amino acid sequences of SEQ ID NOS:41, 42 and 43, respectively, and the light chain CDR 1, 2 and 3 regions comprise the amino acid sequences of SEQ ID NOS:44, 45 and 46, respectively; or (d) the heavy chain CDR 1, 2 and 3 regions comprise the amino acid sequences of SEQ ID NOS:47, 48 and 49, respectively, and the light chain CDR 1, 2 and 3 regions comprise the amino acid sequences of SEQ ID NOS:50, 51 and 52, respectively; or (e) the heavy chain CDR 1, 2 and 3 regions comprise the amino acid sequences of SEQ ID NOS:53, 54 and 55, respectively, and the light chain CDR 1, 2 and 3 regions comprise the amino acid sequences of SEQ ID NOS:56, 57 and 58, respectively; or (f) the heavy chain CDR 1, 2 and 3 regions comprise the amino acid sequences of SEQ ID NOS:59, 60 and 61, respectively, and the light chain CDR 1, 2 and 3 regions comprise the amino acid sequences of SEQ ID NOS:62, 63 and 64, respectively; or (g) the heavy chain CDR 1, 2 and 3 regions comprise the amino acid sequences of SEQ ID NOS:65, 66 and 67, respectively, and the light chain CDR 1, 2 and 3 regions comprise the amino acid sequences of SEQ ID NOS:68, 69 and 70, respectively; or (h) the heavy chain CDR 1, 2 and 3 regions comprise the amino acid sequences of SEQ ID NOS:71, 72 and 73, respectively, and the light chain CDR 1, 2 and 3 regions comprise the amino acid sequences of SEQ ID NOS:74, 75 and 76, respectively; or (i) the heavy chain CDR 1, 2 and 3 regions comprise the amino acid sequences of SEQ ID NOS:77, 78 and 79, respectively, and the light chain CDR 1, 2 and 3 regions comprise the amino acid sequences of SEQ ID NOS:80, 81 and 82, respectively; or (j) the heavy chain CDR 1, 2 and 3 regions comprise the amino acid sequences of SEQ ID NOS:83, 84 and 85, respectively, and the light chain CDR 1, 2 and 3 regions comprise the amino acid sequences of SEQ ID NOS:86, 87 and 88, respectively; or (k) the heavy chain CDR 1, 2 and 3 regions comprise the amino acid sequences of SEQ ID NOS:53, 54 and 55, respectively, and the light chain CDR 1, 2 and 3 regions comprise the amino acid sequences of SEQ ID NOS:89, 90 and 91, respectively.

The present disclosure provides a vector operably linked to the nucleic acid that encodes the polypeptide (e.g., a single chain antibody including an scFv) comprising the antibody heavy chain variable region having heavy chain complementarity determining regions (HC-CDRs 1, 2 and 3) of any one of disclosed the human anti-BCMA antibodies, and the antibody light chain variable region having light chain complementarity determining regions (LC-CDRs 1, 2 and 3) of any one of disclosed the human anti-BCMA antibodies.

The present disclosure provides a host cell harboring the vector which is operably linked to the nucleic acid that encodes the polypeptide (e.g., a single chain antibody including an scFv) comprising the antibody heavy chain variable region having heavy chain complementarity determining regions (HC-CDRs 1, 2 and 3) of any one of disclosed the human anti-BCMA antibodies, and the antibody light chain variable region having light chain complementarity determining regions (LC-CDRs 1, 2 and 3) of any one of disclosed the human anti-BCMA antibodies. In one embodiment, the vector comprises an expression vector. In one embodiment, the host cell expresses the polypeptide comprising the antibody heavy chain variable region having heavy chain complementarity determining regions (HC-CDRs 1, 2 and 3) of any one of disclosed the human anti-BCMA antibodies, and the antibody light chain variable region having light chain complementarity determining regions (LC-CDRs 1, 2 and 3) of any one of disclosed the human anti-BCMA antibodies.

The present disclosure provides a method for preparing the polypeptide, the method comprising: culturing a population (e.g., a plurality) of the host cell harboring the expression vector under conditions suitable for expressing the polypeptide comprising the antibody heavy chain variable region having heavy chain complementarity determining regions (HC-CDRs 1, 2 and 3) of any one of disclosed the human anti-BCMA antibodies, and the antibody light chain variable region having light chain complementarity determining regions (LC-CDRs 1, 2 and 3) of any one of disclosed the human anti-BCMA antibodies. In one embodiment, the method further comprises: recovering from the population of the host cells the expressed polypeptide.

The present disclosure provides a nucleic acid that encodes a polypeptide (e.g., a single chain antibody including an scFv) comprising an antibody heavy chain variable region having at least 95% sequence identity to the amino acid sequence of SEQ ID NO: 8, 10, 12, 14 or 22, and a an antibody light chain variable region having at least 95% sequence identity to the amino acid sequence of SEQ ID NO: 9, 11, 13, 15, 16, 17, 18, 19, 20, 21 or 23.

The present disclosure provides a vector operably linked to the nucleic acid that encodes the polypeptide (e.g., a single chain antibody including an scFv) comprising the antibody heavy chain variable region having at least 95% sequence identity to the amino acid sequence of SEQ ID NO: 8, 10, 12, 14 or 22, and the antibody light chain variable region having at least 95% sequence identity to the amino acid sequence of SEQ ID NO: 9, 11, 13, 15, 16, 17, 18, 19, 20, 21 or 23.

The present invention provides a host cell harboring the vector operably linked to the nucleic acid that encodes the polypeptide (e.g., a single chain antibody including an scFv) comprising the antibody heavy chain variable region having at least 95% sequence identity to the amino acid sequence of SEQ ID NO: 8, 10, 12, 14 or 22, and the antibody light chain variable region having at least 95% sequence identity to the amino acid sequence of SEQ ID NO: 9, 11, 13, 15, 16, 17, 18, 19, 20, 21 or 23. In one embodiment, the vector comprises an expression vector. In one embodiment, the host cell expresses the polypeptide (e.g., a single chain antibody including an scFv) comprising the antibody heavy chain variable region having at least 95% sequence identity to the amino acid sequence of SEQ ID NO: 8, 10, 12, 14 or 22, and the antibody light chain variable region having at least 95% sequence identity to the amino acid sequence of SEQ ID NO: 9, 11, 13, 15, 16, 17, 18, 19, 20, 21 or 23.

The present disclosure provides a method for preparing the polypeptide (e.g., a single chain antibody including an scFv), the method comprising: culturing a population (e.g., a plurality) of the host cells harboring the expression vector under conditions suitable for expressing the polypeptide (e.g., a single chain antibody including an scFv) comprising the antibody heavy chain variable region having at least 95% sequence identity to the amino acid sequence of SEQ ID NO: 8, 10, 12, 14 or 22, and the antibody light chain variable region having at least 95% sequence identity to the amino acid sequence of SEQ ID NO: 9, 11, 13, 15, 16, 17, 18, 19, 20, 21 or 23. In one embodiment, the method further comprises: recovering from the population of the host cells the expressed the polypeptide (e.g., a single chain antibody including an scFv) comprising the antibody heavy chain variable region having at least 95% sequence identity to the amino acid sequence of SEQ ID NO: 8, 10, 12, 14 or 22, and the antibody light chain variable region having at least 95% sequence identity to the amino acid sequence of SEQ ID NO: 9, 11, 13, 15, 16, 17, 18, 19, 20, 21 or 23.

The present disclosure provides a method (e.g., an in vitro method) for inhibiting growth or proliferation of BCMA-expressing cells, comprising: contacting (i) a population (e.g., a plurality) of effector cells with (ii) a population (e.g., a plurality) of target cells which express BCMA (iii) in the presence of any one or any combination of 2-3 of the human anti-BCMA antibodies described herein, under conditions that are suitable for inhibiting growth or proliferation of the BCMA-expressing cells. In one embodiment, the population of effector cells comprises PBMCs or NK cells. In one embodiment, the population of target cells comprise multiple myeloma (MM) cells expressing BCMA or transgenic cells expressing BCMA. In one embodiment, the ratio of the effector-to-target cells is 1:1, 2:1, 3:1, 4:1 or 5:1. In one embodiment, the ratio of the effector-to-target cells is 5-10:1, 10-20:1, or 20-30:1.

The present disclosure provides a method (e.g., an in vitro method) for killing BCMA-expressing cells, comprising: contacting (i) a population (e.g., a plurality) of effector cells with (ii) a population (e.g., a plurality) of target cells which express BCMA (iii) in the presence of any one or any combination of 2-3 of the human anti-BCMA antibodies described herein, under conditions that are suitable for killing the BCMA-expressing cells. In one embodiment, the population of effector cells comprises PBMCs or NK cells. In one embodiment, the population of target cells comprise a multiple myeloma (MM) cells expressing BCMA or transgenic cells expressing BCMA. In one embodiment, the ratio of the effector-to-target cells is 1:1, 2:1, 3:1, 4:1 or 5:1. In one embodiment, the ratio of the effector-to-target cells is 5-10:1, 10-20:1, or 20-30:1.

The present disclosure provides a method for treating a subject having a disease associated with BCMA over-expression, the method comprising: administering to the subject an effective amount of a therapeutic composition comprising any one or any combination of 2-3 of the human anti-BCMA antibodies described herein. In one embodiment, the disease associated with BCMA over-expression comprises: a B-cell leukemia, B-cell lymphoma or B-cell myeloma. In one embodiment, the disease associated with BCMA over-expression is selected from a group consisting of multiple myeloma (MM), non-Hodgkin's lymphoma (NHL) including Burkitt's lymphoma (BL), B chronic lymphocytic leukemia (B-CLL), systemic lupus erythematosus (SLE), B and T acute lymphocytic leukemia (ALL), acute myeloid leukemia (AML), chronic lymphocytic leukemia (CLL), diffuse large B cell lymphoma, chronic myelogenous leukemia (CIVIL), hairy cell leukemia (HCL), follicular lymphoma, Waldenstrom's Macroglobulinemia, mantle cell lymphoma, Hodgkin's Lymphoma (HL), plasma cell myeloma, precursor B cell lymphoblastic leukemia/lymphoma, plasmacytoma, giant cell myeloma, plasma cell myeloma, heavy-chain myeloma, light chain or Bence-Jones myeloma, lymphomatoid granulomatosis, post-transplant lymphoproliferative disorder, an immunoregulatory disorder, rheumatoid arthritis, myasthenia gravis, idiopathic thrombocytopenia purpura, anti-phospholipid syndrome, Chagas' disease, Grave's disease, Wegener's granulomatosis, poly-arteritis *nodosa*, Sjogren's syndrome, pemphigus vulgaris, scleroderma, multiple sclerosis, anti-phospholipid syndrome, ANCA associated vasculitis, Goodpasture's disease, Kawasaki disease, autoimmune hemolytic anemia, and rapidly progressive glomerulonephritis, heavy-chain disease, primary or immunocyte-associated amyloidosis, and monoclonal gammopathy of undetermined significance.

DESCRIPTION

Definitions

Figure 1:
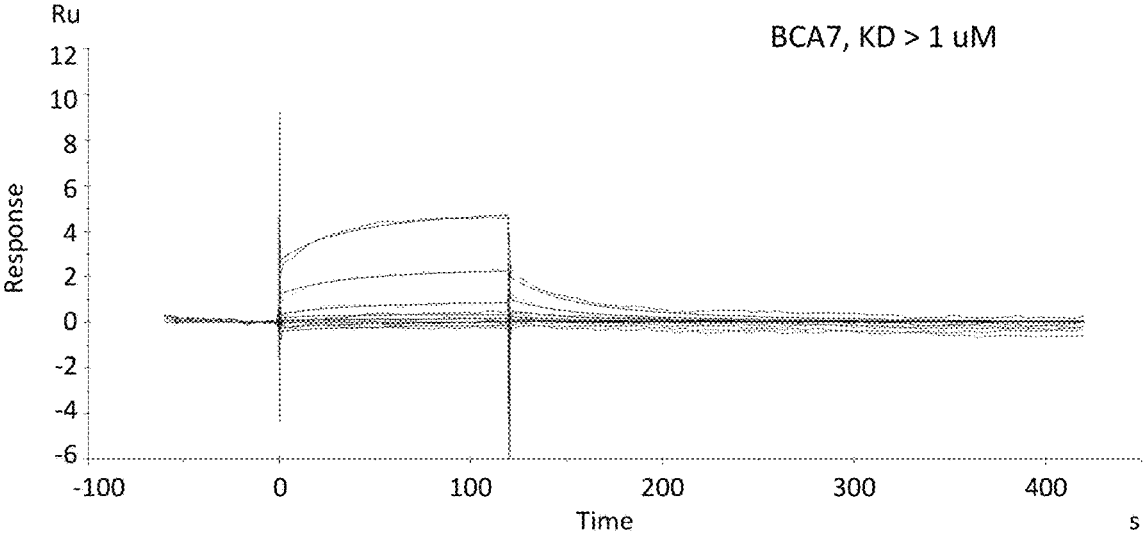
FIG. 1 shows an SPR sensorgram of binding kinetics of BCA7 antibody.
Figure 2:
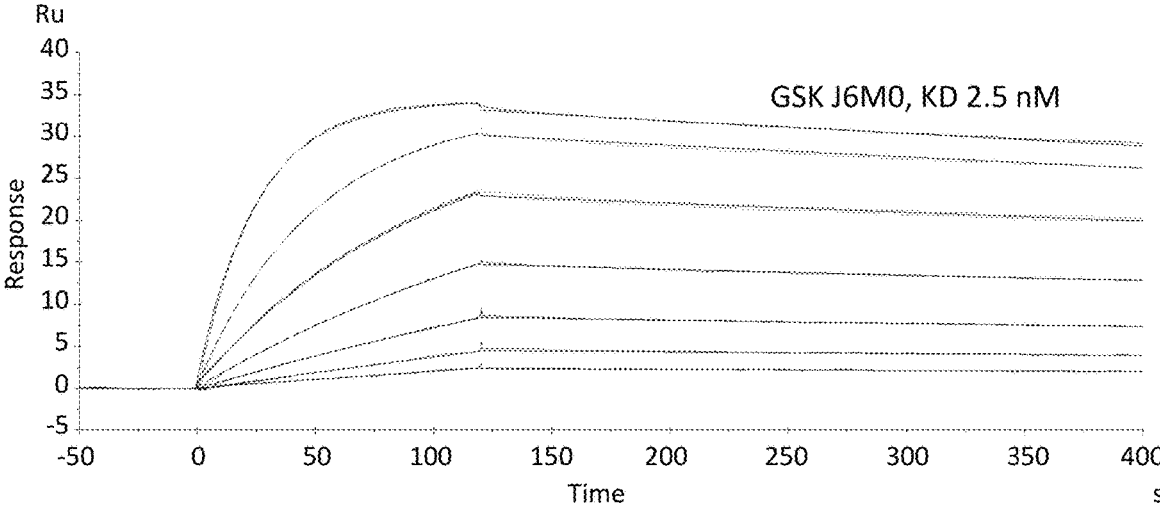
FIG. 2 shows an SPR sensorgram of binding kinetics of GSK J6M0 antibody.
Figure 3:
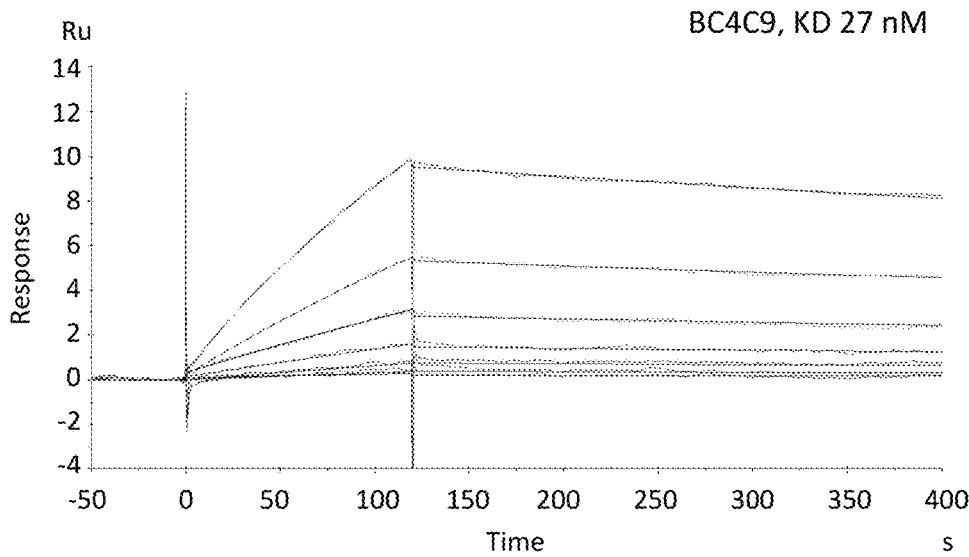
FIG. 3 shows an SPR sensorgram of binding kinetics of BC4C9 antibody.
Figure 4:
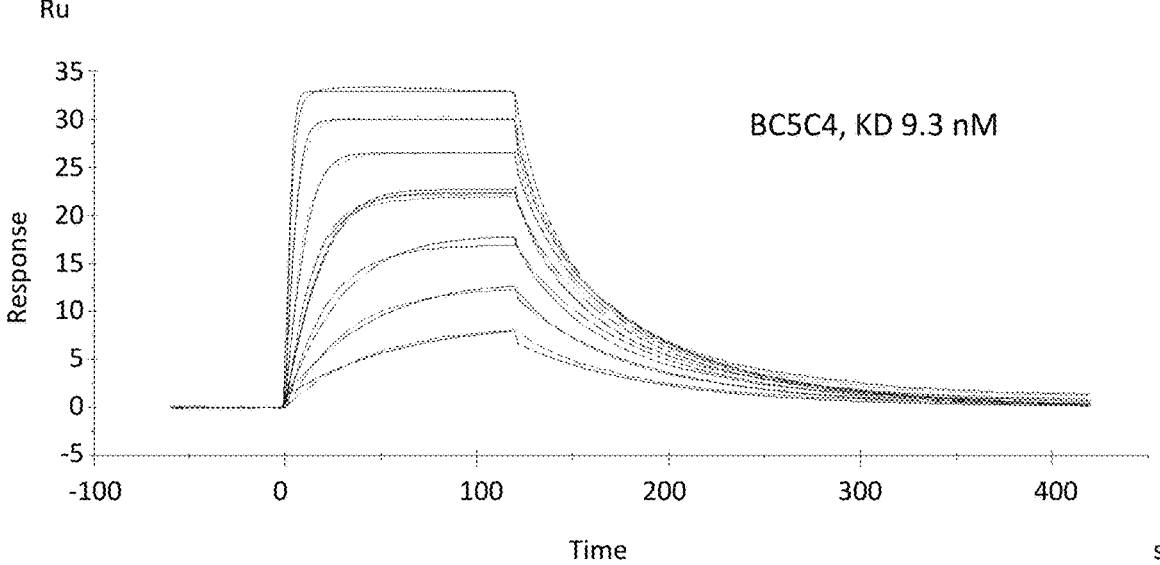
FIG. 4 shows an SPR sensorgram of binding kinetics of BC5C5 antibody.
Figures 5, 6:
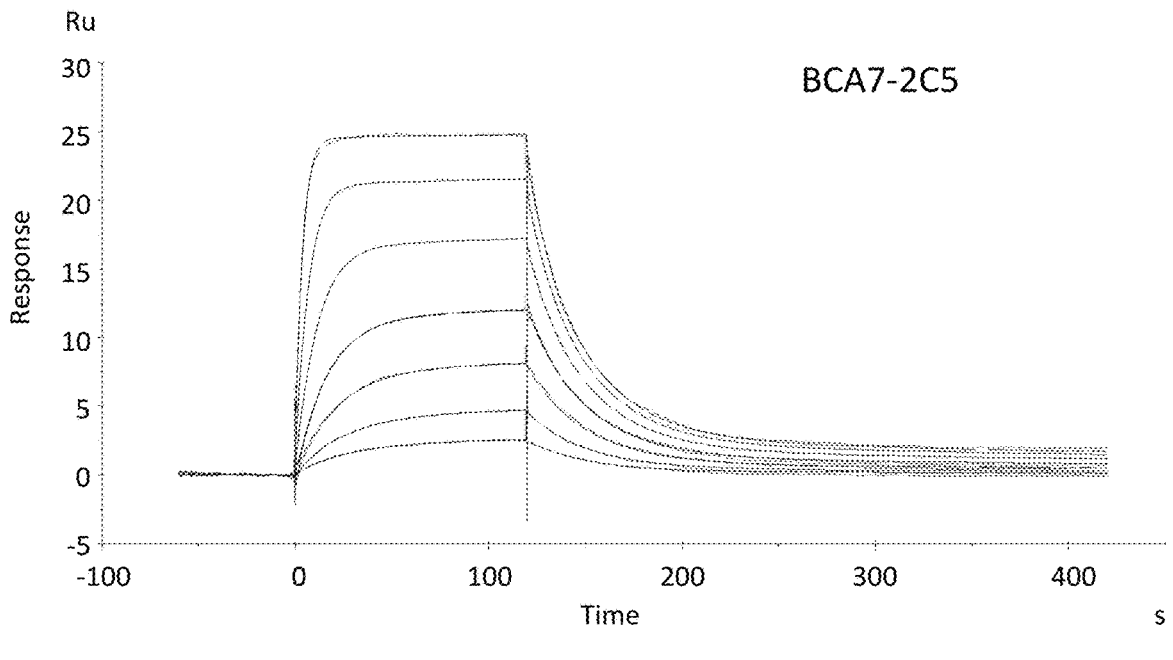
FIG. 5 shows an SPR sensorgram of binding kinetics of BCA7-2C5 antibody.
FIG. 6 shows an SPR sensorgram of binding kinetics of BCA7-2D11 antibody.
Figure 7:
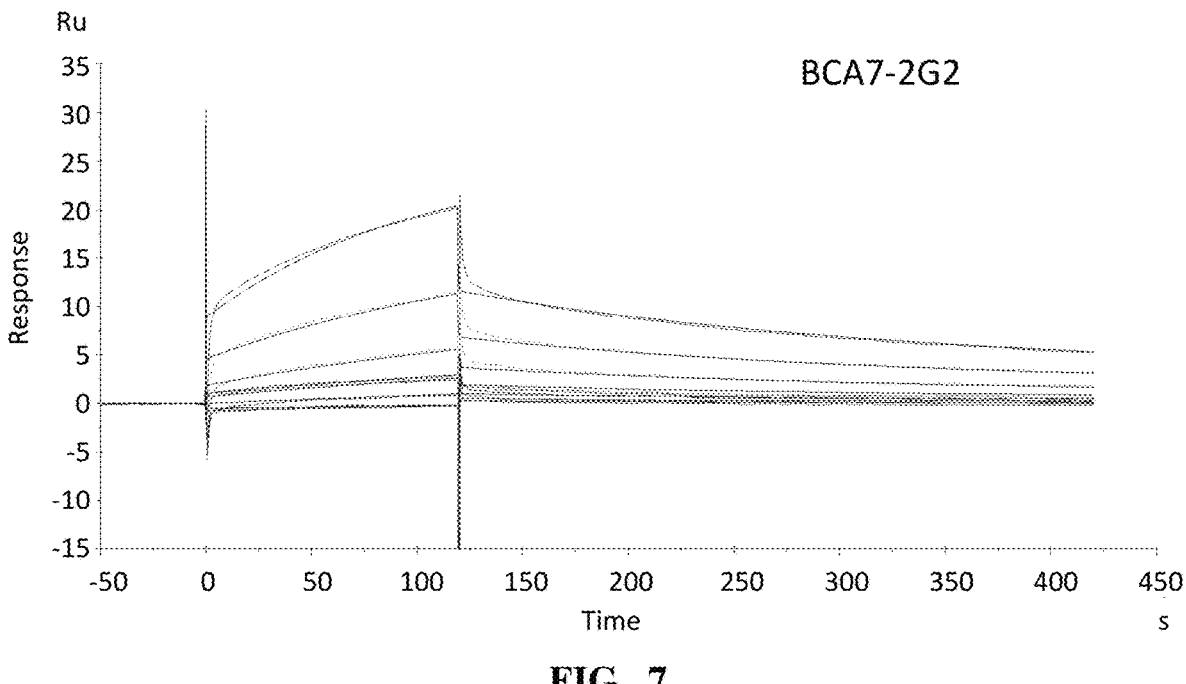
FIG. 7 shows an SPR sensorgram of binding kinetics of BCA7-2G2 antibody.
Figure 8:
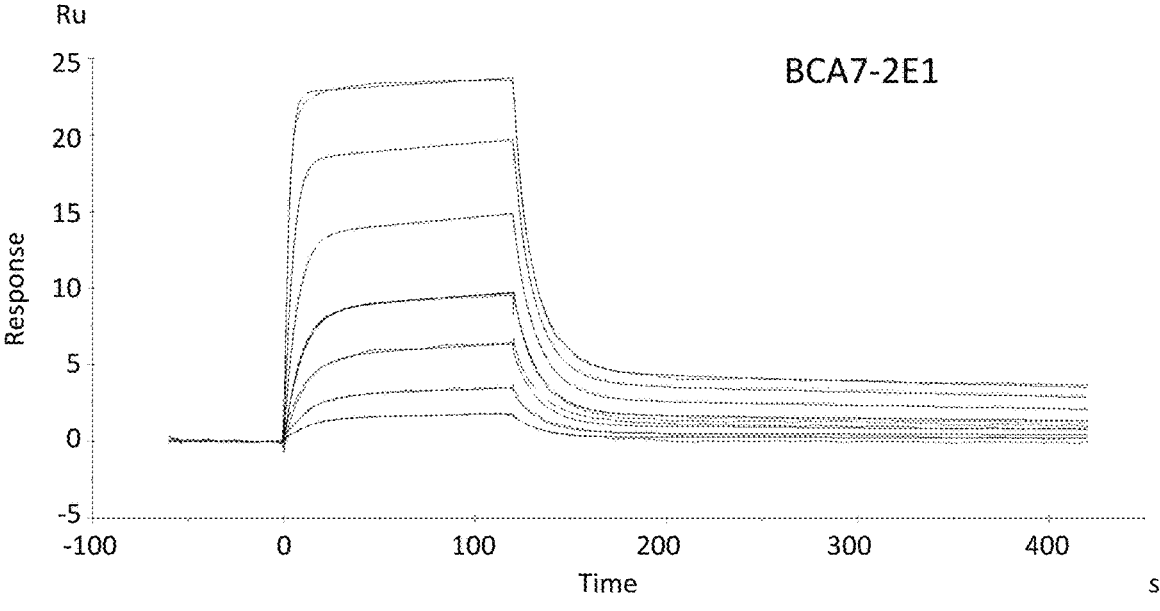
FIG. 8 shows an SPR sensorgram of binding kinetics of BCA7-2E1 antibody.
Figure 9:
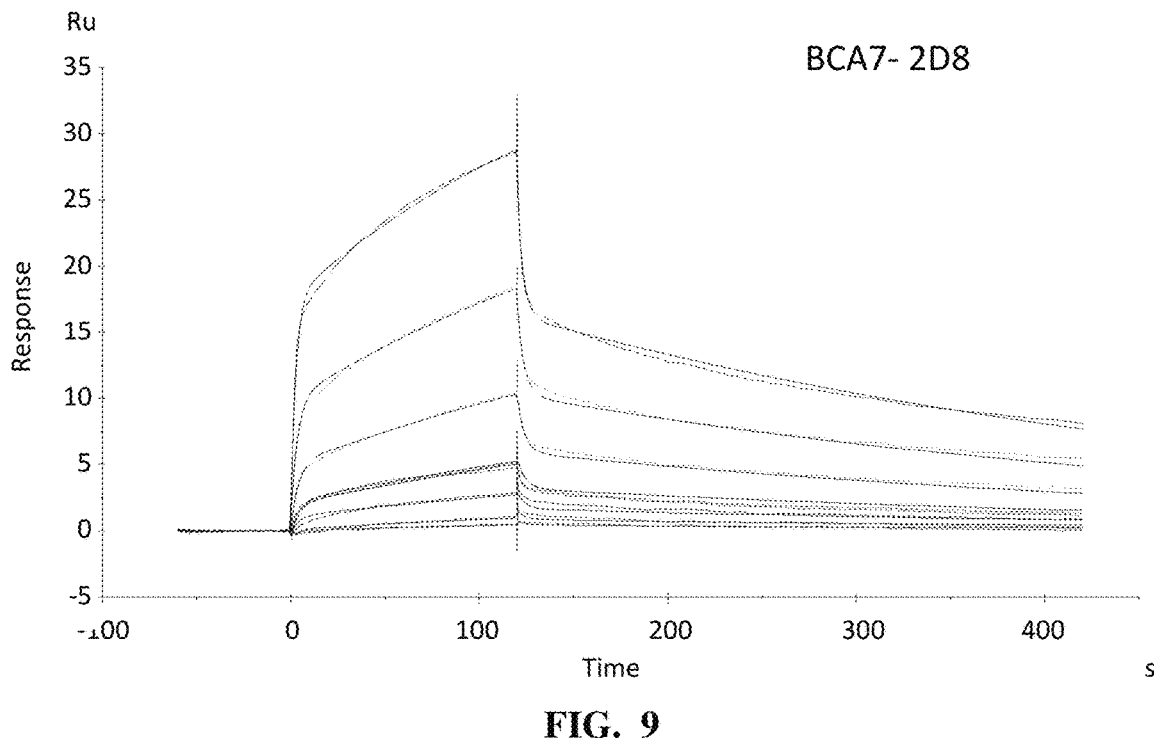
FIG. 9 shows an SPR sensorgram of binding kinetics of BCA7-2D8 antibody.
Figure 10:
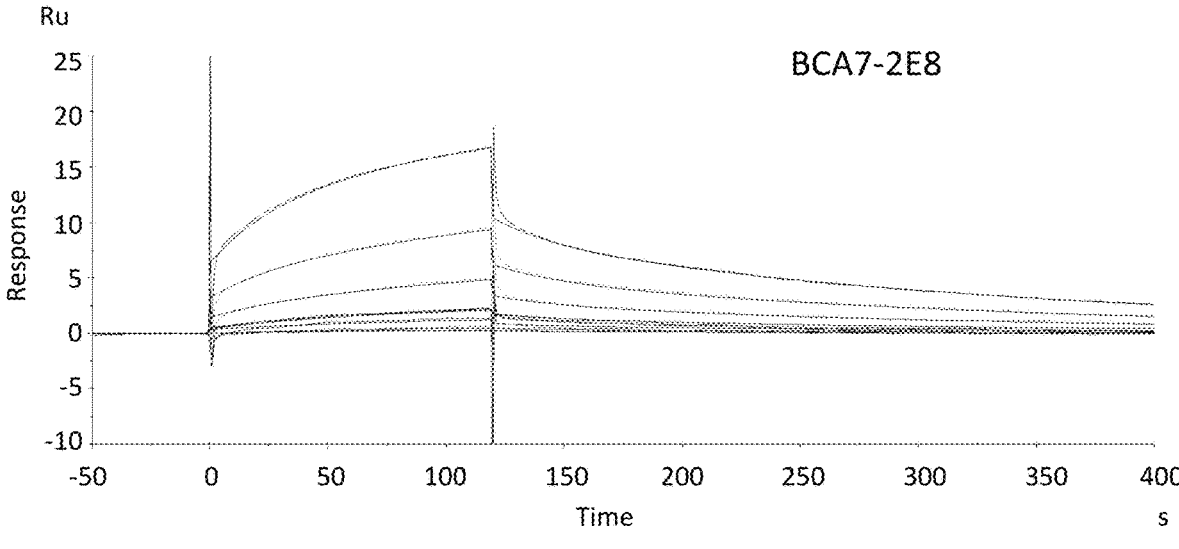
FIG. 10 shows an SPR sensorgram of binding kinetics of BCA7-2E81 antibody.

Unless defined otherwise, technical and scientific terms used herein have meanings that are commonly understood by those of ordinary skill in the art unless defined otherwise. Generally, terminologies pertaining to techniques of cell and tissue culture, molecular biology, immunology, microbiology, genetics, transgenic cell production, protein chemistry and nucleic acid chemistry and hybridization described herein are well known and commonly used in the art. The methods and techniques provided herein are generally performed according to conventional procedures well known in the art and as described in various general and more specific references that are cited and discussed herein unless otherwise indicated. See, e.g., Sambrook et al. Molecular Cloning: A Laboratory Manual, 2d ed., Cold Spring Harbor Laboratory Press, Cold Spring Harbor, N.Y. (1989) and Ausubel et al., Current Protocols in Molecular Biology, Greene Publishing Associates (1992). A number of basic texts describe standard antibody production processes, including, Borrebaeck (ed) *Antibody Engineering, 2nd Edition* Freeman and Company, N Y, 1995; McCafferty et al. *Antibody Engineering, A Practical Approach* IRL at Oxford Press, Oxford, England, 1996; and Paul (1995) *Antibody Engineering Protocols* Humana Press, Towata, N.J., 1995; Paul (ed.), *Fundamental Immunology*, Raven Press, N.Y, 1993; Coligan (1991) *Current Protocols in Immunology* Wiley/Greene, NY; Harlow and Lane (1989) *Antibodies: A Laboratory Manual* Cold Spring Harbor Press, NY; Stites et al. (eds.) Basic and Clinical Immunology (4th ed.) Lange Medical Publications, *Los Altos, Calif., and references* cited therein; *Coding Monoclonal Antibodies: Principles and Practice* (2nd ed.) Academic Press, New York, N.Y., 1986, and Kohler and Milstein *Nature* 256: 495-497, 1975. All of the references cited herein are incorporated herein by reference in their entireties. Enzymatic reactions and enrichment/purification techniques are also well known and are performed according to manufacturer's specifications, as commonly accomplished in the art or as described herein. The terminology used in connection with, and the laboratory procedures and techniques of, analytical chemistry, synthetic organic chemistry, and medicinal and pharmaceutical chemistry described herein are well known and commonly used in the art. Standard techniques can be used for chemical syntheses, chemical analyses, pharmaceutical preparation, formulation, and delivery, and treatment of patients.

The headings provided herein are not limitations of the various aspects of the disclosure, which aspects can be understood by reference to the specification as a whole.

Unless otherwise required by context herein, singular terms shall include pluralities and plural terms shall include the singular. Singular forms "a", "an" and "the", and singular use of any word, include plural referents unless expressly and unequivocally limited on one referent.

It is understood the use of the alternative (e.g., "or") herein is taken to mean either one or both or any combination thereof of the alternatives.

The term "and/or" used herein is to be taken mean specific disclosure of each of the specified features or components with or without the other. For example, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

As used herein, terms "comprising", "including", "having" and "containing", and their grammatical variants, as used herein are intended to be non-limiting so that one item or multiple items in a list do not exclude other items that can be substituted or added to the listed items. It is understood that wherever aspects are described herein with the language "comprising," otherwise analogous aspects described in terms of "consisting of" and/or "consisting essentially of" are also provided.

As used herein, the term "about" refers to a value or composition that is within an acceptable error range for the particular value or composition as determined by one of ordinary skill in the art, which will depend in part on how the value or composition is measured or determined, i.e., the limitations of the measurement system. For example, "about" or "comprising essentially of" can mean within one or more than one standard deviation per the practice in the art. Alternatively, "about" or "comprising essentially of" can mean a range of up to 10% (i.e., ±10%) or more depending on the limitations of the measurement system. For example, about 5 mg can include any number between 4.5 mg and 5.5 mg. Furthermore, particularly with respect to biological systems or processes, the terms can mean up to an order of magnitude or up to 5-fold of a value. When particular values or compositions are provided in the instant disclosure, unless otherwise stated, the meaning of "about" or "comprising essentially of" should be assumed to be within an acceptable error range for that particular value or composition.

The terms "peptide", "polypeptide" and "protein" and other related terms used herein are used interchangeably and refer to a polymer of amino acids and are not limited to any particular length. Polypeptides may comprise natural and non-natural amino acids. Polypeptides include recombinant or chemically-synthesized forms. These terms encompass native and artificial proteins, protein fragments and polypeptide analogs (such as muteins, variants, chimeric proteins and fusion proteins) of a protein sequence as well as post-translationally, or otherwise covalently or non-covalently, modified proteins. Polypeptides comprising amino acid sequences of binding proteins that bind BCMA (e.g., anti-BCMA antibodies or antigen-binding portions thereof) prepared using recombinant procedures are described herein.

The terms "nucleic acid", "polynucleotide" and "oligonucleotide" and other related terms used herein are used interchangeably and refer to polymers of nucleotides and are not limited to any particular length. Nucleic acids include recombinant and chemically-synthesized forms. Nucleic acids include DNA molecules (cDNA or genomic DNA), RNA molecules (e.g., mRNA), analogs of the DNA or RNA generated using nucleotide analogs (e.g., peptide nucleic acids and non-naturally occurring nucleotide analogs), and hybrids thereof. Nucleic acid molecule can be single-stranded or double-stranded. In one embodiment, the nucleic acid molecules of the disclosure comprise a contiguous open reading frame encoding an antibody, or a fragment or scFv, derivative, mutein, or variant thereof. In one embodiment, nucleic acids comprise a one type of polynucleotides or a mixture of two or more different types of polynucleotides. Nucleic acids encoding anti-BCMA antibodies or antigen-binding portions thereof, are described herein.

The term "recover" or "recovery" or "recovering", and other related terms, refers to obtaining a protein (e.g., an antibody or an antigen binding portion thereof), from host cell culture medium or from host cell lysate or from the host cell membrane. In one embodiment, the protein is expressed by the host cell as a recombinant protein fused to a secretion signal peptide sequence which mediates secretion of the expressed protein. The secreted protein can be recovered from the host cell medium. In one embodiment, the protein is expressed by the host cell as a recombinant protein that lacks a secretion signal peptide sequence which can be recovered from the host cell lysate. In one embodiment, the protein is expressed by the host cell as a membrane-bound protein which can be recovered using a detergent to release the expressed protein from the host cell membrane. In one embodiment, irrespective of the method used to recover the protein, the protein can be subjected to procedures that remove cellular debris from the recovered protein. For example, the recovered protein can be subjected to chromatography, gel electrophoresis and/or dialysis. In one embodiment, the chromatography comprises any one or any combination or two or more procedures including affinity chromatography, hydroxyapatite chromatography, ion-exchange chromatography, reverse phase chromatography and/or chromatography on silica. In one embodiment, affinity chromatography comprises protein A or G (cell wall components from *Staphylococcus aureus*).

The term "isolated" refers to a protein (e.g., an antibody or an antigen binding portion thereof) or polynucleotide that is substantially free of other cellular material. A protein may be rendered substantially free of naturally associated components (or components associated with a cellular expression system or chemical synthesis methods used to produce the antibody) by isolation, using protein purification techniques well known in the art. The term isolated also refers in some embodiments to protein or polynucleotides that are substantially free of other molecules of the same species, for example other protein or polynucleotides having different amino acid or nucleotide sequences, respectively. The purity of homogeneity of the desired molecule can be assayed using techniques well known in the art, including low resolution methods such as gel electrophoresis and high resolution methods such as HPLC or mass spectrophotometry. In one embodiment, any of the anti-BCMA antibodies or antigen binding protein thereof are isolated.

An "antigen binding protein" and related terms used herein refers to a protein comprising a portion that binds to an antigen and, optionally, a scaffold or framework portion that allows the antigen binding portion to adopt a conformation that promotes binding of the antigen binding protein to the antigen. Examples of antigen binding proteins include antibodies, antibody fragments (e.g., an antigen binding portion of an antibody), antibody derivatives, and antibody analogs. The antigen binding protein can comprise, for example, an alternative protein scaffold or artificial scaffold with grafted CDRs or CDR derivatives. Such scaffolds include, but are not limited to, antibody-derived scaffolds comprising mutations introduced to, for example, stabilize the three-dimensional structure of the antigen binding protein as well as wholly synthetic scaffolds comprising, for example, a biocompatible polymer. See, for example, Korndorfer et al., 2003, Proteins: Structure, Function, and Bioinformatics, Volume 53, Issue 1:121-129; Roque et al., 2004, Biotechnol. Prog. 20:639-654. In addition, peptide antibody mimetics ("PAMs") can be used, as well as scaffolds based on antibody mimetics utilizing fibronection components as a scaffold. Antigen binding proteins that bind BCMA are described herein.

An antigen binding protein can have, for example, the structure of an immunoglobulin. In one embodiment, an "immunoglobulin" refers to a tetrameric molecule composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa or lambda light chains. Heavy chains are classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ed., 2nd ed. Raven Press, N.Y. (1989)) (incorporated by reference in its entirety for all purposes). The variable regions of each light/heavy chain pair form the antibody binding site such that an intact immunoglobulin has two antigen binding sites. In one embodiment, an antigen binding protein can be a synthetic molecule having a structure that differs from a tetrameric immunoglobulin molecule but still binds a target antigen or binds two or more target antigens. For example, a synthetic antigen binding protein can comprise antibody fragments, 1-6 or more polypeptide chains, asymmetrical assemblies of polypeptides, or other synthetic molecules. Antigen binding proteins having immunoglobulin-like properties that bind specifically to BCMA are described herein.

The variable regions of immunoglobulin chains exhibit the same general structure of relatively conserved framework regions (FR) joined by three hypervariable regions, also called complementarity determining regions or CDRs. From N-terminus to C-terminus, both light and heavy chains comprise the domains FR1, CDR1, FR2, CDR2, FR3, CDR3 and FR4.

One or more CDRs may be incorporated into a molecule either covalently or noncovalently to make it an antigen binding protein. An antigen binding protein may incorporate the CDR(s) as part of a larger polypeptide chain, may covalently link the CDR(s) to another polypeptide chain, or may incorporate the CDR(s) noncovalently. The CDRs permit the antigen binding protein to specifically bind to a particular antigen of interest.

The assignment of amino acids to each domain is in accordance with the definitions of Kabat et al. in Sequences of Proteins of Immunological Interest, 5th Ed., US Dept. of Health and Human Services, PHS, NIH, NIH Publication no. 91-3242, 1991. Other numbering systems for the amino acids in immunoglobulin chains include IMGT® (international ImMunoGeneTics information system; Lefranc et al, Dev. Comp. Immunol. 29:185-203; 2005) and AHo (Honegger and Pluckthun, J. Mol. Biol. 309(3):657-670; 2001); Chothia (Al-Lazikani et al., 1997 Journal of Molecular Biology 273:927-948; Contact (Maccallum et al., 1996 Journal of Molecular Biology 262:732-745, and Aho (Honegger and Pluckthun 2001 Journal of Molecular Biology 309:657-670.

An "antibody" and "antibodies" and related terms used herein refers to an intact immunoglobulin or to an antigen binding portion thereof (or an antigen binding fragment thereof) that binds specifically to an antigen. Antigen binding portions (or the antigen binding fragment) may be produced by recombinant DNA techniques or by enzymatic or chemical cleavage of intact antibodies. Antigen binding portions (or antigen binding fragments) include, inter alia, Fab, Fab', F(ab')2, Fv, domain antibodies (dAbs), and complementarity determining region (CDR) fragments, single-chain antibodies (scFv), chimeric antibodies, diabodies, triabodies, tetrabodies, and polypeptides that contain at least a portion of an immunoglobulin that is sufficient to confer specific antigen binding to the polypeptide.

Antibodies include recombinantly produced antibodies and antigen binding portions. Antibodies include non-human, chimeric, humanized and fully human antibodies. Antibodies include monospecific, multispecific (e.g., bispecific, trispecific and higher order specificities). Antibodies include tetrameric antibodies, light chain monomers, heavy chain monomers, light chain dimers, heavy chain dimers. Antibodies include F(ab')2 fragments, Fab' fragments and Fab fragments. Antibodies include single domain antibodies, monovalent antibodies, single chain antibodies, single chain variable fragment (scFv), camelized antibodies, affibodies, disulfide-linked Fvs (sdFv), anti-idiotypic antibodies (anti-Id), minibodies. Antibodies include monoclonal and polyclonal populations. Anti-BCMA antibodies are described herein.

An "antigen binding domain," "antigen binding region," or "antigen binding site" and other related terms used herein refer to a portion of an antigen binding protein that contains amino acid residues (or other moieties) that interact with an antigen and contribute to the antigen binding protein's specificity and affinity for the antigen. For an antibody that specifically binds to its antigen, this will include at least part of at least one of its CDR domains. Antigen binding domains from anti-BCMA antibodies are described herein.

The terms "specific binding", "specifically binds" or "specifically binding" and other related terms, as used herein in the context of an antibody or antigen binding protein or antibody fragment, refer to non-covalent or covalent preferential binding to an antigen relative to other molecules or moieties (e.g., an antibody specifically binds to a particular antigen relative to other available antigens). In one embodiment, an antibody specifically binds to a target antigen if it binds to the antigen with a dissociation constant $K_D$ of $10^{-5}$ M or less, or $10^{-6}$ M or less, or $10^{-7}$ M or less, or $10^{-8}$ M or less, or $10^{-9}$M or less, or $10^{-10}$ M or less. Anti-BCMA antibodies that specifically bind BCMA are described herein.

In one embodiment, a dissociation constant ($K_D$) can be measured using a BIACORE surface plasmon resonance (SPR) assay. Surface plasmon resonance refers to an optical phenomenon that allows for the analysis of real-time interactions by detection of alterations in protein concentrations within a biosensor matrix, for example using the BIACORE system (Biacore Life Sciences division of GE Healthcare, Piscataway, NJ).

An "epitope" and related terms as used herein refers to a portion of an antigen that is bound by an antigen binding protein (e.g., by an antibody or an antigen binding portion thereof). An epitope can comprise portions of two or more antigens that are bound by an antigen binding protein. An epitope can comprise non-contiguous portions of an antigen or of two or more antigens (e.g., amino acid residues that are not contiguous in an antigen's primary sequence but that, in the context of the antigen's tertiary and quaternary structure, are near enough to each other to be bound by an antigen binding protein). Generally, the variable regions, particularly the CDRs, of an antibody interact with the epitope. Anti-BCMA antibodies, and antigen binding proteins thereof, that bind an epitope of a BCMA polypeptide are described herein.

An "antibody fragment", "antibody portion", "antigen-binding fragment of an antibody", or "antigen-binding portion of an antibody" and other related terms used herein refer to a molecule other than an intact antibody that comprises a portion of an intact antibody that binds the antigen to which the intact antibody binds. Examples of antibody fragments include, but are not limited to, Fv, Fab, Fab', Fab'-SH, F(ab')2; Fd; and Fv fragments, as well as dAb; diabodies; linear antibodies; single-chain antibody molecules (e.g. scFv); polypeptides that contain at least a portion of an antibody that is sufficient to confer specific antigen binding to the polypeptide. Antigen binding portions of an antibody may be produced by recombinant DNA techniques or by enzymatic or chemical cleavage of intact antibodies. Antigen binding portions include, inter alia, Fab, Fab', F(ab')2, Fv, domain antibodies (dAbs), and complementarity determining region (CDR) fragments, chimeric antibodies, diabodies, triabodies, tetrabodies, and polypeptides that contain at least a portion of an immunoglobulin that is sufficient to confer antigen binding properties to the antibody fragment. Antigen-binding fragments of anti-BCMA antibodies are described herein.

The terms "Fab", "Fab fragment" and other related terms refers to a monovalent fragment comprising a variable light chain region ($V_L$), constant light chain region ($C_L$), variable heavy chain region ($V_H$), and first constant region ($C_{H1}$). A Fab is capable of binding an antigen. An F(ab')$_2$ fragment is a bivalent fragment comprising two Fab fragments linked by a disulfide bridge at the hinge region. A F(Ab')$_2$ has antigen binding capability. An Fd fragment comprises $V_H$ and Cm regions. An Fv fragment comprises $V_L$ and $V_H$ regions. An Fv can bind an antigen. A dAb fragment has a $V_H$ domain, a $V_L$ domain, or an antigen-binding fragment of a $V_H$ or $V_L$ domain (U.S. Pat. Nos. 6,846,634 and 6,696,245; U.S. published Application Nos. 2002/02512, 2004/0202995, 2004/0038291, 2004/0009507, 2003/0039958; and Ward et al., Nature 341:544-546, 1989). Fab fragments comprising antigen binding portions from anti-BCMA antibodies are described herein.

A single-chain antibody (scFv) is an antibody in which a $V_L$ and a $V_H$ region are joined via a linker (e.g., a synthetic sequence of amino acid residues) to form a continuous protein chain. Preferably the linker is long enough to allow the protein chain to fold back on itself and form a monovalent antigen binding site (see, e.g., Bird et al., 1988, Science 242:423-26 and Huston et al., 1988, Proc. Natl. Acad. Sci. USA 85:5879-83). Single chain antibodies comprising antigen binding portions from anti-BCMA antibodies are described herein.

Diabodies are bivalent antibodies comprising two polypeptide chains, wherein each polypeptide chain comprises $V_H$ and $V_L$ domains joined by a linker that is too short to allow for pairing between two domains on the same chain, thus allowing each domain to pair with a complementary domain on another polypeptide chain (see, e.g., Holliger et al., 1993, Proc. Natl. Acad. Sci. USA 90:6444-48, and Poljak et al., 1994, Structure 2:1121-23). If the two polypeptide chains of a diabody are identical, then a diabody resulting from their pairing will have two identical antigen binding sites. Polypeptide chains having different sequences can be used to make a diabody with two different antigen binding sites. Similarly, tribodies and tetrabodies are antibodies comprising three and four polypeptide chains, respectively, and forming three and four antigen binding sites, respectively, which can be the same or different. Diabody, tribody and tetrabody constructs can be prepared using antigen binding portions from any of the anti-BCMA antibodies described herein.

The term "human antibody" refers to antibodies that have one or more variable and constant regions derived from human immunoglobulin sequences. In one embodiment, all of the variable and constant domains are derived from human immunoglobulin sequences (e.g., a fully human antibody). These antibodies may be prepared in a variety of ways, examples of which are described below, including through recombinant methodologies or through immunization with an antigen of interest of a mouse that is genetically modified to express antibodies derived from human heavy and/or light chain-encoding genes. Fully human anti-BCMA antibodies and antigen binding proteins thereof are described herein.

A "humanized" antibody refers to an antibody having a sequence that differs from the sequence of an antibody derived from a non-human species by one or more amino acid substitutions, deletions, and/or additions, such that the humanized antibody is less likely to induce an immune response, and/or induces a less severe immune response, as compared to the non-human species antibody, when it is administered to a human subject. In one embodiment, certain amino acids in the framework and constant domains of the heavy and/or light chains of the non-human species antibody are mutated to produce the humanized antibody. In another embodiment, the constant domain(s) from a human antibody are fused to the variable domain(s) of a non-human species. In another embodiment, one or more amino acid residues in one or more CDR sequences of a non-human antibody are changed to reduce the likely immunogenicity of the non-human antibody when it is administered to a human subject, wherein the changed amino acid residues either are not critical for immunospecific binding of the antibody to its antigen, or the changes to the amino acid sequence that are made are conservative changes, such that the binding of the humanized antibody to the antigen is not significantly worse than the binding of the non-human antibody to the antigen. Examples of how to make humanized antibodies may be found in U.S. Pat. Nos. 6,054,297, 5,886,152 and 5,877,293.

The term "chimeric antibody" and related terms used herein refers to an antibody that contains one or more regions from a first antibody and one or more regions from one or more other antibodies. In one embodiment, one or more of the CDRs are derived from a human antibody. In another embodiment, all of the CDRs are derived from a human antibody. In another embodiment, the CDRs from more than one human antibody are mixed and matched in a chimeric antibody. For instance, a chimeric antibody may comprise a CDR1 from the light chain of a first human antibody, a CDR2 and a CDR3 from the light chain of a second human antibody, and the CDRs from the heavy chain from a third antibody. In another example, the CDRs originate from different species such as human and mouse, or human and rabbit, or human and goat. One skilled in the art will appreciate that other combinations are possible.

Further, the framework regions may be derived from one of the same antibodies, from one or more different antibodies, such as a human antibody, or from a humanized antibody. In one example of a chimeric antibody, a portion of the heavy and/or light chain is identical with, homologous to, or derived from an antibody from a particular species or belonging to a particular antibody class or subclass, while the remainder of the chain(s) is/are identical with, homologous to, or derived from an antibody (-ies) from another species or belonging to another antibody class or subclass. Also included are fragments of such antibodies that exhibit the desired biological activity (i.e., the ability to specifically bind a target antigen). Chimeric antibodies can be prepared from portions of any of the anti-BCMA antibodies described herein.

As used herein, the term "variant" polypeptides and "variants" of polypeptides refers to a polypeptide comprising an amino acid sequence with one or more amino acid residues inserted into, deleted from and/or substituted into the amino acid sequence relative to a reference polypeptide sequence. Polypeptide variants include fusion proteins. In the same manner, a variant polynucleotide comprises a nucleotide sequence with one or more nucleotides inserted into, deleted from and/or substituted into the nucleotide sequence relative to another polynucleotide sequence. Polynucleotide variants include fusion polynucleotides.

As used herein, the term "derivative" of a polypeptide is a polypeptide (e.g., an antibody) that has been chemically modified, e.g., via conjugation to another chemical moiety such as, for example, polyethylene glycol, albumin (e.g., human serum albumin), phosphorylation, and glycosylation. Unless otherwise indicated, the term "antibody" includes, in addition to antibodies comprising two full-length heavy chains and two full-length light chains, derivatives, variants, fragments, and muteins thereof, examples of which are described below.

The term "Fc" or "Fc region" as used herein refers to the portion of an antibody heavy chain constant region beginning in or after the hinge region and ending at the C-terminus of the heavy chain. The Fc region comprises at least a portion of the CH and CH3 regions and may, or may not, include a portion of the hinge region. Two polypeptide chains each carrying a half Fc region can dimerize to form a full Fc domain. An Fc domain can bind Fc cell surface receptors and some proteins of the immune complement system. An Fc domain exhibits effector function, including any one or any combination of two or more activities including complement-dependent cytotoxicity (CDC), antibody-dependent cell-mediated cytotoxicity (ADCC), antibody-dependent phagocytosis (ADP), opsonization and/or cell binding. An Fc domain can bind an Fc receptor, including FcγRT (e.g., CD64), FcγRII (e.g, CD32) and/or FcγRIII (e.g., CD16a).

The term "labeled antibody" or related terms as used herein refers to antibodies and their antigen binding portions thereof that are unlabeled or joined to a detectable label or moiety for detection, wherein the detectable label or moiety is radioactive, colorimetric, antigenic, enzymatic, a detectable bead (such as a magnetic or electrodense (e.g., gold) bead), biotin, streptavidin or protein A. A variety of labels can be employed, including, but not limited to, radionuclides, fluorescers, enzymes, enzyme substrates, enzyme cofactors, enzyme inhibitors and ligands (e.g., biotin, haptens). Any of the anti-BCMA antibodies described herein can be unlabeled or can be joined to a detectable label or moiety.

The "percent identity" or "percent homology" and related terms used herein refers to a quantitative measurement of the similarity between two polypeptide or between two polynucleotide sequences. The percent identity between two polypeptide sequences is a function of the number of identical amino acids at aligned positions that are shared between the two polypeptide sequences, taking into account the number of gaps, and the length of each gap, which may need to be introduced to optimize alignment of the two polypeptide sequences. In a similar manner, the percent identity between two polynucleotide sequences is a function of the number of identical nucleotides at aligned positions that are shared between the two polynucleotide sequences, taking into account the number of gaps, and the length of each gap, which may need to be introduced to optimize alignment of the two polynucleotide sequences. A comparison of the sequences and determination of the percent identity between two polypeptide sequences, or between two polynucleotide sequences, may be accomplished using a mathematical algorithm. For example, the "percent identity" or "percent homology" of two polypeptide or two polynucleotide sequences may be determined by comparing the sequences using the GAP computer program (a part of the GCG Wisconsin Package, version 10.3 (Accelrys, San Diego, Calif.)) using its default parameters.

In one embodiment, the amino acid sequence of a test antibody may be similar but not identical to any of the amino acid sequences of the polypeptides that make up any of the anti-BCMA antibodies, or antigen binding protein thereof, described herein. The similarities between the test antibody and the polypeptides can be at least 95%, or at or at least 96% identical, or at least 97% identical, or at least 98% identical, or at least 99% identical, to any of the polypeptides that make up any of the anti-BCMA antibodies, or antigen binding protein thereof, described herein. In one embodiment, similar polypeptides can contain amino acid substitutions within a heavy and/or light chain. In one embodiment, the amino acid substitutions comprise one or more conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24: 307-331, herein incorporated by reference in its entirety. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine.

Antibodies can be obtained from sources such as serum or plasma that contain immunoglobulins having varied antigenic specificity. If such antibodies are subjected to affinity purification, they can be enriched for a particular antigenic specificity. Such enriched preparations of antibodies usually are made of less than about 10% antibody having specific binding activity for the particular antigen. Subjecting these preparations to several rounds of affinity purification can increase the proportion of antibody having specific binding activity for the antigen. Antibodies prepared in this manner are often referred to as "monospecific." Monospecific antibody preparations can be made up of about 10%, 20%, 30%, 40%, 50%, 60%, 70%, 75%, 80%, 85%, 90%, 95%, 97%, 99%, or 99.9% antibody having specific binding activity for the particular antigen. Antibodies can be produced using recombinant nucleic acid technology as described below.

A "vector" and related terms used herein refers to a nucleic acid molecule (e.g., DNA or RNA) which can be operably linked to foreign genetic material (e.g., nucleic acid transgene). Vectors can be used as a vehicle to introduce foreign genetic material into a cell (e.g., host cell). Vectors can include at least one restriction endonuclease recognition sequence for insertion of the transgene into the vector. Vectors can include at least one gene sequence that confers antibiotic resistance or a selectable characteristic to aid in selection of host cells that harbor a vector-transgene construct. Vectors can be single-stranded or double-stranded nucleic acid molecules. Vectors can be linear or circular nucleic acid molecules. One type of vector is a "plasmid," which refers to a linear or circular double stranded extrachromosomal DNA molecule which can be linked to a transgene, and is capable of replicating in a host cell, and transcribing and/or translating the transgene. A viral vector typically contains viral RNA or DNA backbone sequences which can be linked to the transgene. The viral backbone sequences can be modified to disable infection but retain insertion of the viral backbone and the co-linked transgene into a host cell genome. Examples of viral vectors include retroviral, lentiviral, adenoviral, adeno-associated, baculoviral, papovaviral, vaccinia viral, herpes simplex viral and Epstein Barr viral vectors. Certain vectors are capable of autonomous replication in a host cell into which they are introduced (e.g., bacterial vectors comprising a bacterial origin of replication and episomal mammalian vectors). Other vectors (e.g., non-episomal mammalian vectors) are integrated into the genome of a host cell upon introduction into the host cell, and thereby are replicated along with the host genome.

An "expression vector" is a type of vector that can contain one or more regulatory sequences, such as inducible and/or constitutive promoters and enhancers. Expression vectors can include ribosomal binding sites and/or polyadenylation sites. Regulatory sequences direct transcription, or transcription and translation, of a transgene linked to the expression vector which is transduced into a host cell. The regulatory sequence(s) can control the level, timing and/or location of expression of the transgene. The regulatory sequence can, for example, exert its effects directly on the transgene, or through the action of one or more other molecules (e.g., polypeptides that bind to the regulatory sequence and/or the nucleic acid). Regulatory sequences can be part of a vector. Further examples of regulatory sequences are described in, for example, Goeddel, 1990, Gene Expression Technology: Methods in Enzymology 185, Academic Press, San Diego, Calif. and Baron et al., 1995, Nucleic Acids Res. 23:3605-3606. An expression vector can comprise at least a portion of any of the anti-BCMA antibodies described herein.

A transgene is "operably linked" to a vector when there is linkage between the transgene and the vector to permit functioning or expression of the transgene sequences contained in the vector. In one embodiment, a transgene is "operably linked" to a regulatory sequence when the regulatory sequence affects the expression (e.g., the level, timing, or location of expression) of the transgene.

The terms "transfected" or "transformed" or "transduced" or other related terms used herein refer to a process by which exogenous nucleic acid (e.g., transgene) is transferred or introduced into a host cell. A "transfected" or "transformed" or "transduced" host cell is one which has been transfected, transformed or transduced with exogenous nucleic acid (transgene). The host cell includes the primary subject cell and its progeny. Exogenous nucleic acids encoding at least a portion of any of the anti-BCMA antibodies described herein can be introduced into a host cell. Expression vectors comprising at least a portion of any of the anti-BCMA antibodies described herein can be introduced into a host cell, and the host cell can express polypeptides comprising at least a portion of the anti-BCMA antibody.

The terms "host cell" or "or a population of host cells" or related terms as used herein refer to a cell (or a population thereof or a plurality of a host cell) into which foreign (exogenous or transgene) nucleic acids have been introduced. The foreign nucleic acids can include an expression vector operably linked to a transgene, and the host cell can be used to express the nucleic acid and/or polypeptide encoded by the foreign nucleic acid (transgene). A host cell (or a population thereof) can be a cultured cell or can be extracted from a subject. The host cell (or a population thereof) includes the primary subject cell and its progeny without any regard for the number of passages. Progeny cells may or may not harbor identical genetic material compared to the parent cell. Host cells encompass progeny cells. In one embodiment, a host cell describes any cell (including its progeny) that has been modified, transfected, transduced, transformed, and/or manipulated in any way to express an antibody, as disclosed herein. In one example, the host cell (or population thereof) can be introduced with an expression vector operably linked to a nucleic acid encoding the desired antibody, or an antigen binding portion thereof, described herein. Host cells and populations thereof can harbor an expression vector that is stably integrated into the host's genome or can harbor an extrachromosomal expression vector. In one embodiment, host cells and populations thereof can harbor an extrachromosomal vector that is present after several cell divisions or is present transiently and is lost after several cell divisions.

A host cell can be a prokaryote, for example, E. coli, or it can be a eukaryote, for example, a single-celled eukaryote (e.g., a yeast or other fungus), a plant cell (e.g., a tobacco or tomato plant cell), an mammalian cell (e.g., a human cell, a monkey cell, a hamster cell, a rat cell, a mouse cell, or an insect cell) or a hybridoma. In one embodiment, a host cell can be introduced with an expression vector operably linked to a nucleic acid encoding a desired antibody thereby generating a transfected/transformed host cell which is cultured under conditions suitable for expression of the antibody by the transfected/transformed host cell, and optionally recovering the antibody from the transfected/transformed host cells (e.g., recovery from host cell lysate) or recovery from the culture medium. In one embodiment, host cells comprise non-human cells including CHO, BHK, NS0, SP2/0, and YB2/0. In one embodiment, host cells comprise human cells including HEK293, HT-1080, Huh-7 and PER.C6. Examples of host cells include the COS-7 line of monkey kidney cells (ATCC CRL 1651) (see Gluzman et al., 1981, Cell 23: 175), L cells, C127 cells, 3T3 cells (ATCC CCL 163), Chinese hamster ovary (CHO) cells or their derivatives such as Veggie CHO and related cell lines which grow in serum-free media (see Rasmussen et al., 1998, Cytotechnology 28:31) or CHO strain DX-B 11, which is deficient in DHFR (see Urlaub et al., 1980, Proc. Natl. Acad. Sci. USA 77:4216-20), HeLa cells, BHK (ATCC CRL 10) cell lines, the CV1/EBNA cell line derived from the African green monkey kidney cell line CV1 (ATCC CCL 70) (see McMahan et al., 1991, EMBO J. 10:2821), human embryonic kidney cells such as 293, 293 EBNA or MSR 293, human epidermal A431 cells, human Colo 205 cells, other transformed primate cell lines, normal diploid cells, cell strains derived from in vitro culture of primary tissue, primary explants, HL-60, U937, HaK or Jurkat cells. In one embodiment, host cells include lymphoid cells such as Y0, NS0 or Sp20. In one embodiment, a host cell is a mammalian host cell, but is not a human host cell. Typically, a host cell is a cultured cell that can be transformed or transfected with a polypeptide-encoding nucleic acid, which can then be expressed in the host cell. The phrase "transgenic host cell" or "recombinant host cell" can be used to denote a host cell that has been transformed or transfected with a nucleic acid to be expressed. A host cell also can be a cell that comprises the nucleic acid but does not express it at a desired level unless a regulatory sequence is introduced into the host cell such that it becomes operably linked with the nucleic acid. It is understood that the term host cell refers not only to the particular subject cell but also to the progeny or potential progeny of such a cell. Because certain modifications may occur in succeeding generations due to, e.g., mutation or environmental influence, such progeny may not, in fact, be identical to the parent cell, but are still included within the scope of the term as used herein.

Polypeptides of the present disclosure (e.g., antibodies and antigen binding proteins) can be produced using any methods known in the art. In one example, the polypeptides are produced by recombinant nucleic acid methods by inserting a nucleic acid sequence (e.g., DNA) encoding the polypeptide into a recombinant expression vector which is introduced into a host cell and expressed by the host cell under conditions promoting expression.

General techniques for recombinant nucleic acid manipulations are described for example in Sambrook et al., in *Molecular Cloning: A Laboratory Manual*, Vols. 1-3, Cold Spring Harbor Laboratory Press, 2 ed., 1989, or F. Ausubel et al., in Current Protocols in Molecular Biology (Green Publishing and Wiley-Interscience: New York, 1987) and periodic updates, herein incorporated by reference in their entireties. The nucleic acid (e.g., DNA) encoding the polypeptide is operably linked to an expression vector carrying one or more suitable transcriptional or translational regulatory elements derived from mammalian, viral, or insect genes. Such regulatory elements include a transcriptional promoter, an optional operator sequence to control transcription, a sequence encoding suitable mRNA ribosomal binding sites, and sequences that control the termination of transcription and translation. The expression vector can include an origin or replication that confers replication capabilities in the host cell. The expression vector can include a gene that confers selection to facilitate recognition of transgenic host cells (e.g., transformants).

The recombinant DNA can also encode any type of protein tag sequence that may be useful for purifying the protein. Examples of protein tags include but are not limited to a histidine tag, a FLAG tag, a myc tag, an HA tag, or a GST tag. Appropriate cloning and expression vectors for use with bacterial, fungal, yeast, and mammalian cellular hosts can be found in Cloning Vectors: A Laboratory Manual, (Elsevier, N.Y., 1985).

The expression vector construct can be introduced into the host cell using a method appropriate for the host cell. A variety of methods for introducing nucleic acids into host cells are known in the art, including, but not limited to, electroporation; transfection employing calcium chloride, rubidium chloride, calcium phosphate, DEAE-dextran, or other substances; viral transfection; non-viral transfection; microprojectile bombardment; lipofection; and infection (e.g., where the vector is an infectious agent). Suitable host cells include prokaryotes, yeast, mammalian cells, or bacterial cells.

Suitable bacteria include gram negative or gram positive organisms, for example, _E. coli_ or _Bacillus_ spp. Yeast, preferably from the _Saccharomyces_ species, such as _S. cerevisiae_, may also be used for production of polypeptides. Various mammalian or insect cell culture systems can also be employed to express recombinant proteins. Baculovirus systems for production of heterologous proteins in insect cells are reviewed by Luckow and Summers, (Bio/Technology, 6:47, 1988). Examples of suitable mammalian host cell lines include endothelial cells, COS-7 monkey kidney cells, CV-1, L cells, C127, 3T3, Chinese hamster ovary (CHO), human embryonic kidney cells, HeLa, 293, 293T, and BHK cell lines. Purified polypeptides are prepared by culturing suitable host/vector systems to express the recombinant proteins. For many applications, the small size of many of the polypeptides disclosed herein would make expression in _E. coli_ as the preferred method for expression. The protein is then purified from culture media or cell extracts. Any of the anti-BCMA antibodies, or antigen binding protein thereof, can be expressed by transgenic host cells.

Antibodies and antigen binding proteins disclosed herein can also be produced using cell-translation systems. For such purposes the nucleic acids encoding the polypeptide must be modified to allow in vitro transcription to produce mRNA and to allow cell-free translation of the mRNA in the particular cell-free system being utilized (eukaryotic such as a mammalian or yeast cell-free translation system or prokaryotic such as a bacterial cell-free translation system.

Nucleic acids encoding any of the various polypeptides disclosed herein may be synthesized chemically. Codon usage may be selected so as to improve expression in a cell. Such codon usage will depend on the cell type selected. Specialized codon usage patterns have been developed for _E. coli_ and other bacteria, as well as mammalian cells, plant cells, yeast cells and insect cells. See for example: Mayfield et al., Proc. Natl. Acad. Sci. USA. 2003 100(2):438-42; Sinclair et al. Protein Expr. Purif. 2002 (1):96-105; Connell N D. Curr. Opin. Biotechnol. 2001 12(5):446-9; Makrides et al. Microbiol. Rev. 1996 60(3):512-38; and Sharp et al. Yeast. 1991 7(7):657-78.

Antibodies and antigen binding proteins described herein can also be produced by chemical synthesis (e.g., by the methods described in Solid Phase Peptide Synthesis, 2nd ed., 1984, The Pierce Chemical Co., Rockford, Ill.). Modifications to the protein can also be produced by chemical synthesis.

Antibodies and antigen binding proteins described herein can be purified by isolation/purification methods for proteins generally known in the field of protein chemistry. Non-limiting examples include extraction, recrystallization, salting out (e.g., with ammonium sulfate or sodium sulfate), centrifugation, dialysis, ultrafiltration, adsorption chromatography, ion exchange chromatography, hydrophobic chromatography, normal phase chromatography, reversed-phase chromatography, gel filtration, gel permeation chromatography, affinity chromatography, electrophoresis, countercurrent distribution or any combinations of these. After purification, polypeptides may be exchanged into different buffers and/or concentrated by any of a variety of methods known to the art, including, but not limited to, filtration and dialysis.

The purified antibodies and antigen binding proteins described herein are preferably at least 65% pure, at least 75% pure, at least 85% pure, more preferably at least 95% pure, and most preferably at least 98% pure. Regardless of the exact numerical value of the purity, the polypeptide is sufficiently pure for use as a pharmaceutical product. Any of the anti-BCMA antibodies, or antigen binding protein thereof, described herein can be expressed by transgenic host cells and then purified to about 65-98% purity or high level of purity using any art-known method.

In certain embodiments, the antibodies and antigen binding proteins herein can further comprise post-translational modifications. Exemplary post-translational protein modifications include phosphorylation, acetylation, methylation, ADP-ribosylation, ubiquitination, glycosylation, carbonylation, sumoylation, biotinylation or addition of a polypeptide side chain or of a hydrophobic group. As a result, the modified polypeptides may contain non-amino acid elements, such as lipids, poly- or mono-saccharide, and phosphates. A preferred form of glycosylation is sialylation, which conjugates one or more sialic acid moieties to the polypeptide. Sialic acid moieties improve solubility and serum half-life while also reducing the possible immunogenicity of the protein. See Raju et al. Biochemistry. 2001 31; 40(30):8868-76.

In one embodiment, the antibodies and antigen binding proteins described herein can be modified to become soluble polypeptides which comprises linking the Antibodies and antigen binding proteins to non-proteinaceous polymers. In one embodiment, the non-proteinaceous polymer comprises polyethylene glycol ("PEG"), polypropylene glycol, or polyoxyalkylenes, in the manner as set forth in U.S. Pat. Nos. 4,640,835; 4,496,689; 4,301,144; 4,670,417; 4,791,192 or 4,179,337.

PEG is a water soluble polymer that is commercially available or can be prepared by ring-opening polymerization of ethylene glycol according to methods well known in the art (Sandler and Karo, Polymer Synthesis, Academic Press, New York, Vol. 3, pages 138-161). The term "PEG" is used broadly to encompass any polyethylene glycol molecule, without regard to size or to modification at an end of the PEG, and can be represented by the formula: $X-O(CH_2CH_2O)_n-CH_2CH_2OH$ (1), where n is 20 to 2300 and X is H or a terminal modification, e.g., a $C_{1-4}$ alkyl. In one embodiment, the PEG terminates on one end with hydroxy or methoxy, i.e., X is H or $CH_3$ ("methoxy PEG"). A PEG can contain further chemical groups which are necessary for binding reactions; which results from the chemical synthesis of the molecule; or which is a spacer for optimal distance of parts of the molecule. In addition, such a PEG can consist of one or more PEG side-chains which are linked together. PEGs with more than one PEG chain are called multiarmed or branched PEGs. Branched PEGs can be prepared, for example, by the addition of polyethylene oxide to various polyols, including glycerol, pentaerythriol, and sorbitol. For example, a four-armed branched PEG can be prepared from pentaerythriol and ethylene oxide. Branched PEG are described in, for example, EP-A 0 473 084 and U.S. Pat. No. 5,932,462. One form of PEGs includes two PEG side-chains (PEG2) linked via the primary amino groups of a lysine (Monfardini et al., Bioconjugate Chem. 6 (1995) 62-69).

The serum clearance rate of PEG-modified polypeptide may be modulated (e.g., increased or decreased) by about 10%, 20%, 30%, 40%, 50%, 60%, 70%, 80%, or even 90%, relative to the clearance rate of the unmodified antibodies and antigen binding proteins binding polypeptides. The PEG-modified antibodies and antigen binding proteins may have a half-life (tv2) which is enhanced relative to the half-life of the unmodified polypeptide. The half-life of PEG-modified polypeptide may be enhanced by at least 10%, 20%, 30%, 40%, 50%, 60%, 70%, 80%, 90%, 100%, 125%, 150%, 175%, 200%, 250%, 300%, 400% or 500%, or even by 1000% relative to the half-life of the unmodified antibodies and antigen binding proteins. In some embodiments, the protein half-life is determined in vitro, such as in a buffered saline solution or in serum. In other embodiments, the protein half-life is an in vivo half-life, such as the half-life of the protein in the serum or other bodily fluid of an animal.

The present disclosure provides therapeutic compositions comprising any of the anti-BCMA antibodies, or antigen binding protein thereof, described herein and a pharmaceutically-acceptable excipient. An excipient encompasses carriers, stabilizers and excipients. Excipients of pharmaceutically acceptable excipients includes for example inert diluents or fillers (e.g., sucrose and sorbitol), lubricating agents, glidants, and anti-adhesives (e.g., magnesium stearate, zinc stearate, stearic acid, silicas, hydrogenated vegetable oils, or talc). Additional examples include buffering agents, stabilizing agents, preservatives, non-ionic detergents, anti-oxidants and isotonifiers.

Therapeutic compositions and methods for preparing them are well known in the art and are found, for example, in "Remington: The Science and Practice of Pharmacy" (20th ed., ed. A. R. Gennaro A R., 2000, Lippincott Williams & Wilkins, Philadelphia, Pa.). Therapeutic compositions can be formulated for parenteral administration may, and can for example, contain excipients, sterile water, saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the antibody (or antigen binding protein thereof) described herein. Nanoparticulate formulations (e.g., biodegradable nanoparticles, solid lipid nanoparticles, liposomes) may be used to control the biodistribution of the antibody (or antigen binding protein thereof). Other potentially useful parenteral delivery systems include ethylene-vinyl acetate copolymer particles, osmotic pumps, implantable infusion systems, and liposomes. The concentration of the antibody (or antigen binding protein thereof) in the formulation varies depending upon a number of factors, including the dosage of the drug to be administered, and the route of administration.

Any of the anti-BCMA antibodies (or antigen binding portions thereof) may be optionally administered as a pharmaceutically acceptable salt, such as non-toxic acid addition salts or metal complexes that are commonly used in the pharmaceutical industry. Examples of acid addition salts include organic acids such as acetic, lactic, pamoic, maleic, citric, malic, ascorbic, succinic, benzoic, palmitic, suberic, salicylic, tartaric, methanesulfonic, toluenesulfonic, or trifluoroacetic acids or the like; polymeric acids such as tannic acid, carboxymethyl cellulose, or the like; and inorganic acid such as hydrochloric acid, hydrobromic acid, sulfuric acid phosphoric acid, or the like. Metal complexes include zinc, iron, and the like. In one example, the antibody (or antigen binding portions thereof) is formulated in the presence of sodium acetate to increase thermal stability.

Any of the anti-BCMA antibodies (or antigen binding portions thereof) may be formulated for oral use include tablets containing the active ingredient(s) in a mixture with non-toxic pharmaceutically acceptable excipients. Formulations for oral use may also be provided as chewable tablets, or as hard gelatin capsules wherein the active ingredient is mixed with an inert solid diluent, or as soft gelatin capsules wherein the active ingredient is mixed with water or an oil medium.

The term "subject" as used herein refers to human and non-human animals, including vertebrates, mammals and non-mammals. In one embodiment, the subject can be human, non-human primates, simian, ape, murine (e.g., mice and rats), bovine, porcine, equine, canine, feline, caprine, lupine, ranine or piscine.

The term "administering", "administered" and grammatical variants refers to the physical introduction of an agent to a subject, using any of the various methods and delivery systems known to those skilled in the art. Exemplary routes of administration for the formulations disclosed herein include intravenous, intramuscular, subcutaneous, intraperitoneal, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intralymphatic, intralesional, intracapsular, intraorbital, intracardiac, intradermal, intraperitoneal, transtracheal, subcuticular, intraarticular, subcapsular, subarachnoid, intraspinal, epidural and intrasternal injection and infusion, as well as in vivo electroporation. In some embodiments, the formulation is administered via a non-parenteral route, e.g., orally. Other non-parenteral routes include a topical, epidermal or mucosal route of administration, for example, intranasally, vaginally, rectally, sublingually or topically. Administering can also be performed, for example, once, a plurality of times, and/or over one or more extended periods. Any of the anti-BCMA antibodies described herein (or antigen binding protein thereof) can be administered to a subject using art-known methods and delivery routes.

The terms "effective amount", "therapeutically effective amount" or "effective dose" or related terms may be used interchangeably and refer to an amount of antibody or an antigen binding protein (e.g., any of the anti-BCMA antibodies described herein or antigen binding protein thereof) that when administered to a subject, is sufficient to effect a measurable improvement or prevention of a disease or disorder associated with tumor or cancer antigen expression. Therapeutically effective amounts of antibodies provided herein, when used alone or in combination, will vary depending upon the relative activity of the antibodies and combinations (e.g., in inhibiting cell growth) and depending upon the subject and disease condition being treated, the weight and age and sex of the subject, the severity of the disease condition in the subject, the manner of administration and the like, which can readily be determined by one of ordinary skill in the art.

In one embodiment, a therapeutically effective amount will depend on certain aspects of the subject to be treated and the disorder to be treated and may be ascertained by one skilled in the art using known techniques. In general, the polypeptide is administered at about 0.01 g/kg to about 50 mg/kg per day, preferably 0.01 mg/kg to about 30 mg/kg per day, most preferably 0.1 mg/kg to about 20 mg/kg per day. The polypeptide may be administered daily (e.g., once, twice, three times, or four times daily) or preferably less frequently (e.g., weekly, every two weeks, every three weeks, monthly, or quarterly). In addition, as is known in the art, adjustments for age as well as the body weight, general health, sex, diet, time of administration, drug interaction, and the severity of the disease may be necessary.

The present disclosure provides methods for treating a subject having a disease associated with expression of BCMA. The disease comprises cancer or tumor cells expressing the tumor-associated antigens. In one embodiment, the cancer or tumor includes cancer of the prostate, breast, ovary, head and neck, bladder, skin, colorectal, anus, rectum, pancreas, lung (including non-small cell lung and small cell lung cancers), leiomyoma, brain, glioma, glioblastoma, esophagus, liver, kidney, stomach, colon, cervix, uterus, endometrium, vulva, larynx, vagina, bone, nasal cavity, paranasal sinus, nasopharynx, oral cavity, oropharynx, larynx, hypolarynx, salivary glands, ureter, urethra, penis and testis.

In one embodiment, the cancer comprises hematological cancers, including leukemias, lymphomas, myelomas and B cell lymphomas. Hematologic cancers include multiple myeloma (MM), non-Hodgkin's lymphoma (NHL) including Burkitt's lymphoma (BL), B chronic lymphocytic leukemia (B-CLL), systemic lupus erythematosus (SLE), B and T acute lymphocytic leukemia (ALL), acute myeloid leukemia (AML), chronic lymphocytic leukemia (CLL), diffuse large B cell lymphoma, chronic myelogenous leukemia (CML), hairy cell leukemia (HCL), follicular lymphoma, Waldenstrom's Macroglobulinemia, mantle cell lymphoma, Hodgkin's Lymphoma (HL), plasma cell myeloma, precursor B cell lymphoblastic leukemia/lymphoma, plasmacytoma, giant cell myeloma, plasma cell myeloma, heavy-chain myeloma, light chain or Bence-Jones myeloma, lymphomatoid granulomatosis, post-transplant lymphoproliferative disorder, an immunoregulatory disorder, rheumatoid arthritis, myasthenia gravis, idiopathic thrombocytopenia purpura, anti-phospholipid syndrome, Chagas' disease, Grave's disease, Wegener's granulomatosis, poly-arteritis nodosa, Sjogren's syndrome, pemphigus vulgaris, scleroderma, multiple sclerosis, anti-phospholipid syndrome, ANCA associated vasculitis, Goodpasture's disease, Kawasaki disease, autoimmune hemolytic anemia, and rapidly progressive glomerulonephritis, heavy-chain disease, primary or immunocyte-associated amyloidosis, and monoclonal gammopathy of undetermined significance.

The present disclosure provides BCMA binding proteins, particularly anti-BCMA antibodies, or antigen-binding portions thereof, that specifically bind BCMA and uses thereof. In one embodiment, the BCMA binding proteins bind an epitope of BCMA (B Cell Maturation Antigen (BCMA). BCMA is also known as TNFRSF17 and CD269 (e.g., UniProt Q02223)). Various aspects of the anti-BCMA antibodies relate to antibody fragments, single-chain antibodies, pharmaceutical compositions, nucleic acids, recombinant expression vectors, host cells, and methods for preparing and using such anti-BCMA antibodies. Methods for using the anti-BCMA antibodies include in vitro and in vivo methods for binding BCMA, detecting BCMA and treating diseases associated with BCMA expression.

The present disclosure provides antigen binding proteins that bind specifically to a BCMA polypeptide (e.g., antigen target) or fragment of the BCMA polypeptide. In one embodiment, the BCMA target antigen comprises a naturally-occurring polypeptide (e.g., UniProt accession No. Q02223-1) having a wild-type or polymorphic or mutant amino acid sequence. The BCMA target antigen can be prepared by recombinant methods or can be chemically synthesized. The BCMA target antigen can be in soluble form or membrane-bound form (e.g., expressed by a cell or phage). In one embodiment, the BCMA target antigen is expressed by a cell, for example a cancer or non-cancer cell line that naturally expresses BCMA or is engineered to express BCMA, such as U2392, EJM, MMUR, U266, OPM2, H929, JJN-3, RPMI-8226, K562, NCIH929, ANBL-6, DP-6, KAS-6/1, KP6 or JMW. Cell lines that do not express BCMA are not expected to bind an anti-BCMA antibody, such as for example K562, A549 and TC71 cell lines. The BCMA target antigen can be a fusion protein or conjugated for example with a detectable moiety such as a fluorophore. The BCMA target antigen can bind APRIL and/or BAFF. The BCMA target antigen can be in mutated form that either increases or decreases binding to APRIL and/or BAFF. In one embodiment, human BCMA target antigen comprises the amino acid sequence of SEQ ID NO:1 (e.g., recombinant human BCMA from LifeSpan BioSciences, catalog #LS-G5771) or SEQ ID NO:2 (e.g., recombinant his-tagged human BCMA from AcroBioSystems, catalog # BCA-H522y-100ug). In one embodiment, the BCMA target antigen is a mutant polypeptide comprising the amino acid sequence of SEQ ID NO:3 or 4. In one embodiment, wild type and/or mutated human BCMA antigen can be used in an assay comparing binding capabilities of any of the anti-BCMA antibodies described herein compared to a control anti-BCMA antibody, and/or in an epitope mapping assay comparing binding capabilities of any of the anti-BCMA antibodies described herein compared to a control anti-BCMA antibody.

The present disclosure provides a fully human antibody of an IgG class that binds to a BCMA polypeptide. In one embodiment, the anti-BCMA antibody comprises a heavy chain variable region having at least 95% sequence identity, or at least 96% sequence identity, or at least 97% sequence identity, or at least 98% sequence identity, or at least 99% sequence identity to the amino acid sequence of SEQ ID NO:8, 10, 12, 14 or 22, or combinations thereof; and/or the anti-BCMA antibody comprises a light chain variable region having 95% sequence identity, or at least 96% sequence identity, or at least 97% sequence identity, or at least 98% sequence identity, or at least 99% sequence identity to the amino acid sequence of SEQ ID NO:9, 11, 13, 15, 16, 17, 18, 19, 20, 21 or 23, or combinations thereof. In one embodiment, the anti-BCMA antibody comprises an IgG1, IgG2, IgG3 or IgG4 class antibody. In one embodiment, the anti-BCMA antibody comprises an IgG1 or IgG4 class antibody.

In one embodiment, the anti-BCMA antibody, or fragment thereof, comprises an antigen binding portion that binds an epitope of a BCMA target antigen with a binding affinity ($K_D$) of $10^{-6}$ M or less, $10^{-7}$M or less, $10^{-8}$M or less, $10^{-9}$M or less, or $10^{-10}$ M or less (see FIGS. 3-10 and Tables 2 and 3). In one embodiment, the BCMA antigen comprises a cell surface BCMA antigen or a soluble BCMA antigen. In one embodiment, the BCMA antigen comprises an extracellular portion of a cell surface BCMA antigen. In one embodiment, the BCMA antigen comprises a human or non-human BCMA antigen. In one embodiment, the BCMA antigen is expressed by a human or non-human cell. In one embodiment, the anti-BCMA antibody binds a human BCMA expressed by a human B cell or expressed by a human multiple myeloma cell. In one embodiment, binding between the anti-BCMA antibody, or fragment thereof, can be detected and measured using surface plasmon resonance, flow cytometry and/or ELISA.

In one embodiment, the anti-BCMA antibody or antigen-binding fragment comprises an antigen binding portion that binds a human BCMA epitope and blocks binding (e.g, inhibits binding) of human APRIL and/or human BAFF to the human BCMA epitope. In one embodiment, APRIL refers to human A PRoliferation-Inducing Ligand (also known as TNF13, CD256) which is commercially-available from R&D Systems (catalog #5860-AP-010/CF) or from IBI Scientific (catalog #RPH-151). In one embodiment, BAFF refers to human BAFF (e.g., UniProt Accession No. Q9Y275). In one embodiment, the anti-BCMA antibody or antigen-binding fragment blocks binding of human APRIL and/or human BAFF to a human BCMA epitope by reducing the level of binding by about 5-25%, or by about 25-45%, or by about 45-65%, or by about 65-85%, or by about 85-95% or higher levels of reduced binding.

In one embodiment, the anti-BCMA antibody reduces APRIL-dependent or BAFF-dependent NF-κB activation by about 1-5% (or less than about 1%), by about 5-25%, or by about 25-45%, or by about 45-65%, or by about 65-85%, or by about 85-95% or higher levels of reduced binding.

The present disclosure provides an anti-BCMA antibody or antigen-binding fragment which binds an epitope of BCMA from a human, or can bind (e.g., cross-reactivity) with an epitope of BCMA (e.g., homologous antigen) from any one or any combination of non-human animals such as mouse, rat, goat, rabbit, hamster and/or monkey (e.g., cyno-molgus). In one embodiment, the anti-BCMA antibody or antigen-binding fragment binds mouse BCMA with a binding affinity $K_D$ of $10^{-5}$M or less, or $10^{-6}$ M or less, or $10^{-7}$M or less, or $10^{-8}$M or less, or $10^{-9}$ M or less, or $10^{-10}$ M or less. In one embodiment, the anti-BCMA antibody or antigen-binding fragment binds cynomolgus BCAM with a binding affinity $K_D$ of $10^{-5}$M or less, or $10^{-6}$M or less, or $10^{-7}$M or less, or $10^{-8}$M or less, or $10^{-9}$M or less, or $10^{-10}$ M or less. In one embodiment, cyno BCMA is commercially-available from ACROBiosystems (catalog # BCA-052H7). In one embodiment, mouse BCMA is commercially-available from ACROBiosystems (catalog # BCA-M52H3).

The present disclosure provides an anti-BCMA antibody or antigen-binding fragment which binds an epitope of APRIL and/or BAFF from a human, or can bind (e.g., cross-react) with an epitope of APRIL and/or BAFF (e.g., homologous antigen) from any one or any combination of non-human animals such as mouse, rat, goat, rabbit, hamster and/or monkey (e.g., cynomolgus). In one embodiment, human APRIL protein is commercially-available from R&D Systems (catalog #5860-AP-010/CF) or from IBI Scientific (catalog #RPH-151).

The present disclosure provides a fully human antibody comprising both heavy and light chains, wherein the heavy/light chain variable region amino acid sequences have at least 95% sequence identity, or at least 96% sequence identity, or at least 97% sequence identity, or at least 98% sequence identity, or at least 99% sequence identity to any of the following amino acid sequence sets: SEQ ID NOS:8 and 9 (herein called BCA7), SEQ ID NOS:10 and 11 (herein called BC4C9), SEQ ID NOS:12 and 13 (herein called CD5C4), SEQ ID NOS:14 and 15 (herein called BC6G8), SEQ ID NOS:8 and 16 (herein called BCA7-2C5), SEQ ID NOS:8 and 17 (herein called BCA7-2E1), SEQ ID NOS:8 and 18 (herein called BCA7-2D11), SEQ ID NOS:8 and 19 (herein called BCA7-2G2), SEQ ID NOS:8 and 20 (herein called BCA7-2D8), SEQ ID NOS:8 and 21 (herein called BCA7-2E8), or SEQ ID NOS:22 and 23 (herein called BCA7-2C5 full length).

The present disclosure provides a Fab fully human antibody fragment, comprising a heavy variable region from a heavy chain and a variable region from a light chain, wherein the sequence of the variable region from the heavy chain is at least 95% identical, or at least 96% identical, or at least 97% identical, or at least 98% identical, or at least 99% identical to the amino acid sequence of SEQ ID NO:8, 10, 12, 14 or 22, or combinations thereof. The sequence of the variable region from the light chain is at least 95% identical, or at least 96% identical, or at least 97% identical, or at least 98% identical, or at least 99% identical to the amino acid sequence of SEQ ID NO:9, 11, 13, 15, 16, 17, 18, 19, 20, 21 or 23, or combinations thereof.

The present disclosure provides a Fab fully human antibody fragment, comprising a heavy chain variable region and a light chain variable region, wherein the heavy/light chain variable region amino acid sequences are at least 95% identical, or at least 96% identical, or at least 97% identical, or at least 98% identical, or at least 99% identical to any of the following amino acid sequence sets: SEQ ID NOS:8 and 9 (herein called BCA7), SEQ ID NOS:10 and 11 (herein called BC4C9), SEQ ID NOS:12 and 13 (herein called CD5C4), SEQ ID NOS:14 and 15 (herein called BC6G8), SEQ ID NOS:8 and 16 (herein called BCA7-2C5), SEQ ID NOS:8 and 17 (herein called BCA7-2E1), SEQ ID NOS:8 and 18 (herein called BCA7-2D11), SEQ ID NOS:8 and 19 (herein called BCA7-2G2), SEQ ID NOS:8 and 20 (herein called BCA7-2D8), SEQ ID NOS:8 and 21 (herein called BCA7-2E8), or SEQ ID NOS:22 and 23 (herein called BCA7-2C5 full length).

The present disclosure provides a single chain fully human antibody comprising a polypeptide chain having a variable region from a fully human heavy chain and a variable region from a fully human light chain, and optionally a linker joining the variable heavy and variable light chain regions, wherein the variable heavy region comprises at least 95% sequence identity, or at least 96% sequence identity, or at least 97% sequence identity, or at least 98% sequence identity, or at least 99% sequence identity to the amino acid sequence of SEQ ID NO: 8, 10, 12, 14 or 22, or combinations thereof. The variable light region comprises at least 95% sequence identity, or at least 96% sequence identity, or at least 97% sequence identity, or at least 98% sequence identity, or at least 99% sequence identity to the amino acid sequence of SEQ ID NO: 9, 11, 13, 15, 16, 17, 18, 19, 20, 21 or 23, or combinations thereof.

The present disclosure provides a single chain fully human antibody comprising a polypeptide chain having heavy chain variable region and a light chain variable region, wherein the heavy/light chain variable region amino acid sequence sets are at least 95% identical, or at least 96% identical, or at least 97% identical, or at least 98% identical, or at least 99% identical to any of the following amino acid sequence sets: SEQ ID NOS:8 and 9 (herein called BCA7), SEQ ID NOS:10 and 11 (herein called BC4C9), SEQ ID NOS:12 and 13 (herein called CD5C4), SEQ ID NOS:14 and 15 (herein called BC6G8), SEQ ID NOS:8 and 16 (herein called BCA7-2C5), SEQ ID NOS:8 and 17 (herein called BCA7-2E1), SEQ ID NOS:8 and 18 (herein called BCA7-2D11), SEQ ID NOS:8 and 19 (herein called BCA7-2G2), SEQ ID NOS:8 and 20 (herein called BCA7-2D8), SEQ ID NOS:8 and 21 (herein called BCA7-2E8), or SEQ ID NOS:22 and 23 (herein called BCA7-2C5 full length).

The present disclosure provides pharmaceutical compositions comprising any of the anti-BCMA antibodies or antigen-binding fragments described herein and a pharmaceutically-acceptable excipient. An excipient encompasses carriers and stabilizers. In one embodiment, the pharmaceutical compositions comprise an anti-BCMA antibody, or antigen binding fragment thereof, comprising a heavy chain variable region and a light chain variable region, wherein the heavy/light chain variable region amino acid sequences are at least 95% identical, or at least 96% identical, or at least 97% identical, or at least 98% identical, or at least 99% identical to any of the following amino acid sequence sets: SEQ ID NOS:8 and 9 (herein called BCA7), SEQ ID NOS:10 and 11 (herein called BC4C9), SEQ ID NOS:12 and 13 (herein called CD5C4), SEQ ID NOS:14 and 15 (herein called BC6G8), SEQ ID NOS:8 and 16 (herein called BCA7-2C5), SEQ ID NOS:8 and 17 (herein called BCA7-2E1), SEQ ID NOS:8 and 18 (herein called BCA7-2D11), SEQ ID NOS:8 and 19 (herein called BCA7-2G2), SEQ ID NOS:8 and 20 (herein called BCA7-2D8), SEQ ID NOS:8 and 21 (herein called BCA7-2E8), or SEQ ID NOS:22 and 23 (herein called BCA7-2C5 full length).

The present disclosure provides a kit comprising any one or any combination of two or more of the anti-BCMA antibodies, or antigen binding fragments thereof, described herein. In one embodiment, the kit comprises any one or any combination of two or more anti-BCMA antibodies, or antigen binding fragments thereof, comprising a heavy chain variable region and a light chain variable region, wherein the heavy/light chain variable region amino acid sequences are at least 95% identical, or at least 96% identical, or at least 97% identical, or at least 98% identical, or at least 99% identical to any of the following amino acid sequence sets: of SEQ ID NOS:8 and 9 (herein called BCA7), SEQ ID NOS:10 and 11 (herein called BC4C9), SEQ ID NOS:12 and 13 (herein called CD5C4), SEQ ID NOS:14 and 15 (herein called BC6G8), SEQ ID NOS:8 and 16 (herein called BCA7-2C5), SEQ ID NOS:8 and 17 (herein called BCA7-2E1), SEQ ID NOS:8 and 18 (herein called BCA7-2D11), SEQ ID NOS:8 and 19 (herein called BCA7-2G2), SEQ ID NOS:8 and 20 (herein called BCA7-2D8), SEQ ID NOS:8 and 21 (herein called BCA7-2E8), or SEQ ID NOS:22 and 23 (herein called BCA7-2C5 full length). The kit can be used to detect the presence or absence of a BCMA antigen for example in a biological sample. The kit can be used for conducting an in vitro reaction such as antigen binding assays in the form of ELIZA, flow cytometry or plasmon surface resonance; in vitro cell activation assays including NF-κB activation assays; luciferase-reporter assays; Western blotting and detection; and other such in vitro assays. The kit can be used for treating a subject having a BCMA-associated disease or condition, such as multiple myeloma.

The present disclosure provides methods for inhibiting growth or proliferation of target cells, or methods for killing target cells, the method comprising: contacting a population of effector cells with a population of target cells (e.g., target cells expressing BCMA) in the presence of an anti-BCMA antibody (or antibody fragment thereof) described herein, under conditions that are suitable for killing the target cells. In one embodiment, the population of effector cells comprises peripheral blood mononuclear cells (PBMCs) or natural killer (NK) cells. The PBMCs can include lymphocytes, including T cells, B cells and/or NK cells. In one embodiment, the population of target cells comprise cells that naturally express BCMA, including B cells, multiple myeloma (MM) cells, or any type of B cells from a subject having a disease associated with BCMA-expression. In one embodiment, the population of target cells are any type of transgenic cells that are engineered to express BCMA. In one embodiment, the ratio of effector to target cells can be about 1:1, or about 2:1, or about 3:1, or about 4:1, or about 5:1, or about 5-10:1, or about 10-20:1, or about 20-30:1.

791 The present disclosure provides methods for treating a subject having a disease associated with BCMA over-expression or a BCMA-positive cancer, the method comprising: administering to the subject an effective amount of a therapeutic composition comprising an anti-BCMA antibody described herein or antigen binding fragment thereof, e.g., which is selected from a group consisting of any of the fully human anti-BCMA antibodies described herein, any of the Fab fully human anti-BCMA antibodies described herein, and any of the single chain human anti-BCMA antibodies described herein. In one embodiment, the BCMA-positive cancer comprises: a B-cell leukemia, B-cell lymphoma or B-cell myeloma. Also provided are methods for treating a subject having a disease associated with BCMA expression, wherein the disease associated with BCMA expression is selected from a group consisting of multiple myeloma (MM), non-Hodgkin's lymphoma (NHL) including Burkitt's lymphoma (BL), B chronic lymphocytic leukemia (B-CLL), systemic lupus erythematosus (SLE), B and T acute lymphocytic leukemia (ALL), acute myeloid leukemia (AML), chronic lymphocytic leukemia (CLL), diffuse large B cell lymphoma, chronic myelogenous leukemia (CML), hairy cell leukemia (HCL), follicular lymphoma, Waldenstrom's Macroglobulinemia, mantle cell lymphoma, Hodgkin's Lymphoma (HL), plasma cell myeloma, precursor B cell lymphoblastic leukemia/lymphoma, plasmacytoma, giant cell myeloma, plasma cell myeloma, heavy-chain myeloma, light chain or Bence-Jones myeloma, lymphomatoid granulomatosis, post-transplant lymphoproliferative disorder, an immunoregulatory disorder, rheumatoid arthritis, myasthenia gravis, idiopathic thrombocytopenia purpura, anti-phospholipid syndrome. Chagas' disease, Grave's disease, Wegener's granulomatosis, poly-arteritis nodosa, Sjogren's syndrome, pemphigus vulgaris, scleroderma, multiple sclerosis, anti-phospholipid syndrome, ANCA associated vasculitis, Goodpasture's disease, Kawasaki disease, autoimmune hemolytic anemia, and rapidly progressive glomerulonephritis, heavy-chain disease, primary or immunocyte-associated amyloidosis, and monoclonal gammopathy of undetermined significance, the method comprising: administering to the subject an effective amount of a therapeutic composition comprising an antibody described herein or an antigen-binding fragment thereof.

---

LIST OF SEQUENCES:

Wild type Human BCMA protein (5-54) SEQ ID NO: 1:
AGQCSQNEYFDSLLHACIPCQLRCSSNTPPLTCQRYCNASVTNSVKGTNA.

Wild type Human BCMA protein (1-54) SEQ ID NO: 2:
MLQMAGQCSQNEYFDSLLHACIPCQLRCSSNTPPLTCQRYCNASVTNSVKGTNA.

-continued

---

LIST OF SEQUENCES:

---

Wild type Human BCMA protein (UniProt Q02223-1) SEQ ID NO: 92
MLQMAGQCSQNEYFDSLLHACIPCQLRCSSNTPPLTCQRYCNASVTNSVK
GTNAILWTCLGLSLIISLAVFVLMFLLRKINSEPLKDEFKNTGSGLLGMANI
DLEKSRTGDEIILPRGLEYTVEECTCEDCIKSKPKVDSDHCFPLPAMEEGAT
ILVTTKTNDYCKSLPAALSATEIEKSISAR.

Mutant-1 human BCMA protein SEQ ID NO: 3
MLQMAGQCSQNEYFDSGGHACIPCQLRCSSNTPPLTCQRYCNASVTNSVKGTNA.

Mutant-2 human BCMA protein SEQ ID NO: 4:
MLQMAGQCSQNEYFDSLLHACIPCQLRCSSNPPGTCQRYCNASVTNSVKGTNA.

Wild type human BCMA protein-mouse Fc SEQ ID NO: 5:
MLQMAGQCSQNEYFDSLLHACIPCQLRCSSNTPPLTCQRYCNASVTNSVKGTNA
GLGGLVDYKDDDDKTHTCPPCKCPAPNLLGGPSVFIFPPPKIKDVLMISLSPIVTC
VVVDVSEDDPDVQISWFVNNVEVHTAQTQTHREDYNSTLRVVSALPIQHQDWMSG
KEFKCKVNNKDLPAPIERTISKPKGSVRAPQVYVLPPPEEEMTKKQVTLTCMVTD
FMPEDIYVEWTNNGKTELNYKNTEPVLDSDGSYFMYSKLRVEKKNWVERNSYSCS
VVHEGLHNHHTTKSFSRTPGK.

Mutant-1 human BCMA protein-mouse Fc SEQ ID NO: 6:
MLQMAGQCSQNEYFDSGGHACIPCQLRCSSNTPPLTCQRYCNASVTNSVKGTNA
GLGGLVDYKDDDDKTHTCPPCKCPAPNLLGGPSVFIFPPPKIKDVLMISLSPIVTC
VVVDVSEDDPDVQISWFVNNVEVHTAQTQTHREDYNSTLRVVSALPIQHQDWMSG
KEFKCKVNNKDLPAPIERTISKPKGSVRAPQVYVLPPPEEEMTKKQVTLTCMVTD
FMPEDIYVEWTNNGKTELNYKNTEPVLDSDGSYFMYSKLRVEKKNWVERNSYSCS
VVHEGLHNHHTTKSFSRTPGK.

Mutant-2 human BCMA protein-mouse Fc SEQ ID NO: 7:
MLQMAGQCSQNEYFDSLLHACIPCQLRCSSNPPGTCQRYCNASVTNSVKGTNA
GLGGLVDYKDDDDKTHTCPPCKCPAPNLLGGPSVFIFPPPKIKDVLMISLSPIVTC
VVVDVSEDDPDVQISWFVNNVEVHTAQTQTHREDYNSTLRVVSALPIQHQDWMSG
KEFKCKVNNKDLPAPIERTISKPKGSVRAPQVYVLPPPEEEMTKKQVTLTCMVTD
FMPEDIYVEWTNNGKTELNYKNTEPVLDSDGSYFMYSKLRVEKKNWVERNSYSCS
VVHEGLHNHHTTKSFSRTPGK.

---

TABLE 1

| Heavy chain variable: | Light chain variable: |
|---|---|
| BCA7 SEQ ID NO: 8<br>EVQLVESGGGLVKPGGSLRLSCAASGFTSS<br>TAWMSWVRQAPGKGLEWVGRIKSKSDGGTT<br>DYAAPVKGRFTISRDDSKNTLFLQMNSLKT<br>EDTAVYYCAKGGGTYGYWGQGTTVTVSS | BCA7 SEQ ID NO: 9<br>SYVLTQPASVSGSPGQSVTISCTGTSSDVG<br>GYNYVSWYQQHPGKAPKLMIYDVSNRPSGV<br>SNRFSGSKSGNTASLTISGLQAEDEADYYC<br>GSYTSSGSYVFGTGTKLTVL |
| BC4C9 SEQ ID NO: 10<br>EVQLVQSGAEVKKPGASVKVSCKAFGYTFT<br>SYDINWVRQATGQGLEWMGWMNPNSGNTGY<br>AQKFQGRVTMTRNTSISTAYMELSSLRSED<br>TAVYYCASGLGEWGQGTLVTVSS | BC4C9 SEQ ID NO: 11<br>QSVLTQPASVSGSPGQSVTISCTGTSSDVG<br>GYNYVSWYQQHPGKAPKLMIYDVSKRPSGV<br>SNRFSGSKSGNTASLTISGLQAEDEADYYC<br>ISYSSSSTFYVFGTGTKVTVL |
| BC5C4 SEQ ID NO: 12<br>EVQLVESGGGLVQPGRSLRLSCAASGFTFD<br>DYAMHWVRQAPGKGLEWVSGISWNSGSIGY<br>ADSVKGRFTISRDNAKNSLYLQMNSLRAED<br>TAVYYCATIDNVAFHSWGQGTLVTVSS | BC5C4 SEQ ID NO: 13<br>QSVLTQPPSASGSPGQSVTISCTGTSSDIG<br>GYNYVSWYQQHPGKAPKLIIYEVSNRPSGV<br>SDRFSGSKSGNTASLTISGLQAEDEADYYC<br>SSYTDNGALVVFGGGTKLTVL |
| BC6G8 SEQ ID NO: 14<br>QVQLQQSGPGLVKPSQTLSLTCAISGDSVS<br>SNSVGWHWIRQSPSRGLEWLGRTYYRSNFA<br>TDYAASVRGRMTINADTSTNQISLHLNSLT<br>PEDTAVYYCTRDWYGVYDFWGQGTLVTVSS | BC6G8 SEQ ID NO: 15<br>SYELMQPPSVSVAPGKTARITCGGNNIGSK<br>SVHWYQQKPGQAPVLVIYYDSDRPSGIPER<br>FSGSNSGNTATLTISRVEAGDEADYYCQVW<br>DSSSDHLVVFGGGTKLTVL |
| BCA7-2C5 SEQ ID NO: 8<br>EVQLVESGGGLVKPGGSLRLSCAASGFTSS<br>TAWMSWVRQAPGKGLEWVGRIKSKSDGGTT<br>DYAAPVKGRFTISRDDSKNTLFLQMNSLKT<br>EDTAVYYCAKGGGTYGYWGQGTTVTVSS | BCA7-2C5 SEQ ID NO: 16<br>QSALTQPASVSGSPGQSVTISCTGTSSAHG<br>GHYYVSWYQQHPGKAPKLMIYDVSNRPSGV<br>SNRFSGSKSGNTASLTISGLQAEDEADYYC<br>GSYTSSGSYVFGTGTKLTVL |

TABLE 1 -continued

| Heavy chain variable: | Light chain variable: |
|---|---|
| BCA7-2E1 SEQ ID NO: 8<br>EVQLVESGGGLVKPGGSLRLSCAASGFTSS<br>TAWMSWVRQAPGKGLEWVGRIKSKSDGGTT<br>DYAAPVKGRFTISRDDSKNTLFLQMNSLKT<br>EDTAVYYCAKGGGTYGYWGQGTTVTVSS | BCA7-2E1 SEQ ID NO: 17<br>QSALTQPASVSGSPGQSVTISCTGTSSDGG<br>GHTYVSWYQQHPGKAPKLMIYDVSNRPSWV<br>SNRFSGSKSGNTASLTISGLQAEDEADYYC<br>GSYTSSGSYVFGTGTKLTVL |
| BCA7-2D11 SEQ ID NO: 8<br>EVQLVESGGGLVKPGGSLRLSCAASGFTSS<br>TAWMSWVRQAPGKGLEWVGRIKSKSDGGTT<br>DYAAPVKGRFTISRDDSKNTLFLQMNSLKT<br>EDTAVYYCAKGGGTYGYWGQGTTVTVSS | BCA7-2D11 SEQ ID NO: 18<br>SYELTQPASVSGSPGQSVTISCTGTSSVVG<br>GHDYVSWYQQHPGKAPKLMIYDVSNRPSGV<br>SNRFSGSKSGNTASLTISGLQAEDEADYYC<br>GSYTSSGSYVFGTGTKVTVL |
| BCA7-2G2 SEQ ID NO: 8<br>EVQLVESGGGLVKPGGSLRLSCAASGFTSS<br>TAWMSWVRQAPGKGLEWVGRIKSKSDGGTT<br>DYAAPVKGRFTISRDDSKNTLFLQMNSLKT<br>EDTAVYYCAKGGGTYGYWGQGTTVTVSS | BCA7-2G2 SEQ ID NO: 19<br>QSVLTQPASVSGSPGQSVTISCTGTSSSVG<br>GRQYVSWYQQHPGKAPKLMIYDVSNRPSGV<br>SNRFSGSKSGNTASLTISGLQAEDEADYYC<br>GSYTSSGSYVFGTGTKLTVL |
| BCA7-2D8 SEQ ID NO: 8<br>EVQLVESGGGLVKPGGSLRLSCAASGFTSS<br>TAWMSWVRQAPGKGLEWVGRIKSKSDGGTT<br>DYAAPVKGRFTISRDDSKNTLFLQMNSLKT<br>EDTAVYYCAKGGGTYGYWGQGTTVTVSS | BCA7-2D8 SEQ ID NO: 20<br>QSVLTQPASVSGSPGQSVTISCTGTSSSIG<br>DSYYVSWYQQHPGKAPKLMIYDVSNRPSGV<br>SNRFSGSKSGNTASLTISGLQAEDEADYYC<br>GSYTSSGSYVFGTGTTLTVL |
| BCA7-2E8 SEQ ID NO: 8<br>EVQLVESGGGLVKPGGSLRLSCAASGFTSS<br>TAWMSWVRQAPGKGLEWVGRIKSKSDGGTT<br>DYAAPVKGRFTISRDDSKNTLFLQMNSLKT<br>EDTAVYYCAKGGGTYGYWGQGTTVTVSS | BCA7-2E8 SEQ ID NO: 21<br>QSVLTQPASVSGSPGQSVTISCTGTSSDVG<br>GYNYVSWYQQHPGKAPKLMIYDVSNRPSGV<br>SNRFSGSKSGNTASLTISGLQAEDEADYYC<br>GSLRSNGDYVFGTGTTLTVL |
| BCA7-2C5 (IgG1 SPPC) SEQ ID NO: 22<br>EVQLVESGGGLVKPGGSLRLSCAASGFTSS<br>TAWMSWVRQAPGKGLEWVGRIKSKSDGGTT<br>DYAAPVKGRFTISRDDSKNTLFLQMNSLKT<br>EDTAVYYCAKGGGTYGYWGQGTTVTVSSAS<br>TKGPSVFPLAPSSKSTSGGTAALGCLVKDY<br>FPEPVTVSWNSGALTSGVHTFPAVLQSSGL<br>YSLSSVVTVPSSSLGTQTYICNVNHKPSNT<br>KVDKRVEPKSCDKTHTSPPCPAPELLGGPS<br>VFLFPPKPKDTLMISRTPEVTCVVVDVSHE<br>DPEVKFNWYVDGVEVHNAKTKPREEQYNST<br>YRVVSVLTVLHQDWLNGKEYKCKVSNKALP<br>APIEKTISKAKGQPREPQVYTLPPSREEMT<br>KNQVSLTCLVKGFYPSDIAVEWESNGQPEN<br>NYKTTPPVLDSDGSFFLYSKLTVDKSRWQQ<br>GNVFSCSVMHEALHNHYTQKSLSLSPGK | BCA7-2C5 (lambda) SEQ ID NO: 23<br>QSVLTQPASVSGSPGQSVTISCTGTSSAHG<br>GHYYVSWYQQHPGKAPKLMIYDVSNRPSGV<br>SNRFSGSKSGNTASLTISGLQAEDEADYYC<br>GSYTSSGSYVFGTGTKLTVLGQPKAAPSVT<br>LFPPSSEELQANKATLVCLISDFYPGAVTV<br>AWKADSSPVKAGVETTTPSKQSNNKYAASS<br>YLSLTPEQWKSHRSYSCQVTHEGSTVEKTV<br>APTECS |
| J6M0<br>GSK anti-BCMA Ab SEQ ID NO: 24<br>QVQLVQSGAEVKKPGSSVKVSCKASGGTFS<br>NYWMHWVRQAPGQGLEWMGATYRGHSDTYY<br>NQKFKGRVTITADKSTSTAYMELSSLRSED<br>TAVYYCARGAIYDGYDVLDNWGQGTLVTVSS | J6M0<br>GSK anti-BCMA Ab SEQ ID NO: 25<br>DIQMTQSPSSLSASVGDRVTITCSASQDIS<br>NYLNWYQQKPGKAPKLLIYYTSNLHSGVPS<br>RFSGSGSGTDFTLTISSLQPEDFATYYCQQ<br>YRKLPWTFGQGTKLEIK |
| C11D5<br>BB anti-BCMA Ab SEQ ID NO: 26<br>QIQLVQSGPELKKPGETVKISCKASGYTFT<br>DYSINWVKRAPGKGLKWMGWINTETREPAY<br>AYDFRGRFAFSLETSASTAYLQINNLKYED<br>TATYFCALDYSYAMDYWGQGTTLTVSS | C11D5<br>BB anti-BCMA Ab SEQ ID NO: 27<br>DIVLTQSPASLAMSLGKRATISCRASESVS<br>VIGAHLIHWYQQKPGQPPKLLIYLASNLET<br>GVPARFSGSGSGTDFTLTIDPVEEDDVAIY<br>SCLQSRIFPRTFGGGTKLEIK |

TABLE 2

| CDRs 1, 2 and 3: |
|---|
| BCA7<br>BCA7 (VH-CDR1) SEQ ID NO: 29 TAWNS<br>BCA7 (VH-CDR2) SEQ ID NO: 30 RIKSKSDGGTTDYAAPVKG<br>BCA7 (VH-CDR3) SEQ ID NO: 31 GGGTYGY<br>BCA7 (VL-CDR1) SEQ ID NO: 32 TGTSSDVGGYNYVS<br>BCA7 (VL-CDR2) SEQ ID NO: 33 DVSNRPS<br>BCA7 (VL-CDR3) SEQ ID NO: 34 GSYTSSGSYV |

TABLE 2 -continued

CDRs 1, 2 and 3:

```
BC4C9
BC4C9 (VH-CDR1) SEQ ID NO: 35 SYDIN
BC4C9 (VH-CDR2) SEQ ID NO: 36 WMNPNSGNTGYAQKFQG
BC4C9 (VH-CDR3) SEQ ID NO: 37 GLGE
BC4C9 (VL-CDR1) SEQ ID NO: 38 TGTSSDVGGYNYVS
BC4C9 (VL-CDR2) SEQ ID NO: 39 DVSKRPS
BC4C9 (VL-CDR3) SEQ ID NO: 40 ISYSSSSTFYV

BC5C4
BC5C4 (VH-CDR1) SEQ ID NO: 41 DYAMH
BC5C4 (VH-CDR2) SEQ ID NO: 42 GISWNSGSIGYADSVKG
BC5C4 (VH-CDR3) SEQ ID NO: 43 IDNVAFHS
BC5C4 (VL-CDR1) SEQ ID NO: 44 TGTSSDIGGYNYVS
BC5C4 (VL-CDR2) SEQ ID NO: 45 EVSNRPS
BC5C4 (VL-CDR3) SEQ ID NO: 46 EVSNRPS

BC6G8
BC6G8 (VH-CDR1) SEQ ID NO: 47 SNSVGWH
BC6G8 (VH-CDR2) SEQ ID NO: 48 RTYYRSNFATDYAASVRG
BC6G8 (VH-CDR3) SEQ ID NO: 49 DWYGVYDF
BC6G8 (VL-CDR1) SEQ ID NO: 50 GGNNIGSKSVH
BC6G8 (VL-CDR2) SEQ ID NO: 51 YDSDRPS
BC6G8 (VL-CDR3) SEQ ID NO: 52 QVWDSSSDHLVV

BCA7-2C5
BCA7-2C5 (VH-CDR1) SEQ ID NO: 53 TAWMS
BCA7-2C5 (VH-CDR2) SEQ ID NO: 54 RTKYYRSNFATDYAASVRG
BCA7-2C5 (VH-CDR3) SEQ ID NO: 55 GGGTYGY
BCA7-2C5 (VL-CDR1) SEQ ID NO: 56 TGTSSAHGGHYYVS
BCA7-2C5 (VL-CDR2) SEQ ID NO: 57 DVSNRPS
BCA7-2C5 (VL-CDR3) SEQ ID NO: 58 GSYTSSGSYV

BCA7-2E1
BCA7-2E1 (VH-CDR1) SEQ ID NO: 59 TAWMS
BCA7-2E1 (VH-CDR2) SEQ ID NO: 60 RIKSKSDGGTTDYAAPVKG
BCA7-2E1 (VH-CDR3) SEQ ID NO: 61 GGGTYGY
BCA7-2E1 (VL-CDR1) SEQ ID NO: 62 TGTSSDGGGHTYVS
BCA7-2E1 (VL-CDR2) SEQ ID NO: 63 DVSNRPS
BCA7-2E1 (VL-CDR3) SEQ ID NO: 64 GSYTSSGSYV

BCA7-2D11
BCA7-2D11 (VH-CDR1) SEQ ID NO: 65 TAWMS
BCA7-2D11 (VH-CDR2) SEQ ID NO: 66 RIKSKSDGGTTDYAAPVKG
BCA7-2D11 (VH-CDR3) SEQ ID NO: 67 GGGTYGY
BCA7-2D11 (VL-CDR1) SEQ ID NO: 68 TGTSSVVGGHDYVS
BCA7-2D11 (VL-CDR2) SEQ ID NO: 69 DVSNRPS
BCA7-2D11 (VL-CDR3) SEQ ID NO: 70 GSYTSSGSYV

BCA7-2G2
BCA7-2G2 (VH-CDR1) SEQ ID NO: 71 TAWMS
BCA7-2G2 (VH-CDR2) SEQ ID NO: 72 RIKSKSDGGTTDYAAPVKG
BCA7-2G2 (VH-CDR3) SEQ ID NO: 73 GGGTYGY
BCA7-2G2 (VL-CDR1) SEQ ID NO: 74 TGTSSSVGGGRQYVS
BCA7-2G2 (VL-CDR2) SEQ ID NO: 75 DVSNRPS
BCA7-2G2 (VL-CDR3) SEQ ID NO: 76 GSYTSSGSYV

BCA7-2D8
BCA7-2D8 (VH-CDR1) SEQ ID NO: 77 TAWMS
BCA7-2D8 (VH-CDR2) SEQ ID NO: 78 RIKSKSDGGTTDYAAPVKG
BCA7-2D8 (VH-CDR3) SEQ ID NO: 79 GGGTYTY
BCA7-2D8 (VL-CDR1) SEQ ID NO: 80 TGTSSSIGDSYYVS
BCA7-2D8 (VL-CDR2) SEQ ID NO: 81 DVSNRPS
BCA7-2D8 (VL-CDR3) SEQ ID NO: 82 GSYTSSGSYV

BCA7-2E8
BCA7-2E8 (VH-CDR1) SEQ ID NO: 83 TAWMS
BCA7-2E8 (VH-CDR2) SEQ ID NO: 84 RIKSKSDGGTTDYAAPVKG
BCA7-2E8 (VH-CDR3) SEQ ID NO: 85 GGGTYGY
BCA7-2E8 (VL-CDR1) SEQ ID NO: 86 TGTSSDVGGYNYVS
BCA7-2E8 (VL-CDR2) SEQ ID NO: 87 DVSNRPS
BCA7-2E8 (VL-CDR3) SEQ ID NO: 88 GSLRSNGDYV

BCA7-2C5
BCA7-2C5 (VL lambda-CDR1) SEQ ID NO: 89 TGTSSAHGGHYYVS
BCA7-2C5 (VL lambda-CDR2) SEQ ID NO: 90 DVSNRPS
BCA7-2C5 (VL lambda-CDR3) SEQ ID NO: 91 GSYTSSGSYV
```

EXAMPLES

The following examples are meant to be illustrative and can be used to further understand embodiments of the present disclosure and should not be construed as limiting the scope of the present teachings in any way.

Example 1: Generating Anti-BCMA Antibodies

Monoclonal phage ELISA was used to select antibodies from a fully human antibody library. Standard panning procedures were employed to select antibodies that bound BCMA protein and BCMA-expressing RPMI8226 cell lines. scFv were clones into an STI-Fc vector, or the heavy and light chain variable regions were cloned into the STI heavy chain and lambda light chain vectors containing their respective constant regions, using standard molecular biology techniques. Plasmids containing verified insert sequences were used for transient expression in CHO-S cells and the antibodies were purified using protein A resin. The selected anti-BCMA antibodies included BCA7, BC4C9, BC5C4 and BC6G8.

The BCA7 antibody clone was subjected to affinity maturation using soft randomized phage library. BCA8 phagemid DNA was used as PCR template. Six degenerate oligonucleotides were used as PCR primers to introduce mutations into the six CDR regions. PCR fragments were digested with a restriction enzyme and ligated into a linearized phagemid vector pCGMT3, and electroporated into *E. coli* SS320 cells. Panning was performed using human BCMA protein and a BCMA-expressing PRMI8226 cell line. The selected anti-BCMA antibodies included BCA7-2C5, BCA7-2E1, BCA7-2D11, BCA7-2G2, BCA7-2D8 and BCA7-2E8.

Example 2: Measuring Binding Affinities Using Surface Plasmon Resonance

Binding kinetics of anti-BCMA antibodies with his-tagged human BCMA protein (ACROBiosystems, catalog # BCA-H522y-100 ug, UniProt Q02223-1, SEQ ID NO:92) was measured using surface plasmon resonance (SPR). Kinetic interactions between the antibodies and his-tagged BCMA proteins were measured at 25° C. using Biacore T200 surface plasmon resonance (GE Healthcare). Anti-human fragment crystallizable region (Fc region) antibody was immobilized on a CM5 sensor chip to approximately 8000 resonance units (RU) using standard N-hydroxysuccinimide/N-Ethyl-N'-(3-dimethylaminopropyl) carbodiimide hydrochloride (NHS/EDC) coupling methodology. The anti-BCMA antibody (2 µg/mL) was captured for 60 seconds at a flow rate of 10 µL/minute. The his-tagged BCMA protein was run at six different dilutions of 3.12, 6.25, 12.5, 25, 50, 100 and 200 nM, in a running buffer of 0.01 M HEPES pH 7.4, 0.15 M NaCl, 3 mM EDTA, 0.05% v/v Surfactant P20 (HBS-EP+). The 25 nM BCMA protein run was measured two times. All measurements were conducted in HBS-EP+ buffer with a flow rate of 30 µL/minute. A 1:1 (Langmuir) binding model was used to fit the data. The SPR sensorgrams of anti-BCMA antibodies BCA7, GSK J6M0, BC4C9 and BC5C4 are shown in FIGS. 1, 2, 3 and 4, respectively, and their corresponding binding kinetics are listed in Table 3.

TABLE 3

| | ka (1/Ms) | kd (1/s) | $K_D$ (M) | Chi$^2$ (RU$^2$) | Model |
|---|---|---|---|---|---|
| BC4C9 | 2.08E+04 | 5.67E−04 | 2.73E−08 | 0.146 | 1:1 Binding |
| BC5C4 | 3.56E+06 | 3.30E−02 | 9.27E−09 | 0.281 | 1:1 Binding |
| BCA7 | 1.03E+03 | 1.80E−02 | 1.75E−05 | 0.0847 | 1:1 Binding |
| GSK-J6M0 | 1.97E+05 | 4.96E−04 | 2.52E−09 | 0.022 | 1:1 Binding |

Binding kinetics of optimized anti-BCMA antibodies BCA7-2C5, BCA7-2D11, BCA7-2G2, BCA7-2E1, BCA7-2D8 and BCA7-2E8, with his-tagged human BCMA protein (ACROBiosystems, catalog # BCA-H522y-100 ug), were analyzed in the manner as described above. The sensorgrams are shown in FIGS. 5-10, respectively, and their corresponding binding kinetics are listed in Table 4. The optimized anti-BCMA antibodies exhibited markedly improved binding to BCMA protein.

TABLE 4

| | ka1 (1/Ms) | kd1 (1/s) | ka2 (1/s) | kd2 (1/s) | $K_D$ (M) | Chi$^2$ (RU$^2$) |
|---|---|---|---|---|---|---|
| BCA7 | 785.9 | 0.03493 | 0.004635 | 0.01204 | 3.21E−05 | 0.0841 |
| 2C5 | 1.37E+06 | 0.04216 | 8.47E−04 | 0.00145 | 1.94E−08 | 0.0531 |
| 2E1 | 2.51E+06 | 0.1506 | 0.001797 | 9.29E−04 | 2.04E−08 | 0.0245 |
| 2D11 | 1.87E+06 | 0.2608 | 0.003815 | 7.10E−04 | 2.19E−08 | 0.0131 |
| 2G2 | 3.21E+04 | 0.003761 | 0.001432 | 0.001209 | 5.37E−08 | 1.32 |
| 2D8 | 2.43E+06 | 1.092 | 0.01132 | 0.002598 | 8.38E−08 | 0.0682 |
| 2E8 | 4.87E+04 | 0.02023 | 0.01189 | 0.007074 | 1.55E−07 | 1.42 |

Example 3: Measuring Binding Affinities Using Surface Plasmon Resonance

Figure 11A:
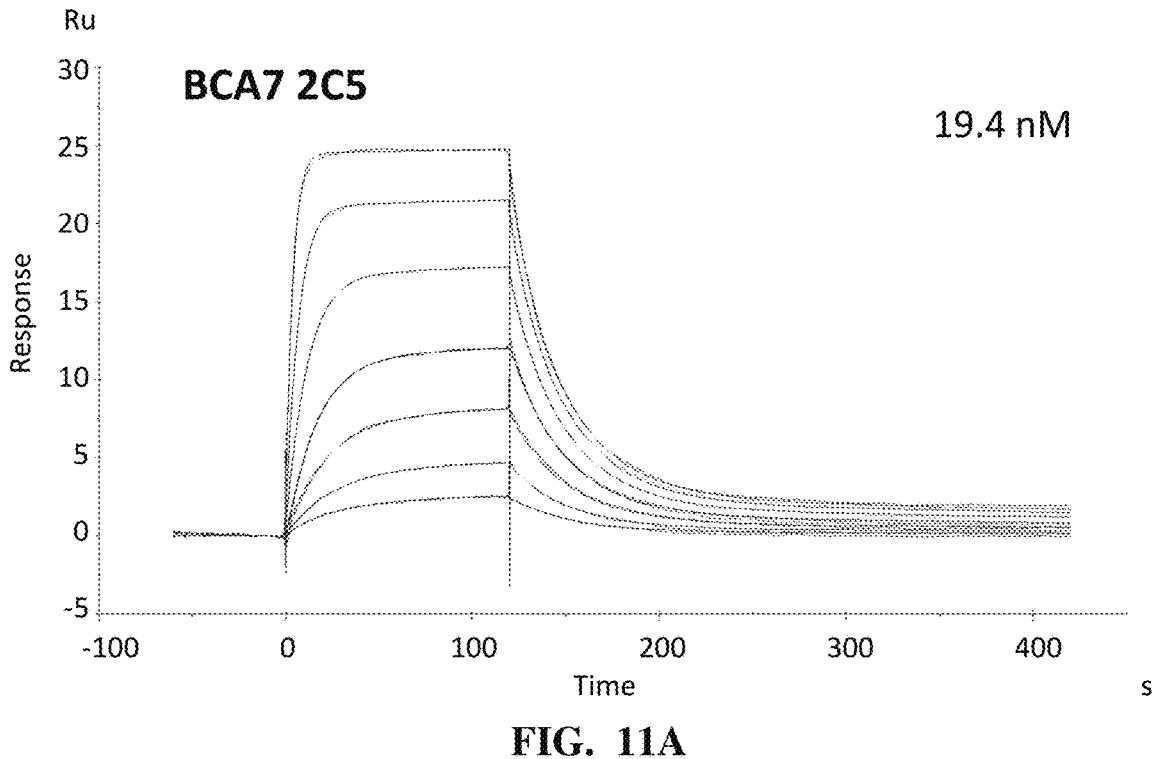
FIG. 11A shows an SPR sensorgram of binding kinetics of BCA7-2C5 antibody to human BCMA protein.
Figure 11B:
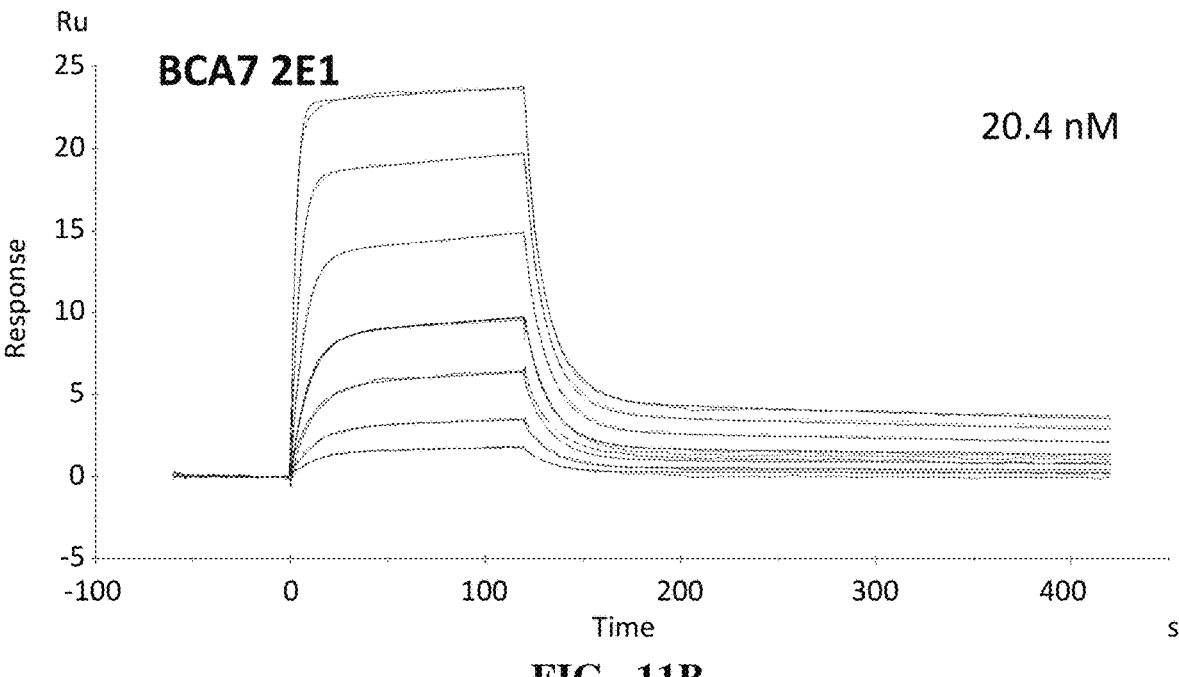
FIG. 11B shows an SPR sensorgram of binding kinetics of BCA7-2E1 antibody to human BCMA protein.
Figure 12A:
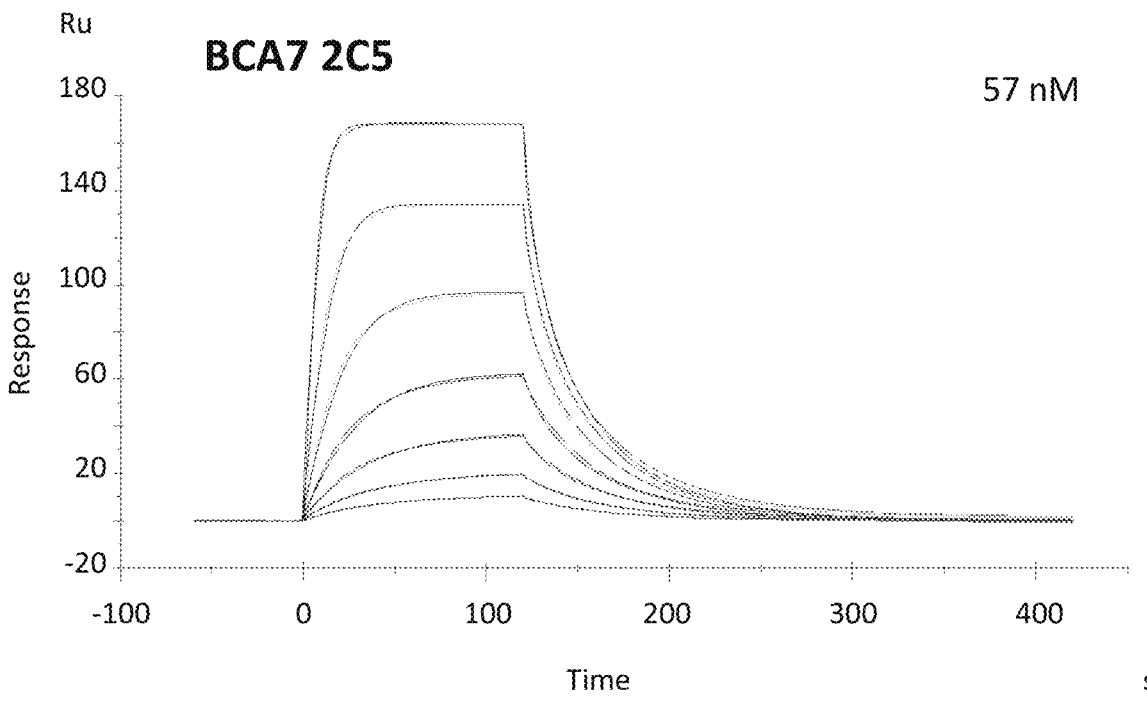
FIG. 12A shows an SPR sensorgram of binding kinetics of BCA7-2C5 antibody to cynomolgus BCMA protein.
Figure 12B:
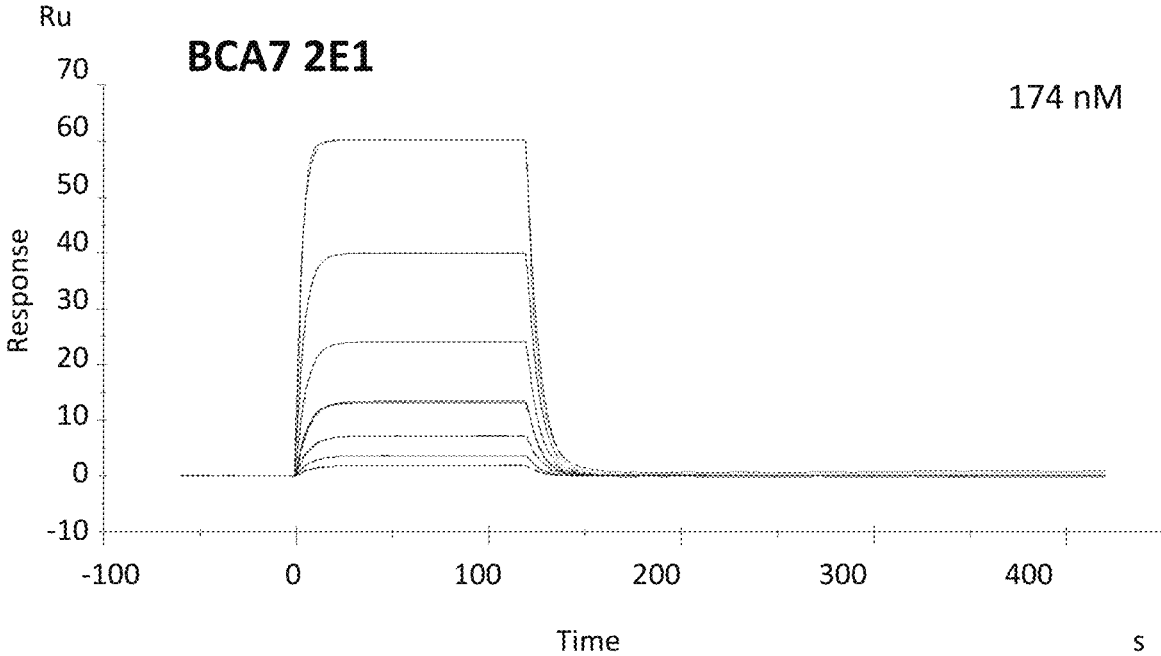
FIG. 12B shows an SPR sensorgram of binding kinetics of BCA7-2E1 antibody to cynomolgus BCMA protein.
Figure 13A:
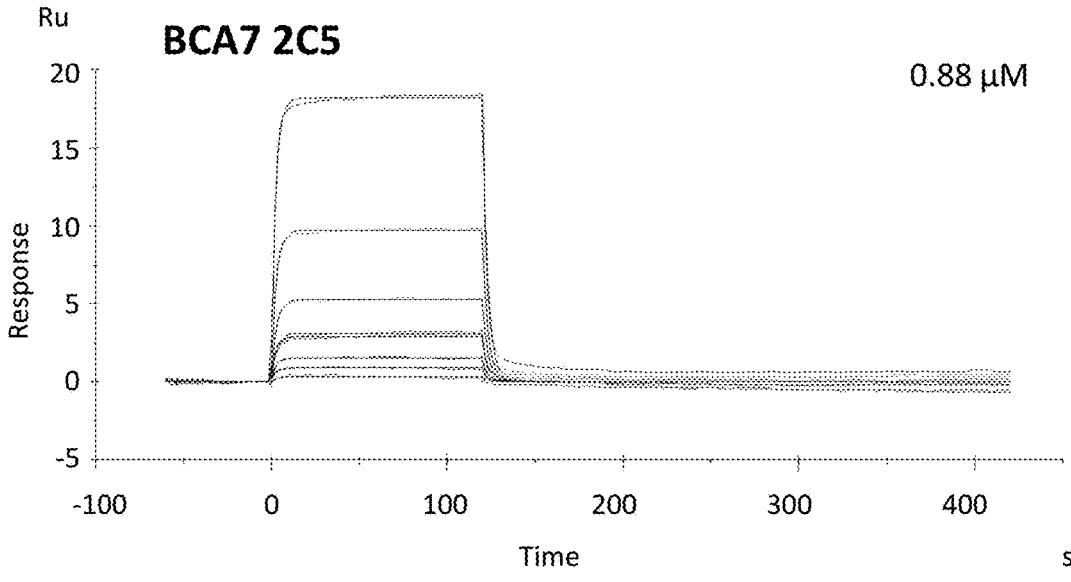
FIG. 13A shows an SPR sensorgram of binding kinetics of BCA7-2C5 antibody to mouse BCMA protein.
Figure 13B:
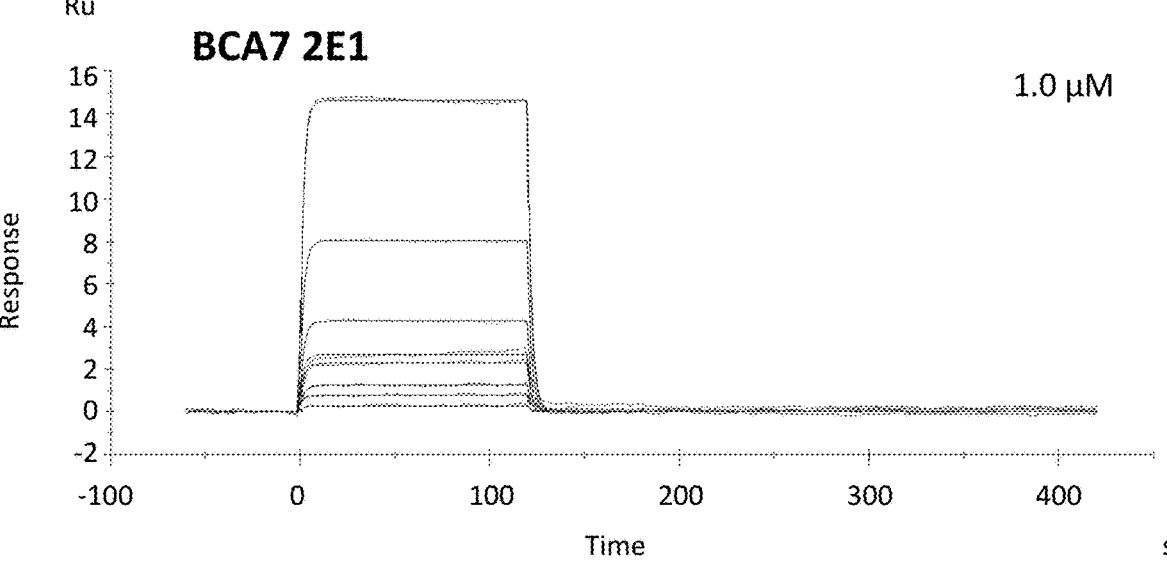
FIG. 13B shows an SPR sensorgram of binding kinetics of BCA7-2E1 antibody to mouse BCMA protein.

Cross reactivity of two of the anti-BCMA antibodies, BCA7-2C5 and BCA7-2E1, with his-tagged human, cynomolgus or mouse BCMA protein were analyzed by SPR in the manner as described above. All three his-tagged BCMA proteins were obtained from ACROBiosystems: his-tagged human BCMA protein (catalog # BCA-H522y-100 ug), his-tagged cynomolgus BCMA protein (catalog # BCA-052H7), and his-tagged mouse BCMA protein (catalog # BCA-M52H3). The sensorgrams are shown in: FIGS. 11A and B (2C5 and 2E1 antibodies, respectively, binding to human BCMA protein) with $K_D$ values; FIGS. 12A and B (2C5 and 2E1 antibodies, respectively, binding to cynomolgus BCMA protein) with $K_D$ values; and FIGS. 13A and B (2C5 and 2E1, respectively, binding to mouse BCMA protein) with KC values.

Example 4: ELISA Cross-Reactivity

Figure 14:
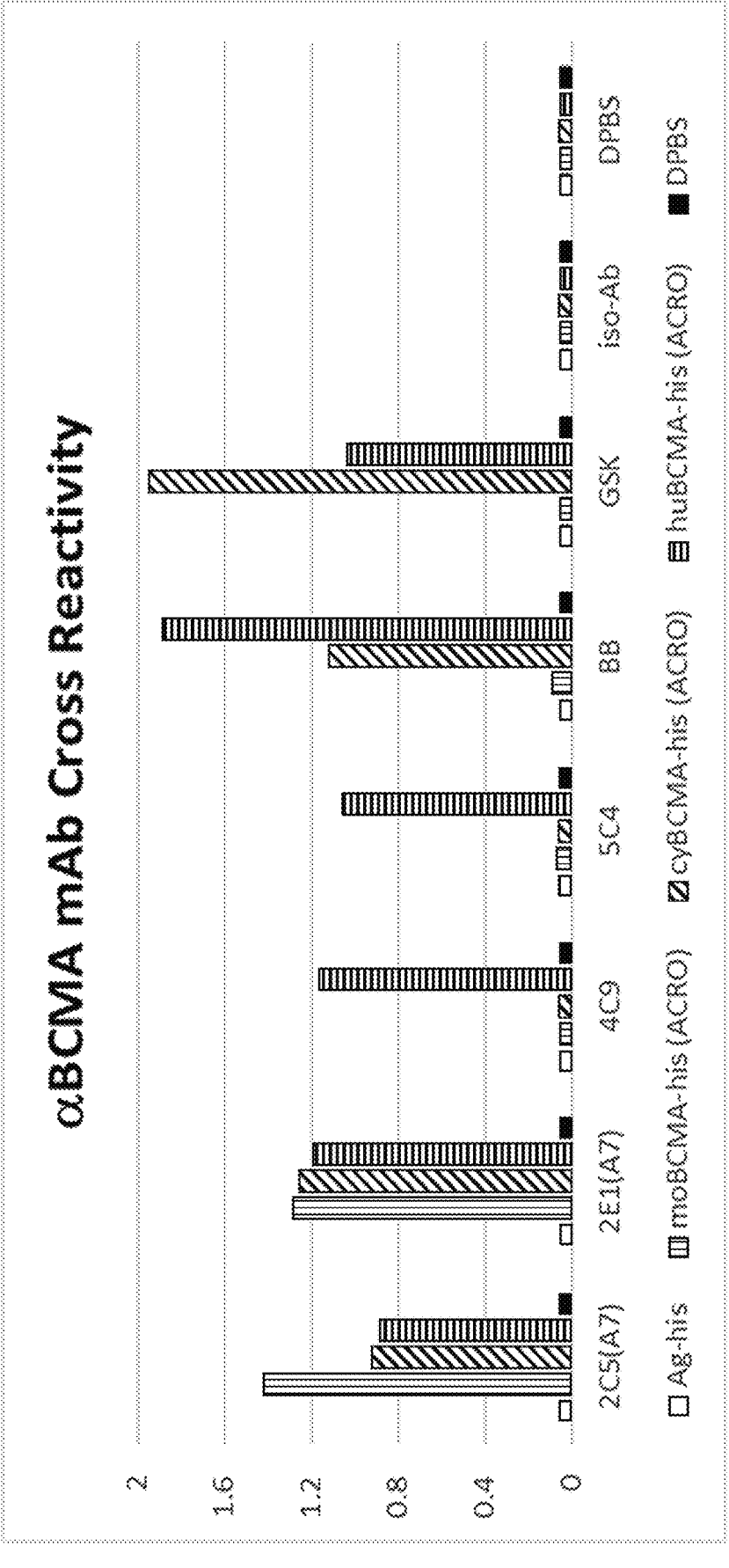
FIG. 14 is a bar graph showing the results of an ELISA assay for various anti-BCMA antibodies cross reactivity with mouse, cynomolgus or human BCMA protein. The vertical axis shows absorbance.

Cross-reactivity of the anti-BCMA antibodies with his-tagged BCMA protein from human, cynomolgus or mouse, were analyzed by ELISA assay. The Ni-NTA plate was coated with his-tagged BCMA proteins (listed in Example 2 above) at 2 µg/mL, then reacted with an anti-BCMA antibody at 20 µg/mL, and reacted with anti-human Fc HRP (KPL Scientific, catalog #5220-0279) at 1:2500 dilution. FIG. 14 shows 8 sets, from left to right, anti-BCMA antibodies 2C5, 2E1, 4C9, 5C4, Bluebird C11D5 (BB C11D5), GSK J6M0, isotype control antibody, and Dulbecco's Phosphate-Buffered Saline. Each set includes 5 test antigens or buffer, from left to right: negative control antigen, his-tagged mouse BCMA protein, his-tagged cynomolgus BCMA protein, his-tagged human BCMA protein, and Dulbecco's Phosphate-Buffered Saline. FIG. 14 shows that GSK and Bluebird antibodies bind human and cynomolgus but not mouse BCMA protein; 2C5 and 2E1 antibodies bind human, cynomolgus and mouse BCMA protein; and 4C9 and 5C4 antibodies bind only human BCMA protein.

Example 5: Flow Cytometry Assay

Figure 15:
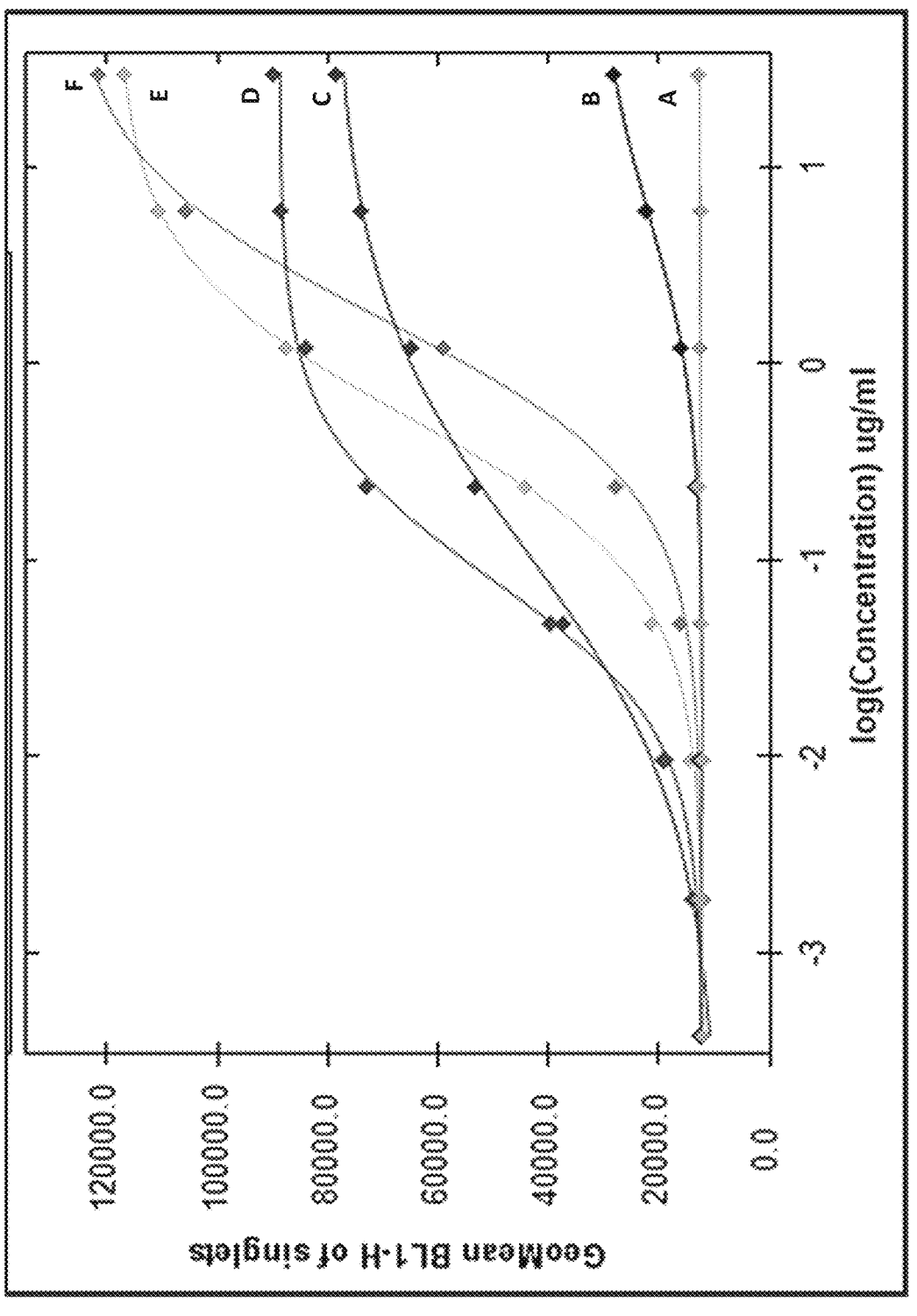
FIG. 15 is a graph showing the results of binding various anti-BCMA antibodies to MM1R cell line via flow cytometry.

Flow cytometry was used to test antibody binding to multiple myeloma cell line MM1R, using various anti-BCMA antibodies (5× serial dilution) and 80,000 cells per well. The secondary antibody was FITC AffiniPure FAB2 fragment goat anti-human IgG (H+L) (from Jackson Immuno Research). FIG. 15 shows the results for (A) control isotype; (B) BCA7 antibody; (C) BCA-2E1 antibody; (D) BCA7-2C5 antibody; (E) Bluebird C11D5 antibody; and (F) GSK J6M0 antibody. A BL-1 detector (IntelliCyt iQue Screener Plus) which detects at 530 nm was used. The geometric mean is reported.

Example 6: Epitope Mapping with Wild Type BCMA Protein

Figure 16:
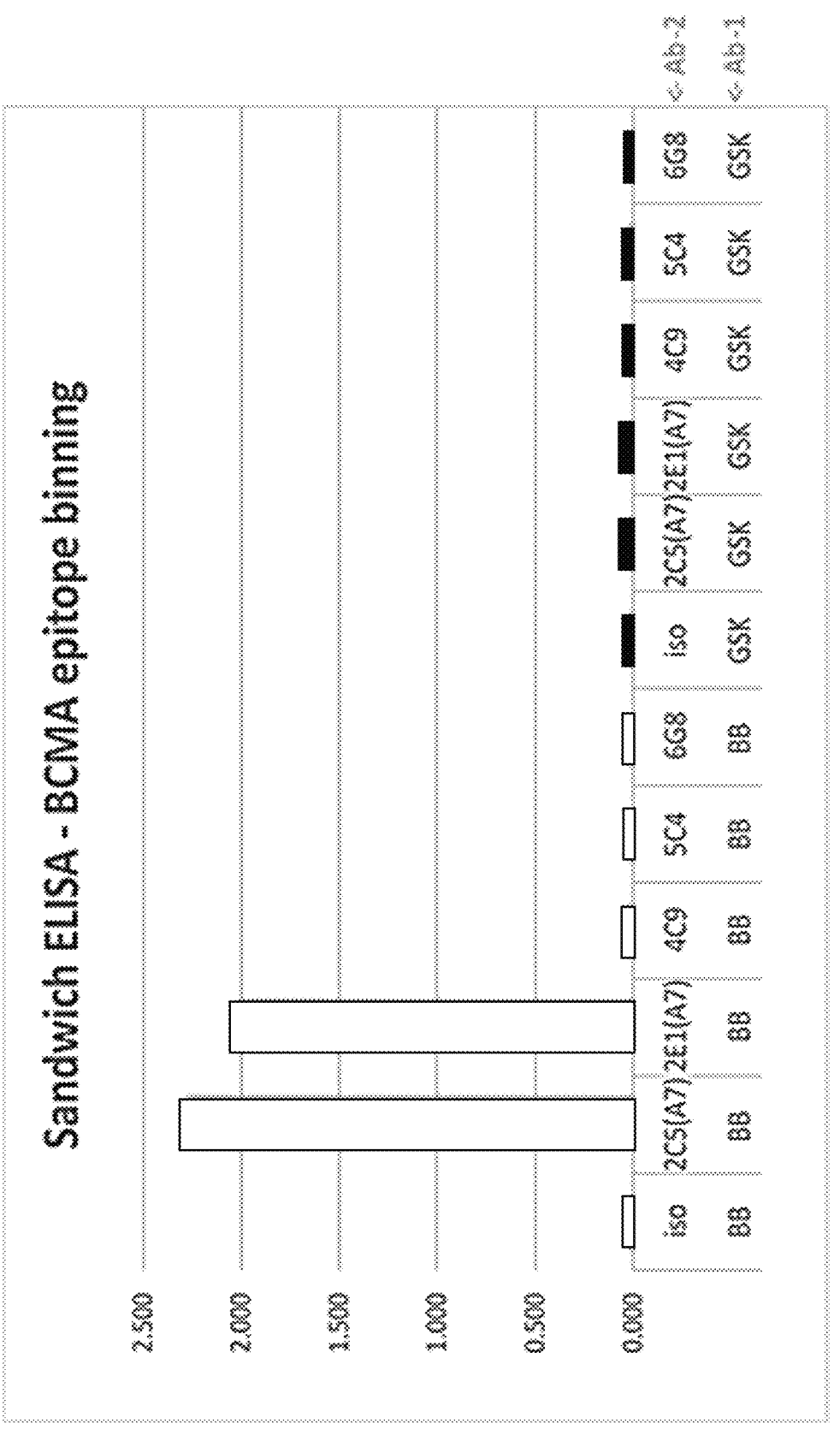
FIG. 16 is a bar graph showing the results of an epitope mapping assay using a sandwich ELISA procedure. The vertical axis shows absorbance.

Epitope mapping of the various anti-BCMA antibodies was conducted using a sandwich-style ELISA assay. The first antibody (Ab-1) was either Bluebird C11D5 (white bars with "BB" label in FIG. 16) or GSK J6M0 (black bars with "GSK" label in FIG. 16) (both at 4 μg/mL), the antigen was his-tagged human BCMA protein (ACROBiosystems, catalog # BCA-H522y-100 ug), the second antibody was one of the various anti-BCMA antibodies, and the secondary antibody was anti-lambda/HRP at 1:2500. The various anti-BCMA antibodies included: isotype control antibody; 2C5; 2E1; 4C9; 5C4; and 6G8. FIG. 16 shows the results of epitope mapping where the BCA7 variant antibodies (2C5, 2E1, 4C9, 5C4, and 6G8) bind overlapping epitope with the GSK antibody. The BCA7 variant antibodies (4C9, 5C4 and 6G8) bind overlapping epitope with the Bluebird antibody.

Example 7: Mutating BCMA Protein for Epitope Mapping

DNA fragments encoding wild type and mutant BCMA proteins were synthesized by IDT, and were cloned into STI vector with C-terminal mouse Fc tag. The verified plasmids were used for transient expression in CHO-S cells. The wild type and mutant BCMA proteins were purified using protein A resin. BCMA wild type protein comprises the amino acid sequence of SEQ ID NO:2. BCMA mutant-1 protein comprises the amino acid sequence of SEQ ID NO:3. BCMA mutant-2 protein comprises amino acid sequence of SEQ ID NO:4.

Figure 17:
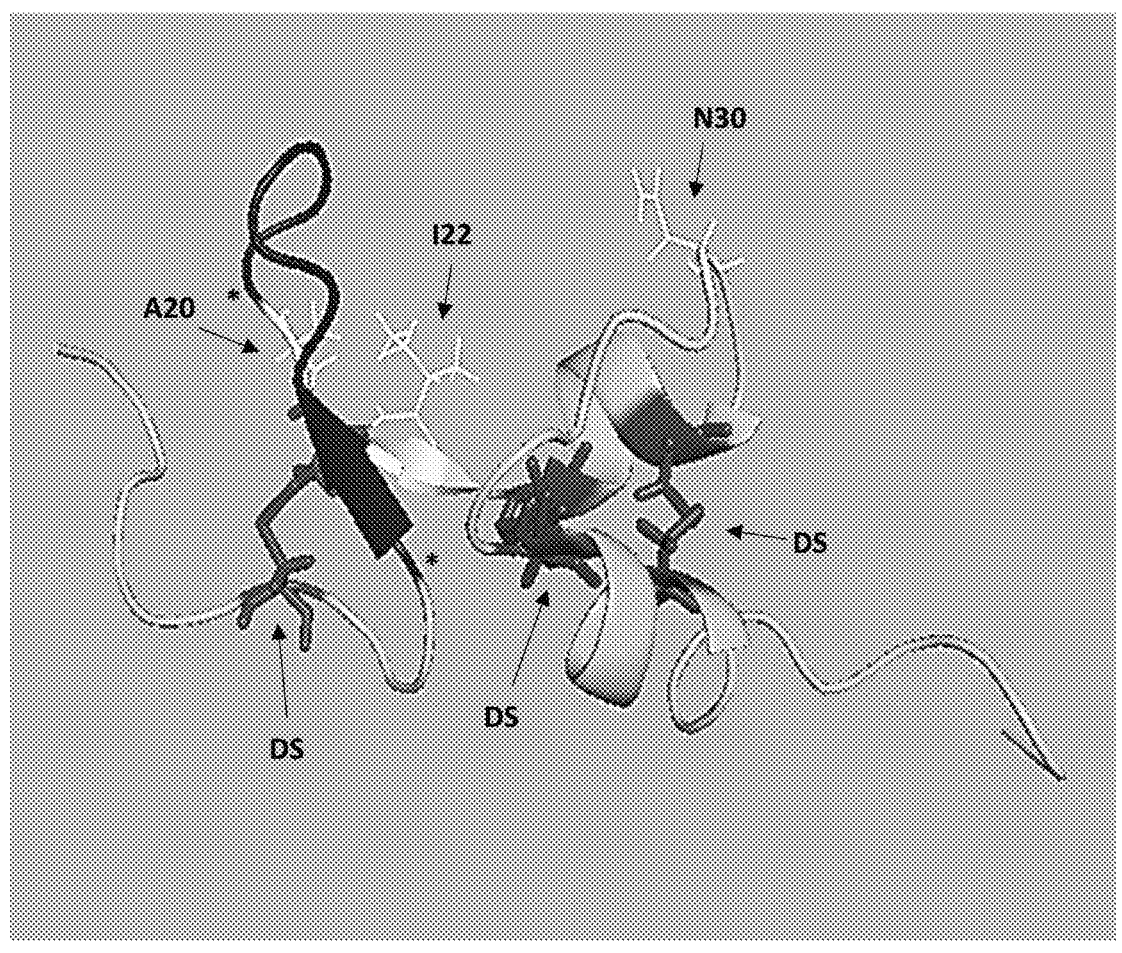
FIG. 17 shows a ribbon diagram of a representation of a BCMA protein.

FIG. 17 shows a ribbon diagram of a representation of BCMA protein. The asterisks designate the region having an amino acid sequence EYFDSLLH (SEQ ID NO:28) which is disrupted in BCMA mutant-1 protein having two point mutations at L17G and L18G. The locations of disulfide bridges and residues A20, 122, and N30 are also shown.

Example 8: Bio-Layer Interferometry to Measure Protein-Protein Binding

Figure 18:
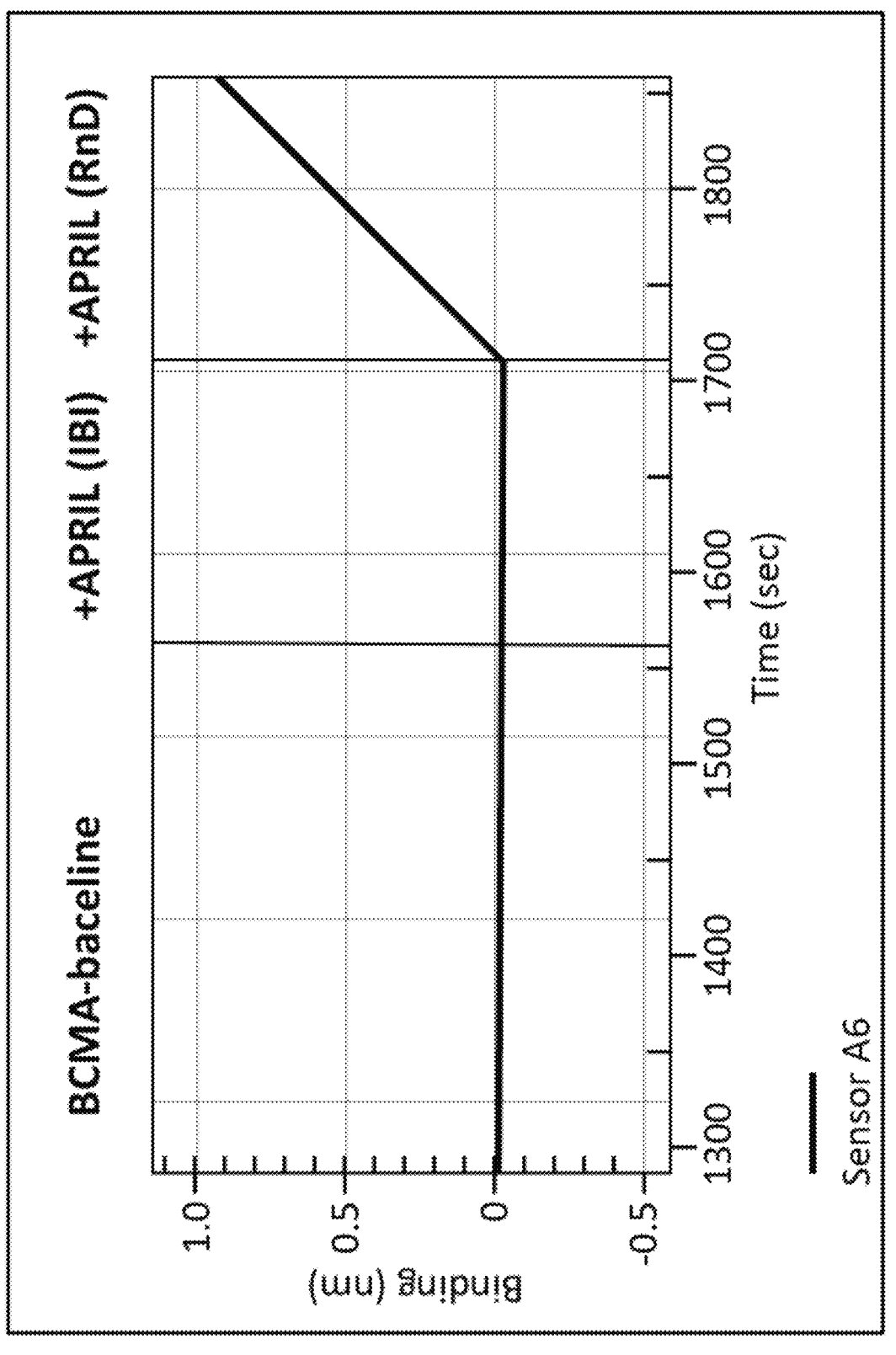
FIG. 18 is a graph showing the results of a protein-protein binding assay conducted using bio-layer interferometry.

Bio-layer interferometry was used to measure binding between APRIL protein and wild type BCMA protein. Wild type human BCMA-mouse Fc protein (SEQ ID NO:5) was loaded onto an AR2G sensor (OctetRED96e from ForteBio) and reacted with one of two different sources of human APRIL protein (from IBI Scientific, catalog # RPH-151;

R&D Systems, catalog #5860-AP-010/CF). The results are shown in FIG. 18, which indicates that human BCMA protein binds human APRIL protein from R&D Systems, but not human APRIL from IBI Scientific.

Figure 19:
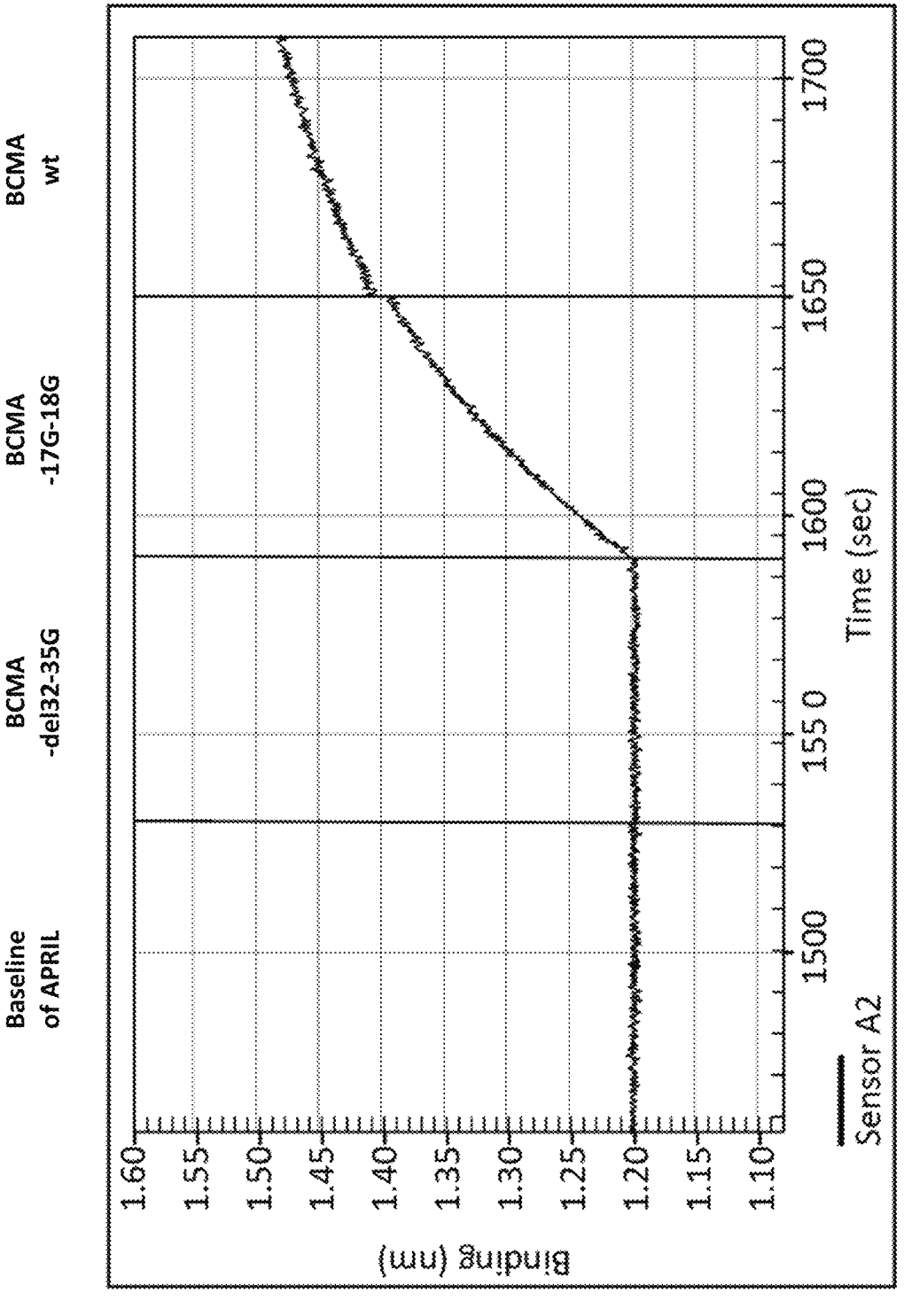
FIG. 19 is a graph showing the results of a protein-protein binding assay conducted using bio-layer interferometry.

Bio-layer interferometry was also used to measure binding between APRIL protein, and wild type or mutant BCMA proteins. Human APRIL protein (R&D Systems, catalog #5860-AP-010/CF) was loaded onto an Ar2G sensor (OctetRET96e) and reacted with 2.5 μg/mL of one of three types of human BCMA proteins including: wild type human BCMA-mouse Fc (SEQ ID NO:5), mutant-1 human BCMA-mouse Fc (17G-18G; SEQ ID NO:6), or mutant-2 human BCMA-mouse Fc (de132-35G; SEQ ID NO:7). FIG. 19 shows wild type BCMA protein binds APRIL, mutant-1 BCMA protein (double point mutation 17G-18G) exhibited loss of binding to APRIL, and mutant-2 BCMA protein retains some binding capability to APRIL protein.

Example 9: Bio-Layer Interferometry for Epitope Mapping

Figure 20:
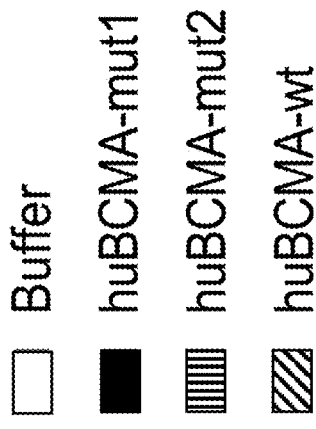
FIG. 20 is a bar graph showing the results of an epitope mapping assay using bio-layer interferometry.
Figure 20:
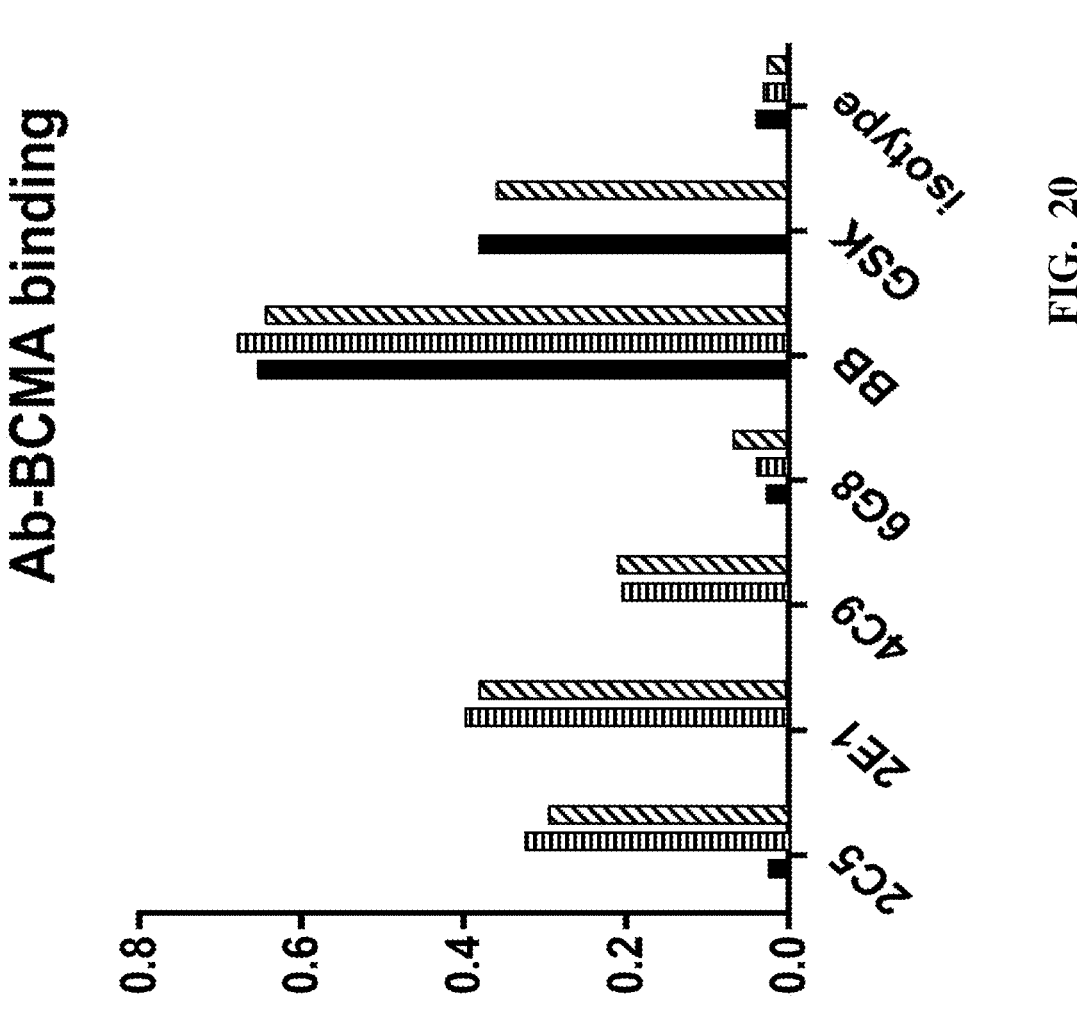

The results of the protein-protein binding assays described in Example 8 were used to design an epitope mapping assay using bio-layer interferometry. Various anti-BCMA antibodies (2C5, 2E1, 4C9, 6G8, Bluebird C11D5, GSK J6M0, or isotype control) (100 nM) were loaded onto AR2G sensors and reacted with buffer or one of three types of human BCMA proteins including: including: wild type human BCMA-mouse Fc (SEQ ID NO:5), mutant-1 human BCMA-mouse Fc (double mutation 17G-18G; SEQ ID NO:6), or mutant-2 human BCMA-mouse Fc (mutation del32-35G; SEQ ID NO:7). FIG. 20 shows that: antibodies 2C5, 2E1 and 4C9 bind wild type and mutant-2 BCMA proteins and exhibit reduced binding to mutant-1 BCMA protein; Bluebird C11D5 antibody binds wild type and both mutant versions of BCMA protein; and GSK J6M0 antibody binds wild type and mutant-1 BCMA proteins and exhibits reduced binding to mutant-2 BCMA protein. Antibody 6G8 exhibits significantly reduced binding to all forms of BCMA protein used in this assay. This data indicates that antibodies 2C5, 2E1 and 4C9 bind an epitope of human BCMA protein that differs from the epitope bound by Bluebird and GSK antibodies.

Example 10: Bio-Layer Interferometry for Measuring APRIL-Blocking Activity

Figure 21:
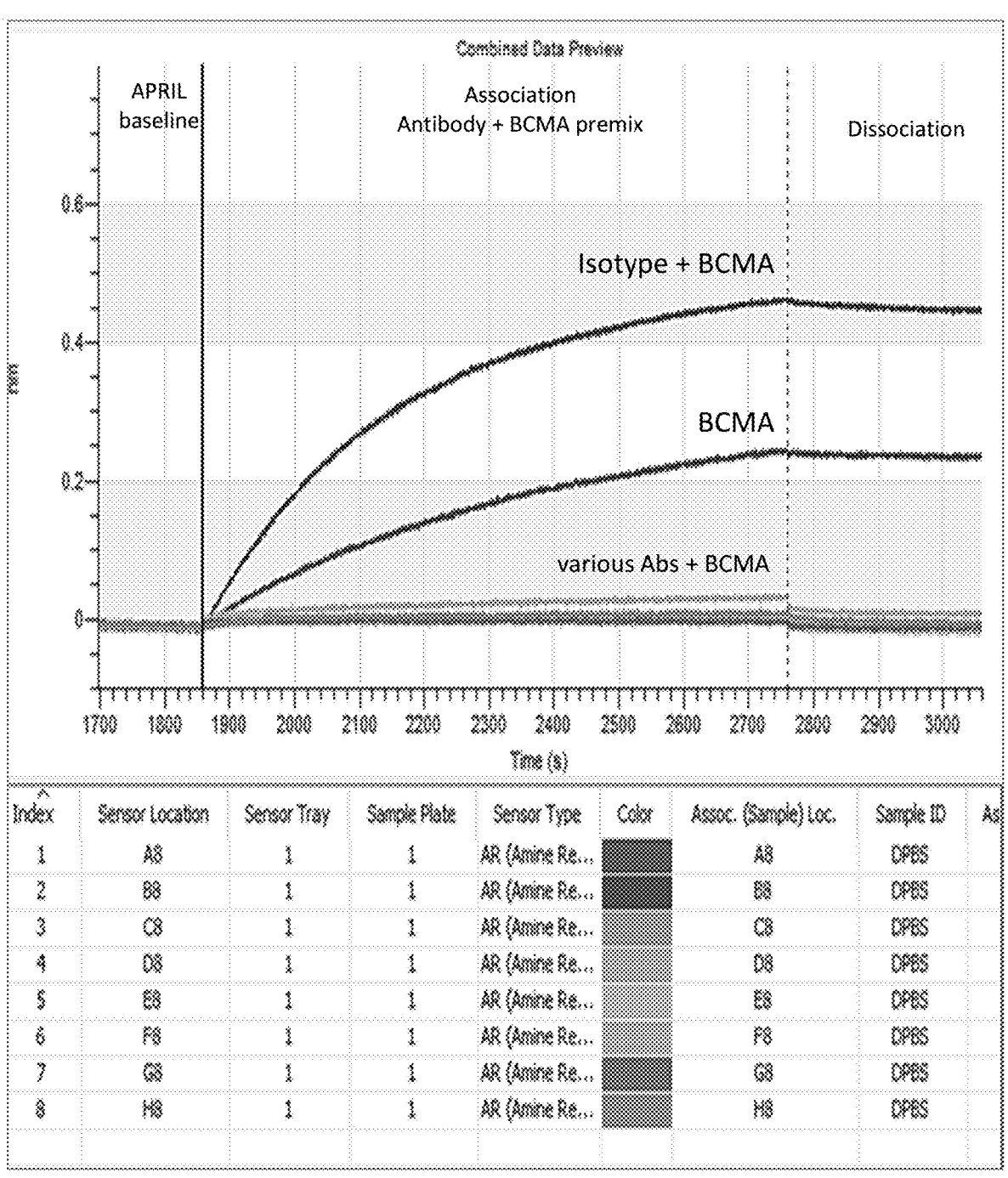
FIG. 21 shows the results of a protein binding blocking assay using bio-layer interferometry.

Bio-layer interferometry was used to assess the capability of the various anti-BCMA antibodies to bind a human BCMA epitope and block binding of human APRIL to the human BCMA epitope. Human APRIL protein (R&D Systems, catalog #5860-AP-010/CF) was loaded onto an AR2G sensor (2 μg/mL) and reacted with pre-mixed human BCMA protein (2 μg/mL) with one of the various anti-BCMA antibodies or an isotype control (25 μg/mL) for 1 hour. The results in FIG. 21 show that the various anti-BCMA antibodies (2C5, 2E1, 4C9, 5C4, Bluebird C11D5 and GSK J6M0) blocked BCMA protein binding to APRIL protein.

Example 11: Bio-Layer Interferometry to Measure Cross-Reaction

Bio-layer interferometry was used to measure cross-binding between (1) two different anti-BCMA antibodies (BCA7-2C5 or BB C11D5) or a control isotype, and (2) various human antigens including TACI and BAFFR.

Immobilization of antibody was achieved through standard EDC-catalyzed amide bond formation to create a covalent bond between a reactive amine on the protein and the carboxy-terminated biosensor surface. Briefly, AR2G sensors (OctetRED96e from ForteBio) were activated by EDC-NHS for 6 minutes, then 5 ug/ml antibodies were loaded (BCA7-2C5 antibody, Bluebird C11D5 chimeric antibody, or a human IgG isotype antibody) in 10 mM acetate buffer pH 5.0 for 6 minutes, followed by quenching for 6 minutes with 1M ethanolamine pH 8.5. The 3 minutes baseline step removed any unbound antibody from the biosensor, followed by 1.5 minutes each for association of three analyte proteins TACI (human TACI/TNFRSF13B (CD267) His-tag, from Sino Biological, 1 ug/mL in PBS), BAFFR (human BAFFR/TNFRSF13C (CD268) Fc tag) from Sino Biological, 2 ug/mL in PBS), and human BCMA protein (in-house made with mouse Fc, 2 ug/mL in PBS). The assay steps are summarized in Table 4 below:

54

TABLE 4

| Step No. | Step Name | Step Time (seconds) | Step Type Name |
|---|---|---|---|
| 1 | Baseline 1 | 240 | Baseline |
| 2 | Activation | 360 | Activation |
| 3 | Loading | 360 | Loading |
| 4 | Quenching | 360 | Quenching |
| 5 | Baseline 2 | 180 | Baseline |
| 6 | Association | 90 | Association |
| 7 | Association | 90 | Association |
| 8 | Association | 90 | Association |
| 9 | Dissociation | 180 | Dissociation |

Figure 22:
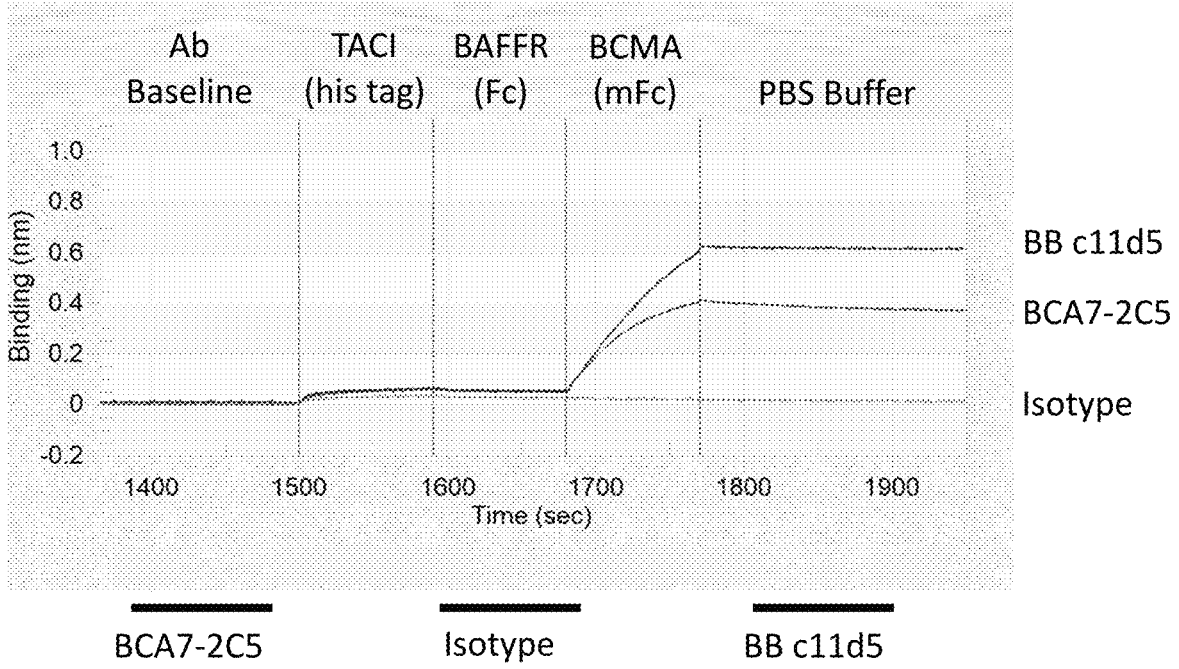
FIG. 22 shows the results of an antibody-protein binding assay conducted using bio-layer interferometry.

The results in FIG. 22 show that the anti-BCMA antibodies (BCA7-2C5 and BB C11D5) bind to BCMA protein but do not bind to TACI or BAFFR proteins.

What is claimed:

1. A fully human anti-BCMA antibody, or an antigen-binding fragment thereof, comprising a heavy chain and a light chain, wherein (a) the heavy chain comprises: a heavy chain complementarity determining region 1 (CDR1) having the amino acid sequence of SEQ ID NO:29, a heavy chain CDR2 having the amino acid sequence of SEQ ID NO:30, a heavy chain CDR3 having the amino acid sequence of SEQ ID NO:31; and the light chain comprises: a light chain CDR1 having the amino acid sequence of SEQ ID NO:32, a light chain CDR2 having the amino acid sequence of SEQ ID NO:33, and a light chain CDR3 having the amino acid sequence of SEQ ID NO:34;

wherein (b) the heavy chain comprises: a heavy chain CDR1 having the amino acid sequence of SEQ ID NO:35, a heavy chain CDR2 having the amino acid sequence of SEQ ID NO:36, a heavy chain CDR3 having the amino acid sequence of SEQ ID NO:37; and the light chain comprises: a light chain CDR1 having the amino acid sequence of SEQ ID NO:38, a light chain CDR2 having the amino acid sequence of SEQ ID NO:39, and a light chain CDR3 having the amino acid sequence of SEQ ID NO:40;

wherein (c) the heavy chain comprises: a heavy chain CDR1 having the amino acid sequence of SEQ ID NO:41, a heavy chain CDR2 having the amino acid sequence of SEQ ID NO:42, a heavy chain CDR3 having the amino acid sequence of SEQ ID NO:43; and the light chain comprises: a light chain CDR1 having the amino acid sequence of SEQ ID NO:44, a light chain CDR2 having the amino acid sequence of SEQ ID NO:45, and a light chain CDR3 having the amino acid sequence of SEQ ID NO:46;

wherein (d) the heavy chain comprises: a heavy chain CDR1 having the amino acid sequence of SEQ ID NO:47, a heavy chain CDR2 having the amino acid sequence of SEQ ID NO:48, a heavy chain CDR3 having the amino acid sequence of SEQ ID NO:49; and the light chain comprises: a light chain CDR1 having the amino acid sequence of SEQ ID NO:50, a light chain CDR2 having the amino acid sequence of SEQ ID NO:51, and a light chain CDR3 having the amino acid sequence of SEQ ID NO:52;

wherein (e) the heavy chain comprises: a heavy chain CDR1 having the amino acid sequence of SEQ ID NO:53, a heavy chain CDR2 having the amino acid sequence of SEQ ID NO:54, a heavy chain CDR3 having the amino acid sequence of SEQ ID NO:55; and the light chain comprises: a light chain CDR1 having the amino acid sequence of SEQ ID NO:56, a light chain CDR2 having the amino acid sequence of SEQ ID NO:57, and a light chain CDR3 having the amino acid sequence of SEQ ID NO:58;

wherein (f) the heavy chain comprises: a heavy chain CDR1 having the amino acid sequence of SEQ ID NO:59, a heavy chain CDR2 having the amino acid sequence of SEQ ID NO:60, a heavy chain CDR3 having the amino acid sequence of SEQ ID NO:61; and the light chain comprises: a light chain CDR1 having the amino acid sequence of SEQ ID NO:62, a light chain CDR2 having the amino acid sequence of SEQ ID NO:63, and a light chain CDR3 having the amino acid sequence of SEQ ID NO:64;

wherein (g) the heavy chain comprises: a heavy chain CDR1 having the amino acid sequence of SEQ ID NO:65, a heavy chain CDR2 having the amino acid sequence of SEQ ID NO:66, a heavy chain CDR3 having the amino acid sequence of SEQ ID NO:67; and the light chain comprises: a light chain CDR1 having the amino acid sequence of SEQ ID NO:68, a light chain CDR2 having the amino acid sequence of SEQ ID NO:69, and a light chain CDR3 having the amino acid sequence of SEQ ID NO:70;

wherein (h) the heavy chain comprises: a heavy chain CDR1 having the amino acid sequence of SEQ ID NO:71, a heavy chain CDR2 having the amino acid sequence of SEQ ID NO:72, a heavy chain CDR3 having the amino acid sequence of SEQ ID NO:73; and the light chain comprises: a light chain CDR1 having the amino acid sequence of SEQ ID NO:74, a light chain CDR2 having the amino acid sequence of SEQ ID NO:75, and a light chain CDR3 having the amino acid sequence of SEQ ID NO:76;

wherein (i) the heavy chain comprises: a heavy chain CDR1 having the amino acid sequence of SEQ ID NO:77, a heavy chain CDR2 having the amino acid sequence of SEQ ID NO:78, a heavy chain CDR3 having the amino acid sequence of SEQ ID NO:79; and the light chain comprises: a light chain CDR1 having the amino acid sequence of SEQ ID NO:80, a light chain CDR2 having the amino acid sequence of SEQ ID NO:81, and a light chain CDR3 having the amino acid sequence of SEQ ID NO:82;

wherein (j) the heavy chain comprises: a heavy chain CDR1 having the amino acid sequence of SEQ ID NO:83, a heavy chain CDR2 having the amino acid sequence of SEQ ID NO:84, a heavy chain CDR3 having the amino acid sequence of SEQ ID NO:85; and the light chain comprises: a light chain CDR1 having the amino acid sequence of SEQ ID NO:86, a light chain CDR2 having the amino acid sequence of SEQ ID NO:87, and a light chain CDR3 having the amino acid sequence of SEQ ID NO:88; or wherein (k) the heavy chain comprises: a heavy chain CDR1 having the amino acid sequence of SEQ ID NO:53, a heavy chain CDR2 having the amino acid sequence of SEQ ID NO:54, a heavy chain CDR3 having the amino acid sequence of SEQ ID NO:55; and the light chain comprises: a lambda light chain CDR1 having the amino acid sequence of SEQ ID NO:89, a lambda light chain CDR2 having the amino acid sequence of SEQ ID NO:90, and a lambda light chain CDR3 having the amino acid sequence of SEQ ID NO:91.

2. A fully human anti-BCMA antibody, or antigen-binding fragment thereof, of claim 1 comprising a heavy chain and a light chain, the heavy chain variable region having at least 95% sequence identity to the amino acid sequence of SEQ ID NO: 8, 10, 12, 14 or 22, and the light chain variable region having at least 95% sequence identity to the amino acid sequence of SEQ ID NO: 9, 11, 13, 15, 16, 17, 18, 19, 20, 21 or 23.

3. A fully human anti-BCMA antibody, or the antigen-binding fragment thereof, comprising a heavy chain variable region and a light chain variable region, wherein the heavy chain variable region and the light chain variable region comprise the amino acid sequences of SEQ ID NO: 8 and 9; SEQ ID NO: 10 and 11; SEQ ID NO: 12 and 13; SEQ ID NO: 14 and 15; SEQ ID NO: 8 and 16; SEQ ID NO: 8 and 17; SEQ ID NO: 8 and 18; SEQ ID NO: 8 and 19; SEQ ID NO: 8 and 20; SEQ ID NO: 8 and 21; or SEQ ID NO: 22 and 23.

4. The antigen-binding fragment of claim 2, comprising a Fab fragment having a variable domain region from a heavy chain and a variable domain region from a light chain, wherein the variable domain region from the heavy chain comprises a sequence having at least 95% sequence identity to the amino acid sequence of SEQ ID NO: 8, 10, 12, 14 or 22, and wherein the variable domain region from the light chain comprises a sequence having at least 95% sequence identity to the amino acid sequence of SEQ ID NO: 9, 11, 13, 15, 16, 17, 18, 19, 20, 21 or 23.

5. The antigen-binding fragment of claim 2, comprising a single chain antibody comprising a variable domain region from a heavy chain and a variable domain region from a light chain joined together with a peptide linker, wherein the variable domain region from the heavy chain comprises a sequence having at least 95% sequence identity to the amino acid sequence of SEQ ID NO: 8, 10, 12, 14 or 22, and wherein the variable domain region from the light chain comprises a sequence having at least 95% sequence identity to the amino acid sequence of SEQ ID NO: 9, 11, 13, 15, 16, 17, 18, 19, 20, 21 or 23.

6. The fully human anti-BCMA antibody of claim 2, comprising an IgG1, IgG2, IgG3 or IgG4 class antibody.

7. The antibody or antigen-binding fragment of claim 1, that blocks binding between APRIL (A PRoliferation-Inducing Ligand) protein and BCMA protein.

8. The antibody or antigen-binding fragment of claim 1, that binds to BCMA proteins from human, cynomolgus and mouse.

9. The antibody or antigen-binding fragment of claim 1, that binds to cells expressing BCMA protein.

10. The antibody or antigen-binding fragment of claim 1, that binds to human myeloma cells expressing BCMA protein.

11. A pharmaceutical composition, comprising the antibody or antigen-binding fragment of claim 1 and a pharmaceutically-acceptable excipient.

12. A first nucleic acid encoding a first polypeptide comprising the antibody heavy chain variable region of claim 2, wherein the amino acid sequence of the antibody heavy chain variable region has at least 95% sequence identity to the amino acid sequence of SEQ ID NO: 8, 10, 12, 14 or 22, and a second nucleic acid encoding a second polypeptide comprising the antibody light chain variable region of claim 2, wherein the amino acid sequence of the antibody light chain variable region has at least 95% sequence identity to the amino acid sequence of SEQ ID NO: 9, 11, 13, 15, 16, 17, 18, 19, 20, 21 or 23.

13. One or more nucleic acids encoding the antibody or antigen-binding fragment of claim 1.

14. One or more expression vectors comprising one or more promoters operably linked to the first and second nucleic acids of claim 12.

15. One or more expression vectors comprising one or more promoters operably linked to the one or more nucleic acids of claim 13.

16. A host cell harboring the one or more expression vectors of claim 15.

17. A method for preparing the first polypeptide comprising the antibody heavy chain variable region and the second polypeptide comprising the antibody light chain variable region or the antibody or antigen-binding fragment, the method comprising: culturing a population (a plurality) of the host cell of claim 16 under conditions suitable for expressing the first polypeptide and the second polypeptide or the antibody or antigen-binding fragment.

18. The method of claim 17, further comprising: recovering from the population of the host cell the expressed first polypeptide and the expressed second polypeptide or the expressed antibody or antigen-binding fragment.

* * * * *